United States Patent
Wang et al.

(10) Patent No.: US 12,114,990 B2
(45) Date of Patent: Oct. 15, 2024

(54) SYSTEMS AND METHODS FOR ELECTROMYOMETRIAL IMAGING

(71) Applicant: Washington University, St. Louis, MO (US)

(72) Inventors: Yong Wang, St. Louis, MO (US); Hui Wang, St. Louis, MO (US); Wenjie Wu, St. Louis, MO (US); Alison Cahill, Austin, TX (US)

(73) Assignee: Washington University, St. Louis, MO (US)

( * ) Notice: Subject to any disclaimer, the term of this patent is extended or adjusted under 35 U.S.C. 154(b) by 745 days.

(21) Appl. No.: 17/154,870

(22) Filed: Jan. 21, 2021

(65) Prior Publication Data
US 2021/0228147 A1  Jul. 29, 2021

Related U.S. Application Data

(60) Provisional application No. 62/963,984, filed on Jan. 21, 2020.

(51) Int. Cl.
| | |
|---|---|
| A61B 5/00 | (2006.01) |
| A61B 5/296 | (2021.01) |
| A61B 5/313 | (2021.01) |
| A61B 90/00 | (2016.01) |
| G06T 7/00 | (2017.01) |
| G16H 50/20 | (2018.01) |

(52) U.S. Cl.
CPC ............ *A61B 5/4325* (2013.01); *A61B 5/296* (2021.01); *A61B 5/313* (2021.01); *A61B 5/6833* (2013.01); *A61B 90/39* (2016.02); *G06T 7/0014* (2013.01); *G16H 50/20* (2018.01); *A61B 2090/3954* (2016.02); *G06T 2207/30004* (2013.01)

(58) Field of Classification Search
CPC ..... A61B 5/4325; A61B 5/4356; A61B 5/367; A61B 5/296; A61B 5/313; A61B 5/6833; A61B 2562/046; A61B 90/39; A61B 2090/3954; A61B 5/055; A61B 5/004; A61B 5/0073
See application file for complete search history.

(56) References Cited

U.S. PATENT DOCUMENTS

| | | | |
|---|---|---|---|
| 2004/0082870 A1* | 4/2004 | Rudy | A61B 5/6855 600/509 |
| 2009/0062683 A1* | 3/2009 | Calderon | A61B 5/4356 600/546 |
| 2016/0223319 A1* | 8/2016 | Munro | G01S 17/89 |
| 2016/0242671 A1* | 8/2016 | Young | A61B 5/389 |
| 2017/0049379 A1* | 2/2017 | Luo | G01R 33/4833 |
| 2018/0296156 A1* | 10/2018 | Penders | A61B 5/721 |
| 2019/0200886 A1* | 7/2019 | Welsh | A61B 5/291 |
| 2019/0223819 A1* | 7/2019 | Mansi | G06T 15/205 |
| 2019/0328263 A1* | 10/2019 | Marcus | A61B 5/361 |

* cited by examiner

*Primary Examiner* — Daniel L Cerioni
*Assistant Examiner* — Andrew E Hoffpauir
(74) *Attorney, Agent, or Firm* — Polsinelli PC

(57) ABSTRACT

Systems, devices, and methods for system for monitoring uterine contractions non-invasively using surface electrode measurements are described herein.

14 Claims, 51 Drawing Sheets
(39 of 51 Drawing Sheet(s) Filed in Color)

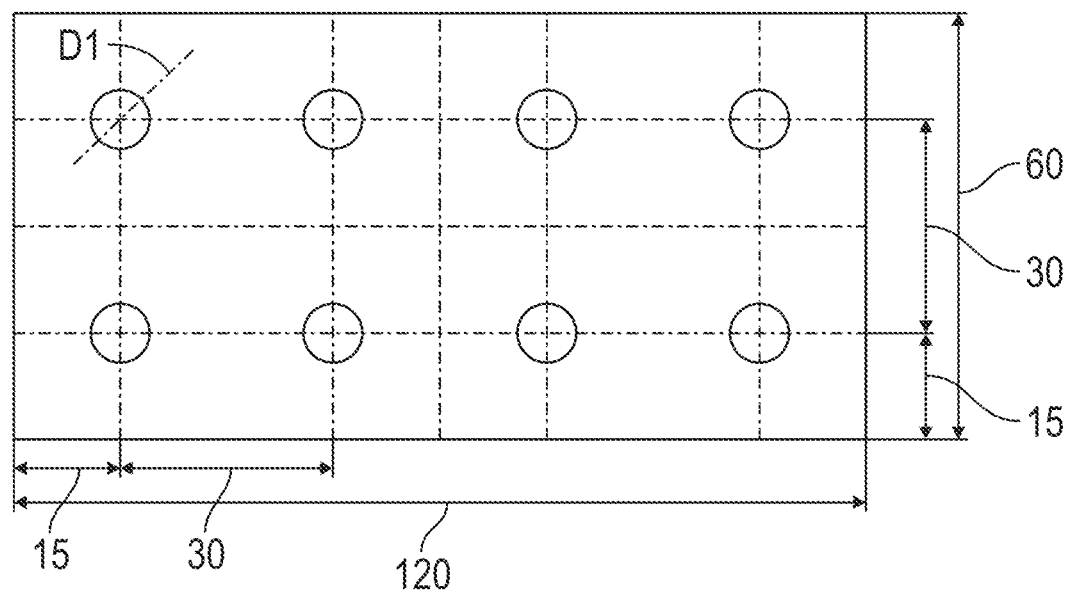
FIG. 5A
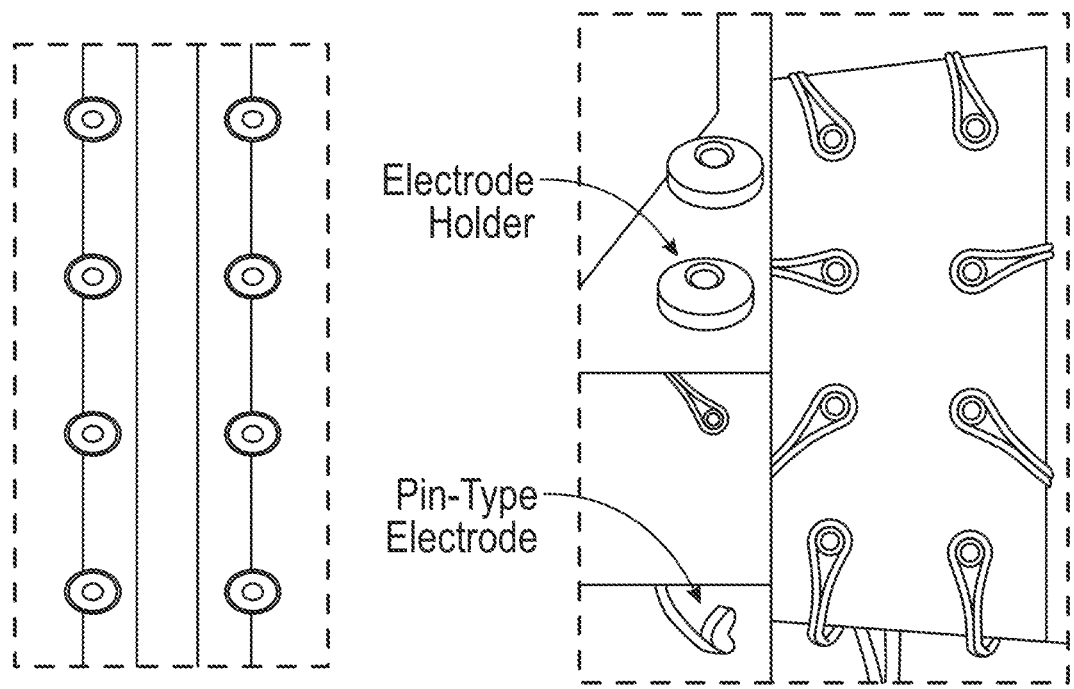
FIG. 5B
FIG. 5C

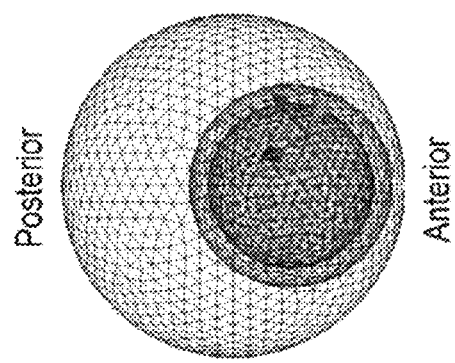

FIG. 19A

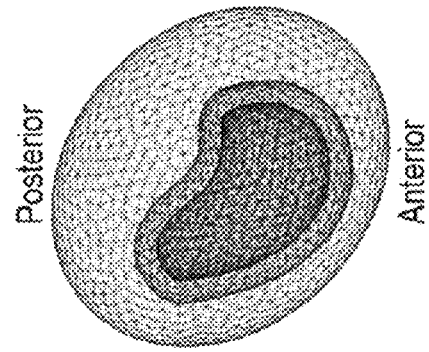

FIG. 19B

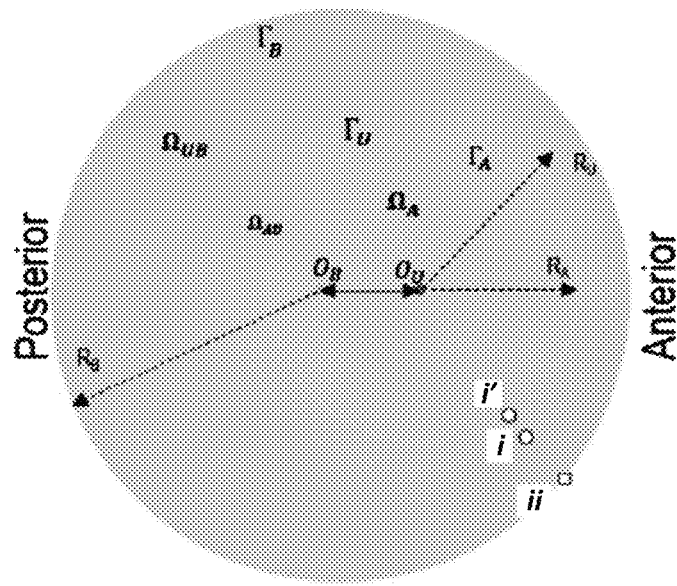

| | |
|---|---|
| $R_B, R_U, R_A$ | Radius of $\Gamma_B, \Gamma_U, \Gamma_A$ |
| $\Gamma_B, \Gamma_U, \Gamma_A$ | Body, uterine, and intrauterine surface, respectively |
| $\Omega_{UB}$ | 3D volume between uterine surface and torso surface |
| $\Omega_{AU}$ | 3D volume between internal uterine surface and uterine surface |
| $\Omega_A$ | 3D volume of internal uterus filled with amniotic fluid |
| ◇ | Torso surface point |
| ○ | Uterine surface point |

FIG. 19C

SYSTEMS AND METHODS FOR ELECTROMYOMETRIAL IMAGING

CROSS-REFERENCE TO RELATED APPLICATIONS

This application claims priority from U.S. Provisional Application Ser. No. 62/963,984 filed on Jan. 21, 2020, which is incorporated herein by reference in its entirety.

FIELD OF THE DISCLOSURE

The present disclosure generally relates to methods of monitoring uterine contractions in a subject non-invasively.

BACKGROUND OF THE DISCLOSURE

Uterine contractions and cervical ripening are essential processes of labor that are influenced by multiple factors, including increased estrogens, increased contractile-associated proteins, and uterine stretch. Clinical management of labor is important for maternal and fetal safety, especially for those patients with arrested labor or spontaneous preterm birth. About 47% of worldwide cesarean deliveries were due to either inadequate uterine contractions or lack of cervix progression. Preterm birth, with a rate of 10.6% globally and 11.2% in North America, may result in a high risk of chronic disorders and is a leading cause of mortality before the age of five years. Current clinical management of labor typically relies on the observation of the uterine contraction using tocodynamometers (TOCO) or intrauterine pressure catheter (IUPC), leading to misdiagnosis of preterm birth in about 50% of patients, resulting in overtreatment, non-necessary hospitalization, and/or questionable identification of labor arrest. Although electromyography (EMG) has demonstrated some feasibility in distinguishing preterm birth or dysfunction contractions based on the features of EMG signals measured on the body surface, knowledge remains limited as to where the uterine contraction initiates, how contractions propagate, and which type of uterine contraction leads to preterm birth or dysfunction.

As a conventional electrophysiological recording technique, Electromyography (EMG), has been developed for decades to measure the bioelectrical signals generated by myometrium during uterine contraction on the abdominal surface. Compared to Tocodynanometer (TOCO), EMG has improved capability to predict the onset of labor in preterm birth based on the magnitude, frequency, and propagation features of the electrical bursts. However, conventional EMG only covers a small region on the abdominal surface with a limited number of electrodes (two and four at the center abdominal surface, and sixty-four at the lower abdominal surface), and body surface measurements of EMG only reflect the averaged electrical activities from the entire uterus. Therefore, conventional EMG techniques cannot detect the detailed electrical initiation and activation patterns on the uterine surface during contractions, limiting its usage in studying the mechanism of parturition.

Current clinical and research devices assessing uterine contractions, such as TOCO, IUPC, and EMG measure an averaged global feature of the uterine contractions and currently lack the ability to specifically characterize the spatial changes of the uterine contraction. However, tissue remodeling, hormone regulation, and fetal-maternal interactions have heterogeneous spatial distributions over the 3-dimensional (3D) uterine myometrial smooth muscle anatomy.

To address the limitation of conventional EMG techniques, a new 3D imaging technique, electromyometrial imaging (EMMI), was recently developed to non-invasively image the electrical activation sequence of myometrium during uterine contractions. EMMI measures a detailed body surface bioelectricity map with up to 200 electrodes around the abdominal surface and the lower back surface. In addition, EMMI conducts a magnetic resonance imaging (MRI) scan to generate the subject-specific body-uterus geometry. By combining the body-uterus geometry and the body surface bioelectricity measurements, EMMI can non-invasively image the electrical activation features of the uterine contractions on the uterine surface. EMMI can accurately localize the initiation of the uterine contraction and image the entire propagation patterns during the uterine contractions in 3D. The procedures of EMMI in clinical settings and representative results obtained from pregnant women are disclosed herein.

Electromyometrial imaging (EMMI) non-invasively images the electrical properties of uterine contractions with high spatial and temporal resolution over the entire 3D uterine surface. A translational sheep model previously demonstrated the feasibility and accuracy of EMMI by comparing the EMMI-imaged uterine electrical signals with directly measured electrical signals on the uterine surface. Additional experiment-simulation studies have demonstrated that EMMI works well under different geometry deformations and noise contaminations.

SUMMARY OF THE DISCLOSURE

In one aspect, a system for monitoring uterine contractions in a subject is disclosed. The system includes at least one electrode patch and a computing device operatively coupled to a plurality of electrodes of the at least one electrode patch. Each electrode patch includes an adhesive flexible membrane and the plurality of electrodes affixed to the flexible membrane. The plurality of electrodes extend through the flexible membrane in an array pattern. The at least one electrode patch is configured to adhere to a body surface overlying a uterus of the subject. The computing device includes at least one processor and a non-volatile computer-readable media containing instructions executable on the at least one processor to: receive a body-uterus geometry of the subject, receive a plurality of EMG signals from the plurality of electrodes; and transform the plurality of EMG signals into at least one uterine potential map based on the body-uterus geometry of the subject. The body-uterus geometry includes the 3D positions of a uterus surface and the body surface of the subject, and each 3D position of each electrode on the body surface of the subject. In some aspects, the system also includes at least one MRI marker patch with an adhesive flexible membrane and a plurality of MRI markers affixed to the flexible membrane in an MRI marker pattern matched to the array pattern of the plurality of electrodes of the electrode patch. Each of the at least one MRI marker patches is configured to adhere to the body surface overlying the uterus of the subject such that each location of each MRI marker is matched to a corresponding location of each electrode when the at least one electrode patch is adhered to the body surface of the subject. In some aspects, the non-volatile computer-readable media further contains instructions executable on the at least one processor to: receive an MRI image of the subject with the at least one MRI marker patch adhered to the body surface of the subject; receive a 3D optical scan of the subject with the at least one electrode patch adhered to the body surface of the subject; and register the MRI image with the 3D optical scan to produce the body-uterus geometry. In some aspects, the non-volatile computer-readable media further contains instructions executable on the at least one processor to transform the at least one uterine potential map into at least one uterine electrogram, at least one isochrone map, and any combination thereof. In some aspects, the non-volatile computer-readable media further contains instructions executable on the at least one processor to transform the at least at least one isochrone map into at least one summary parameter selected from activation ratio, activation duration, synchronized ratio, slow conduction ratio, median propagation speed, and any combination thereof. In some aspects, the system further includes an optical 3D scanner operatively coupled to the computing device that is configured to obtain the 3D optical scan of the subject with the at least one electrode patch adhered to the body surface of the subject. In some aspects, the system further includes an MRI scanner operatively coupled to the computing device that is configured to obtain the MRI image of the subject with the at least one MRI marker patch adhered to the body surface of the subject. In some aspects, the non-volatile computer-readable media further contains instructions executable on the at least one processor to classify the labor status of the subject based on at least one of the at least one uterine potential map, the at least one uterine electrogram, the at least one isochrone map, and the at least one summary parameter. In some aspects, the labor status of the subject is selected from early labor, late labor, preterm birth, and labor arrest.

In another aspect, a computer-implemented method for imaging uterine contractions in a subject is disclosed. The method includes: receiving a body surface potential map $\Phi_B$ that includes electrical potential values measured at a plurality of surface electrode locations, as well as a body-uterus geometry G corresponding to the subject. The method also includes transforming the body-uterus geometry G into U, Σ, and X using a single value composition method, wherein U is a matrix of singular vectors spanning the body surface, Σ is a diagonal matrix of singular values ($\sigma_1$, $\sigma_i$, ... $\sigma_Z$), X is a matrix of singular vectors spanning the uterine surface, M is the number of body surface sites, N is the number of uterine sites and Z=min(M,N). The method also includes transforming the body surface potential map $\Phi_B$ and the body-uterus geometry G into a plurality of spatial dependent (SP) regularization factors $\lambda_{SP}=[\lambda_1, \lambda_1, \ldots \lambda_k, \lambda_N]$ using the function $f(G, \Phi_B)$, where $\lambda_k$ is the regularization factor corresponding to the $k^{th}$ uterine surface position of N total position. The method also includes transforming the body surface potential map $\Phi_B$ into the uterine surface potential map $\Phi_U$ according to $$\Phi_U = \sum_{i=1}^{Z} \frac{\sigma_i^2}{\sigma_i^2 + \lambda_k} \frac{d_i}{\sigma_i} X_{k,i};$$

where $d_i$ is a decomposition of the body surface potential $\Phi_B$ onto the $i^{th}$ singular vector of U, according to $d_i=U^T_i\Phi_B$. The method also includes displaying, using the computing device, the uterine surface potential map $\Phi_U$ representative of the uterine contractions in the subject.

In another aspect, a method for imaging uterine contractions in a patient is disclosed. The method includes providing an atlas that includes a reference body surface-uterus geometry, positioning a plurality of sensors on a body surface of the patient, obtaining a plurality of patient-specific sensor positions corresponding to the plurality of sensors using a 3D optical scanner, transforming the plurality of patient-specific sensor positions to a patient-specific body surface-uterus geometry by projecting the plurality of sensor positions onto the reference body-uterus geometry of the atlas, obtaining a plurality of EMMI signals using the plurality of sensors; and reconstructing a plurality of uterine electrical signals based on the plurality of EMMI signals and the patient-specific body surface-uterus geometry.

Other objects and features of the disclosure will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 5A is a top-view drawing of an electrode patch in accordance with one aspect of the disclosure.

FIG. 5B is a top-view image of an MRI-compatible marker patch in accordance with one aspect of the disclosure.

FIG. 5C contains top-view images of an electrode holder, pin-type electrode, and electrode patch in accordance with one aspect of the disclosure.

FIG. 19A is a schematic diagram illustrating a three-layer spherical simulation geometry in right lateral view, representing three volume conductors, $\Omega_{UB}$, $\Omega_{AU}$, and $\Omega_A$. Arrows represent the dipole directions: normal direction (green arrow), and two tangent directions (red and blue).

FIG. 19B is a schematic diagram illustrating a three-layer RPI geometry in right lateral view.

FIG. 19C is a schematic diagram showing a bio-electricity simulation setting in right lateral view. $O_B$ and $O_U$ represent the centers of the body surface and uterine surface, respectively. $R_B$, $R_U$, and $R_A$ represent the radius of the three spherical geometries. A dipole was placed on the intrauterine surface, $\Gamma_A$. The body surface point C is nearest to uterine point A.

Figure 1:
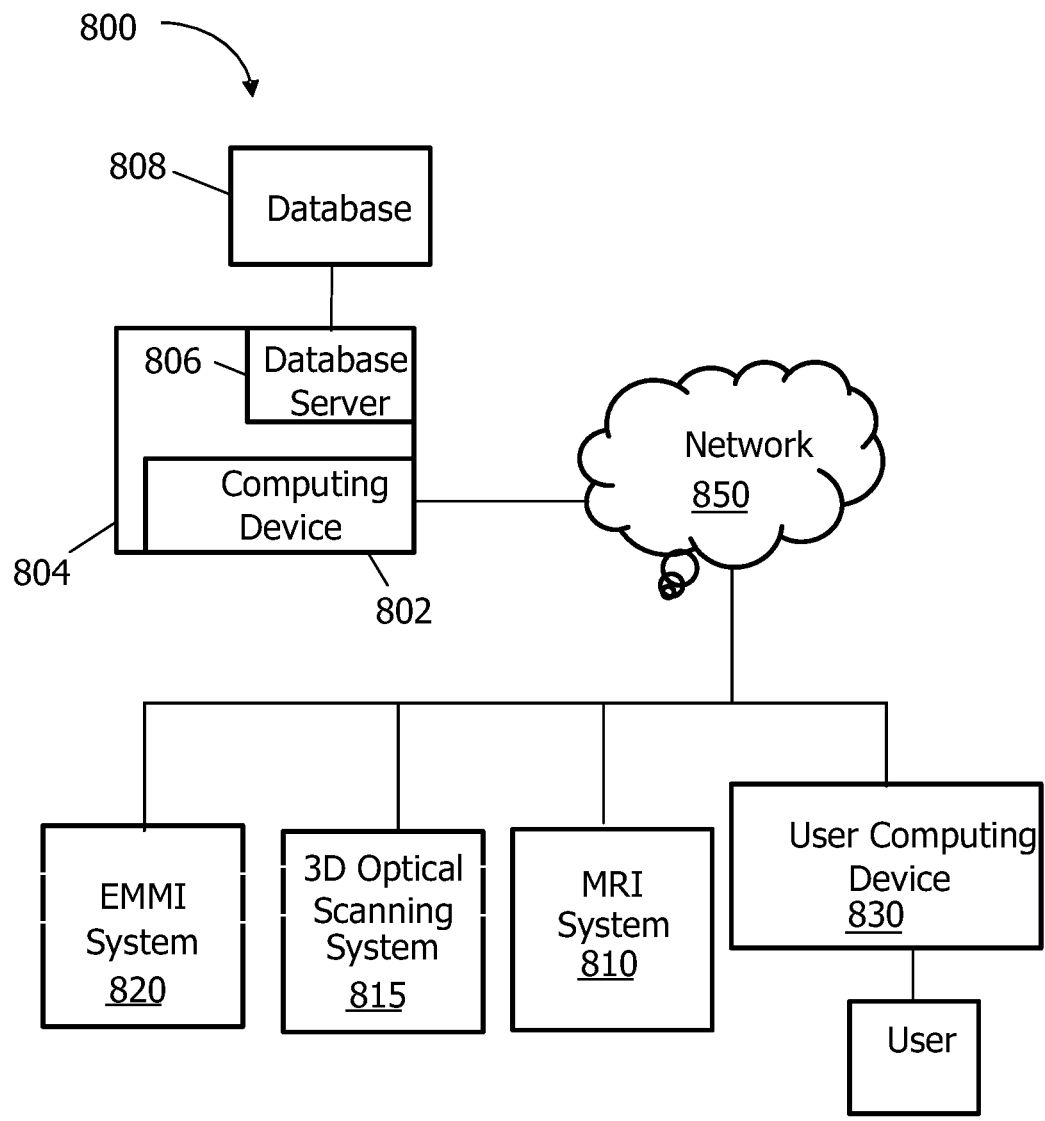
FIG. 1 is a block diagram schematically illustrating a system in accordance with one aspect of the disclosure.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE DISCLOSURE

In various aspects, devices, systems, and methods of noninvasively imaging three-dimensional uterine electrical features underlying uterine contractions in nulliparous pregnant women, including electrical potentials, electrograms, and isochrone maps using electromyometrial imaging (EMMI) are disclosed. EMMI noninvasively images uterine activation patterns, locates early active uterine regions, and analyzes electrical activation features of uterine regions clinically during active labor. In some aspects, EMMI may be employed to study the electrophysiology underlying uterine contractions during normal labor and to investigate pathological uterine contractions for better diagnosis and management of dysfunctional labor.

Management of labor is clinically important to ensure fetal health and maternal safety for normal labor, preterm labor, and labor dysfunction. Timely well-functioned uterine contractions to expel the fetus are critically important. However, there is still limited knowledge of how the myometrium transitions from quiescent to active, and how contractions initiate and propagate during labor. In various aspects, the development and application of an imaging modality, electromyometrial imaging (EMMI) are disclosed herein. As described in additional detail below, EMMI is capable of imaging and quantifying the three-dimensional uterine contraction patterns noninvasively in pregnant women. EMMI has been demonstrated to reliably image uterine surface electrical activities across different contractions and patients, and the dynamic nature of uterine contractions may be quantified using one or more EMMI-imaged parameters including, but not limited to, activation duration, synchronization ratio, slow conduction ratio, and median speed. As demonstrated in the examples below, early activation regions selected based on analysis of EMMI data were demonstrated to be significantly different from corresponding late activation regions. In various aspects, EMMI accurately images three-dimensional uterine activation patterns underlying uterine contractions noninvasively for pregnant women.

Although electromyography has been used preclinically to demonstrate that frequency and magnitude of the electrical signal change over the course of gestation, presumably enabling contractions that change the cervix at term and result in delivery, it lacks sufficient three-dimensional and regional spatial resolution to fully understand the electrical maturation of the uterus over gestation. A similar challenge in cardiovascular imaging was overcome using electrocardiographic imaging (ECGI) to image the electrical activation of the heart with remarkable local accuracy. ECGI has been used for patients with normal and diseased hearts and offers an advanced level of precise imaging, comparable to direct bioelectrical mapping, without being invasive. Instead of heartbeats, EMMI was developed to image uterine contractions based on the success of ECGI, allowing a more complete understanding of the electrical initiation and propagation of contractions by tracking the electrical signal across the entire uterus.

Electromyometrial imaging (EMMI) was originally developed and validated to noninvasively image uterine contractions using a translational sheep model. Based on the sheep EMMI results, human EMMI systems and methodologies were developed to enable its clinical applications. As described in the examples below, hardware and software were developed for human EMMI systems, including human electrode mapping systems and methods for extracting physiological/pathological information from EMMI data.

In various aspects, the disclosed EMMI systems, devices, and methods include at least several features incorporated to overcome limitations of existing systems and devices for monitoring uterine contractions. In some aspects, the disclosed EMMI device makes use of a modular and flexible electrode patch design for placement of the EMMI electrodes described below. The disclosed patch design accommodates the large curvature of patient abdominal surfaces, adapts around clinical monitors, and improves electrode contact to the patient's skin.

In other aspects, the disclosed EMMI methods include utilizing a hand-held optical 3D scanner to quantify the positioning of the electrode patches on the patient immediately prior to bioelectricity mapping. Typically, the MRI scan used to obtain the patient's anatomical measurements is scheduled days before the patient's clinical examination and bioelectricity mapping. The optical scanner acquires accurate body surface geometry with electrode locations on the day of bioelectricity mapping. A registration algorithm registers the optical scanned surface and the MRI scanned surface to generate an accurate body-uterus geometry.

In additional aspects, the disclosed methods include automatic artifacts detection and adaptive inverse algorithms to provide for automatic signal processing and to perform the inverse calculation without the manual segmentation of the signal segments with good quality. These algorithms render the disclosed methods suitable for clinical applications by implementing the pre-processing phase of data analysis without need for expert input or supervision.

In other additional aspects, the disclosed methods include an automatic cluster detection and refinement algorithm to identify EMG bursts in the electrograms and generate quantitative parameters that are well correlated with the human labor progress. Non-limiting examples of suitable quantitative parameters include activation ratio, activation duration, synchronized ratio, slow conduction ratio, and median contraction speed. As demonstrated in the examples below, the disclosed EMMI system noninvasively imaged human uterine contractions and characterized labor progress by quantifying multiple electrophysiological properties of uterine contractions. The human EMMI-derived parameters described above hold great promise to provide novel imaging biomarkers to diagnose preterm birth or labor arrest and to facilitate the development of new treatments.

There is no reliable imaging technique to image the human uterine contractions and diagnose preterm birth and labor arrest. This invention can be readily integrated into the routine of the clinical practice and can generate reliable and accurate images and quantitative parameters to monitor uterine contractions during labor and facilitate labor management.

The disclosed EMMI systems, devices, and methods are easily integrated into the routine of clinical practice and are able to generate reliable and accurate EMMI images. Body surface electrical potential maps on both anterior abdomen and low back surfaces can be acquired using the disclosed EMMI system to comprehensively record uterine electrical activation. The disclosed EMMI system noninvasively images the uterine surface potential maps based on measured body surface potentials and patient-specific uterus-body geometry, which enable an overview of the electrical activity of the uterine contractions with high spatial resolution as compared with traditional EMG. In potential maps obtained using the disclosed EMMI system, electrical information is localized on the uterine surface with full coverage and high spatial resolution, which carries rich physiological information. In addition, the activation time at each uterine site during one uterine contraction can be extracted from the uterine surface EMG obtained using the disclosed EMMI system to form a three-dimensional isochrone map, which shows the detailed electrical activation patterns. Therefore, the disclosed EMMI system can provide a new way to investigate normal as well as dysfunctional labor in human patients.

I. EMMI Systems

Figure 17:
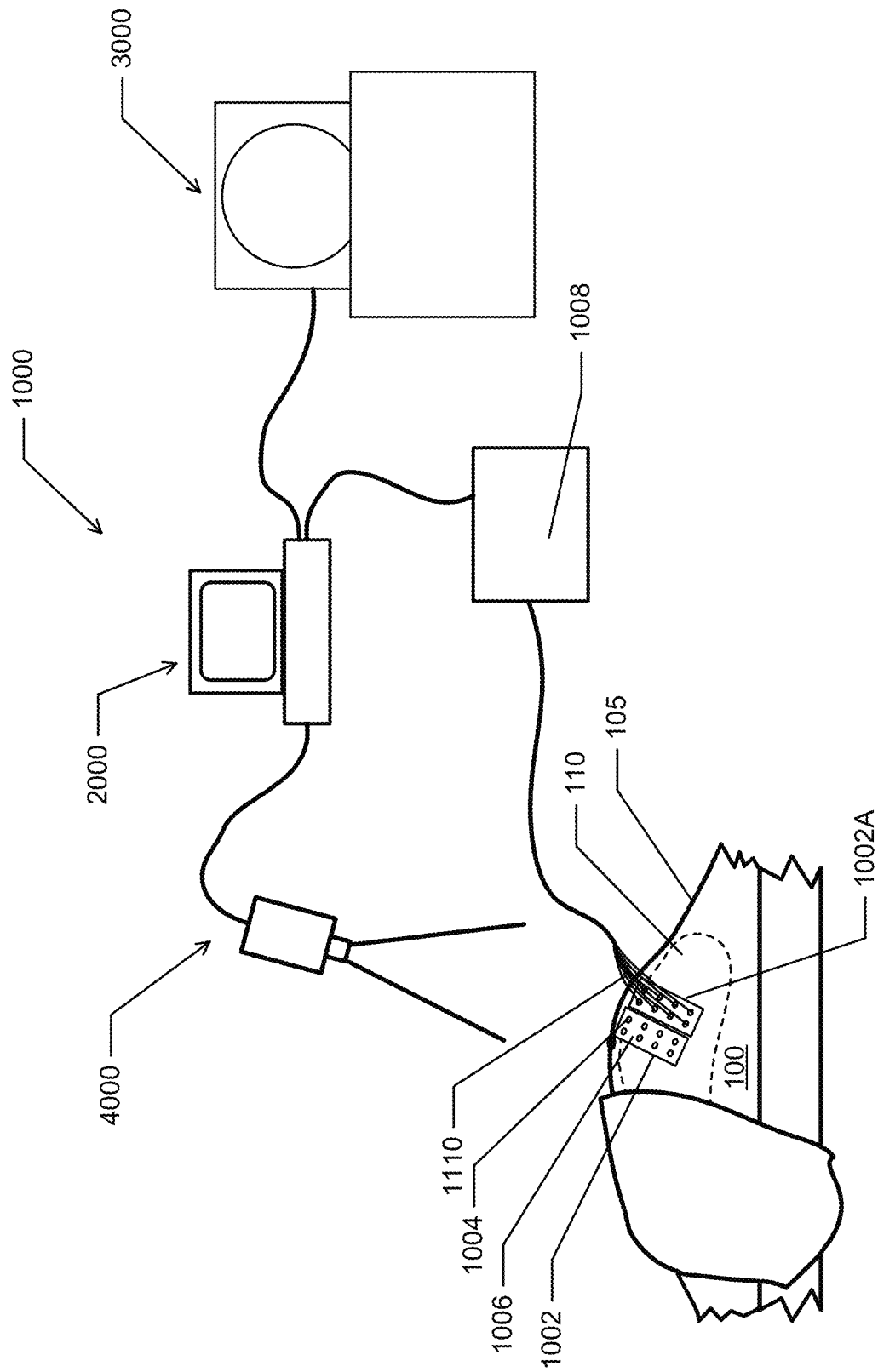
FIG. 17 is a schematic diagram illustrating elements of an EMMI system for monitoring uterine contractions in accordance with an aspect of the disclosure.

In various aspects, the imaging of human uterine contractions using EMMI measurements as described herein may be implemented obtained using an EMMI system. FIG. 17 is a schematic illustration of an EMMI system 1000 in one aspect. In various aspects, the EMMI system 1000 is configured to obtain and analyze electrical signals at a body surface 105 of a subject 100 that are indicative of uterine contractions using the methods described herein. In some aspects, the EMMI system 1000 may include a computing device 2000 configured to receive and analyze the electrical measurements to produce electrograms and isochrone maps as described herein. The computing device is described in additional detail below.

In other additional aspects, the EMMI system 1000 may further include an MRI scanner 3000 operatively coupled to the computing device 2000. The MRI scanner 3000 is configured to obtain an MRI image of the subject including the body surface, surface electrode locations, and uterus surface used to define the body-uterine geometry in accordance with the methods described herein. In various other aspects, the EMMI system 1000 may further include an optical 3D scanner 4000 operatively coupled to the computing device 2000. The optical 3D scanner 4000 is configured to obtain a 3D optical scan of the subject including the body surface and surface electrode locations used in combination with the MRI image to define the body-uterine geometry in accordance with the methods described herein.

In some aspects, the EMMI system 1000 includes at least one electrode patch 1002 configured to adhere to the body surface 105 of a subject 100. In one aspect, the at least one electrode patch 1002 is configured to be adhered to a region of the body surface 105 overlying the uterus 110 of the subject 100. In various aspects, the electrode patch 1002 includes a plurality of electrodes 1004 used to obtain surface electrical measurements as described in detail in the examples below. In some aspects, the plurality of electrodes of the electrode patch 1002 are mounted within a flexible adhesive membrane 1006 configured to conform to the contour of the subject's body surface 1005 and to position each electrode 1004 in electrical contact with the body surface 105 in a repeatable manner, as described herein. In other embodiments, each electrode patch 1002 contains a portion of the electrodes 1004 needed to perform EMMI mapping of uterine contractions, so that multiple electrode patches 1002, 1002A may be used to position a sufficient number of electrodes 1004 to implement EMMI imaging and mapping of uterine contractions as described herein. In various aspects, each electrode patch 1002 may contain any number of electrodes 1004 without limitation including, but not limited to, 1 electrode, 2 electrodes, 3 electrodes, 4 electrodes, 5 electrodes, 6 electrodes, 7 electrodes, 8 electrodes, 9 electrodes, 10 electrodes, or more.

FIG. 5A is a photograph of a template for an electrode patch in one aspect showing the arrangement and spacing of the electrodes within the flexible sheet. FIG. 5C is a photograph showing an electrode patch in another aspect. As illustrated in FIG. 5C, the electrode patch includes a plurality of electrode holders in some aspects. Each electrode holder defines a reinforced opening configured to receive an electrode including, but not limited to, a pin-type electrode configured to obtain electrical measurements on the body surface of the subject as described herein.

Referring again to FIG. 17, each electrode 1004 in the electrode patch 1002 may be operatively coupled to various data acquisition and signal processing electronics 1008 configured to receive, record, and/or process electrical signals from the electrodes 1004. The electrodes 1004 may be operatively coupled to the electronics using any suitable means without limitation including, but not limited to, cables 1110 as illustrated in FIG. 17.

Figure 5D:
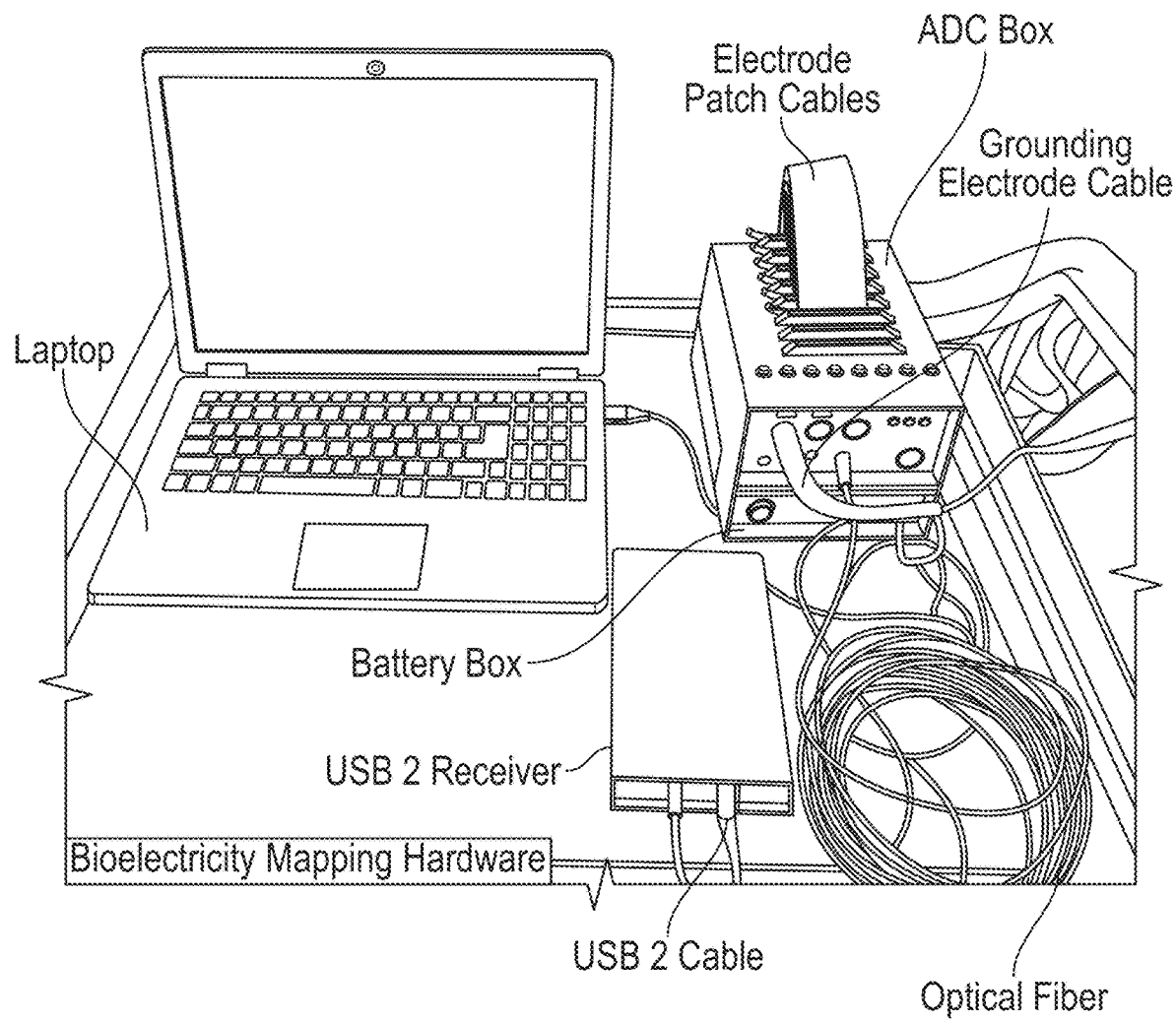
FIG. 5D is an image illustrating elements of the bioelectricity mapping hardware operatively connected to the electrode patch to form the EMMI system.

FIG. 5D is an image showing the components of an EMMI system in one aspect. As shown in FIG. 5D, the EMMI system may include electrode patch cables including, but not limited to, ribbon cables as illustrated in FIG. 5D that are operatively coupled to the electrodes of an electrode patch at one end to an ADC device at an opposite end. In some aspects, the ADC device may be operatively coupled to a grounding electrode cable to enhance the quality of the electrical signals obtained from the electrode patches via the electrode patch cables.

Referring again to FIG. 5D, the EMMI system may further include a receiver operatively coupled to the ADC box and to the computing device in some aspects. The receiver may be any suitable device configured to receive and/or store the digitized electrical signals from the ADC device including, but not limited to, the USB2 receiver shown illustrated in FIG. 5D.

Referring again to FIG. 17, the MRI scanner 3000 of the EMMI system 1000 is configured to obtain MRI data defining the uterine surface and the body surface with electrode positions. Any MRI scanner suitable for obtaining structural MR images of the subject's body surface and uterus at sufficiently high resolution for EMMI mapping may be used without limitation. In some aspects, the MRI image is obtained from the subject with MRI patches applied in essentially identical positions to the corresponding positions of the electrode patches during EMMI electrical measurements. In some aspects, the MRI patch has essentially the same dimensions and electrode positions as the corresponding electrode patch, for example as illustrated in FIG. 5A. By way of non-limiting example, FIG. 5B show an MRI patch in one aspect. In various aspects, the MRI patch includes a flexible adhesive membrane that is essentially transparent to MR imaging as well as MRI markers positioned in an arrangement corresponding to the arrangements of the electrodes on the electrode patch. Any suitable high-contrast material may be used to form the MRI markers of the MRI patch including, but not limited to, Vitamin E liquid softgels.

Additional descriptions of the elements of the EMMI system and associated methods of measuring and mapping uterine contractions are provided in additional detail below.

As described in the examples below, isochrone maps of three patients with different cervix dilations obtained using the disclosed EMMI system (FIGS. 11A, 11B, and 11C, respectively) indicated that the region of activated uterine muscle (activation ratio, FIG. 12A) enlarged as the cervix dilation increased across all patients. Without being limited to any particular theory, the increased activation ratio as uterine dilation increased may represent an increase of uterine myometrium cells that were recruited and contributed to the measured uterine contraction. Typically, cervical dilation is used clinically to indicate labor progression, but previously published data reported large variances of cervix dilation speed in normal term labors, and in particular cervix dilation speed is much slower before cervix dilation reaches 5 cm in both nulliparous and multiparous women. By contrast, the results of these experiments may indicate that the uterine activation ratio may serve as a more consistent clinical indicator of labor progression. As indicated in FIG. 12A, a low uterine activation ratio is observed at the early labor stage (Case 1, 5 cm cervix dilation) which may generate a small mechanical load onto the cervix and result in the slow cervix remodeling and dilation; uterine activation ratio increased at later labor stages (Cases 2 and 3, 7 and 8 cm cervix dilation, respectively). EMMI imaged uterine activation ratio may provide important patient-specific information about uterine contraction to at least partially explain the large patient variance in cervix dilation speed. Moreover, EMMI imaged uterine activation ratio and clinically measured cervix dilation may carry complementary information to better characterize labor progression in both individual patients and within groups of patients.

Figure 12A:
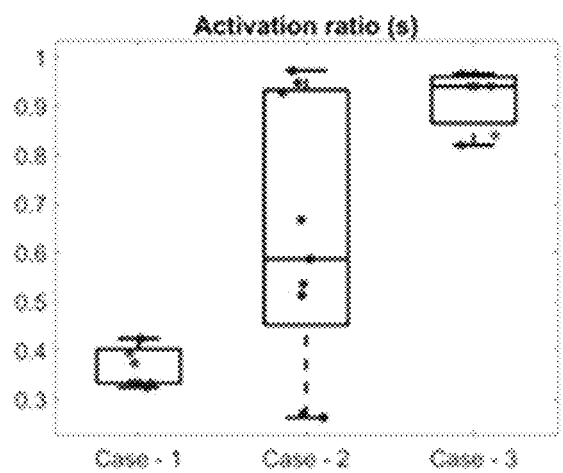
FIG. 12A is a graph summarizing activation ratios of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.

Without being limited to any particular theory, the isochrone-derived indices obtained noninvasively using the disclosed EMMI systems and methods may serve as surrogate markers indicative of myometrium remodeling and maturation. With the progression of labor, the increase of a major myometrial gap junction connexin43 (Cx43) results in increased connectivity of the myometrial cells, which enables extensive propagation of the depolarization in individual myometrial cells. As illustrated in the examples below, a smaller slow conduction ratio (FIG. 12D), lower synchronized ratio (FIG. 12C), and larger median speed (FIG. 12E) were observed for the patient of case #3 whose cervix dilation was around 8 cm and time to deliver was around 1.5 h. The spatial information contained within uterine surface potential maps obtained using the disclosed EMMI system (see FIG. 10C) can locate slow conduction regions and/or fast propagation regions that may help to diagnose and locate underdeveloped or otherwise abnormal regions of the uterine muscle. The disclosed EMMI systems, devices, and methods are a promising imaging technique to study the mechanism of parturition and may serve as a diagnostic method of identifying the risk of preterm birth in a subject.

However, a larger group of subjects will be required to perform systematic analysis and application of EMMI. The significant limitation of EMMI is the requirement of an MRI scan, which makes it hard to acquire real-time imaging and limits the application due to the high cost of MRI scans. A cheap and convenient tool should be considered for future development, such as 3D ultrasound imaging. The other limitation is that placement of a large number of electrode patches, multi-sensor recordings, and post-processing requires a well-trained team, which may prevent its application in clinical settings. An integrated, easy-to-place, electrode layout and further developed post-processing software are necessary for future applications.

There are several steps in performing EMMI in pregnant women to assure accurate EMG signal quality. First, MRI images are obtained from patients wearing patches representative of the planned placement of the EMG electrodes based on the MRI images. Following the rules of placement (see the protocol) is critical to reduce the electrode location errors. Second, the proper amount of gel and the good contact between electrodes and the skin are needed to guarantee good EMG signal quality. Third, repeated optical scans may be needed to make sure high-quality body surface geometry can be obtained.

MRI is an expensive step in EMMI protocol and a limiting factor for its wide clinical translation because it is challenging for women to undergo MRI scans after the labor starts. As a compromise, an MRI scan is currently conducted at an earlier day before the electrical mapping during labor. Therefore a future improvement to EMMI protocol will be employed clinical ultrasound to acquire subject-specific body-uterus geometry at a patient's bedside. This will not only reduce the overall cost of EMMI but also enable a real-time measurement of geometry possibly during electrical recording. Another potential enhancement to EMMI protocol is to incorporate wearable, disposable printed electrodes that can be mounted on an elastic material. This will reduce the cost of the electrode and significantly improve the comfort of applying and wearing a large number of electrodes during labor.

II. FMMI Methods

Figure 16:
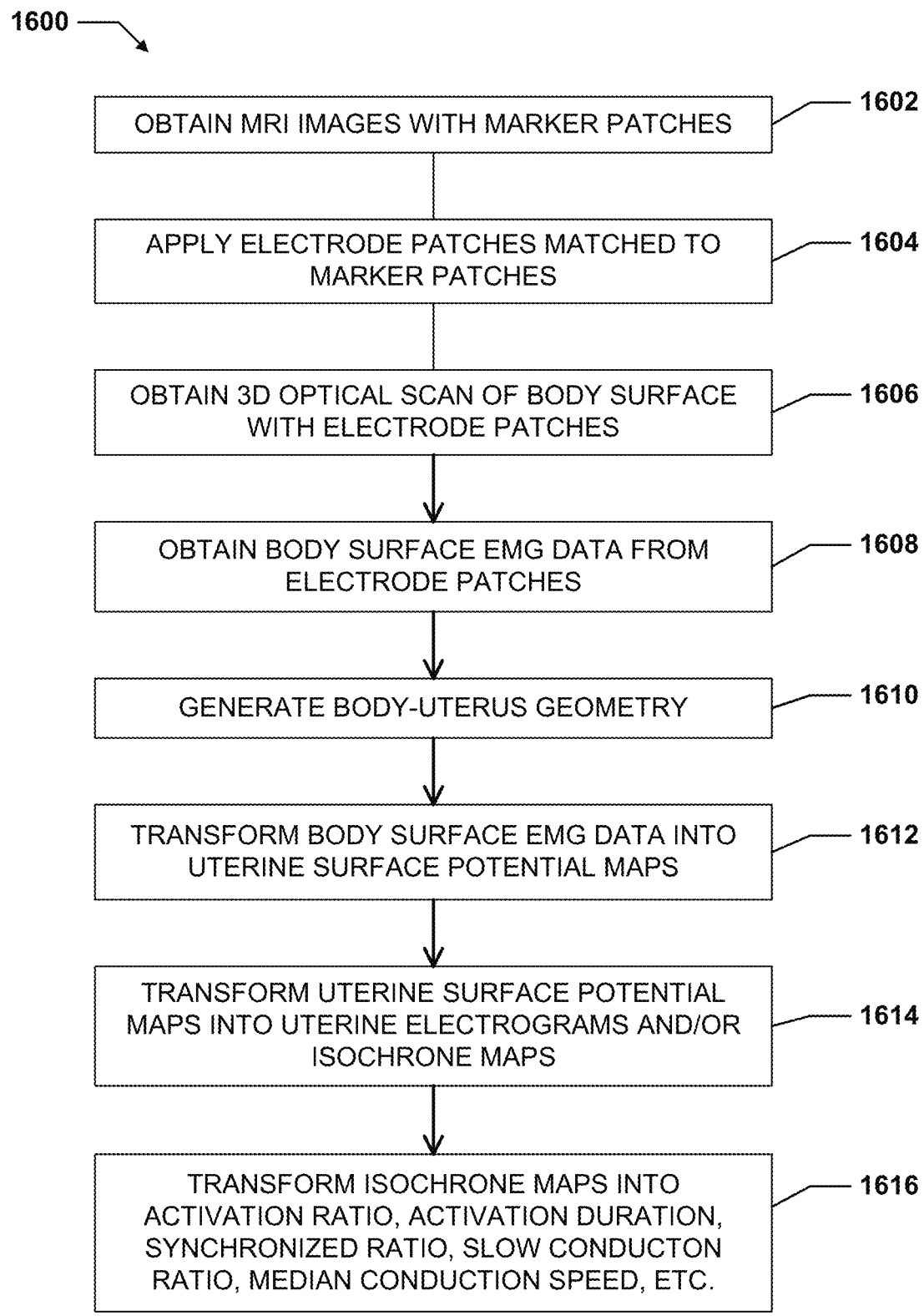
FIG. 16 is a flow chart illustrating a method of monitoring uterine contractions using the EMMI system in accordance with an aspect of the disclosure.

By way of non-limiting example, FIG. 16 is a block diagram illustrating the steps of a method 1600 of monitoring and mapping uterine contractions using the EMMI system in various aspects. The method 1600 may include obtaining MRI images of the subject with MRI patches at 1602. In some aspects, the MRI patches may be any MRI patch that includes MRI markers positioned similarly to the placement of the electrodes in the electrode patches including, but not limited to, the MRI patch illustrated in FIG. 5B.

Any suitable MRI device and MR sequence configured to obtain an MR image at a resolution suitable for EMMI mapping may be used to obtain MRI data without limitation. By way of non-limiting example. the MRI scanner may be a 3T Siemens Prisma/Vida with a radial volume interpolated breath-hold examination fast T1-weighted sequence.

Referring again to FIG. 16, the method 1600 further includes applying electrode patches to the subject at 1604 such that the electrodes are positioned in similar positions to the MRI markers of the MRI patch. In some aspects, the electrode patches and MRI patches are essentially identically sized with essentially identical positioning of electrodes and MRI markers, respectively. By way of non-limiting example, the MRI patch (FIG. 5B) and electrode patch (FIG. 5C) may be produced using the same template (FIG. 5A). In other aspects, the MRI and electrode patches may be positioned according to a standard protocol using landmark anatomical features of the subject including, but not limited to, the spine, the top of the buttock cleavage, the iliac crest, the abdominal midline, the naval, and any other suitable anatomical feature of the subject. In these other aspects, rulers or other templates may be positioned on the subject's body surface to facilitate consistent placement of the MRI and electrode patches. In other aspects, a practitioner may take notes and/or images including, but not limited to, photographic images, to memorialize the positioning of the MRI and electrode patches.

Referring again to FIG. 16, the method 1600 may further include obtaining an optical 3D scan of the subject after placement of the electrode patches at 1608. Any suitable 3D optical scanning device capable of obtaining 3D optical scans of the subject and electrodes at suitable resolution for EMMI mapping may be used without limitation. Non-limiting examples of suitable 3D optical scanners include hand-held scanners. In one non-limiting example, the 3D optical scanner makes use of structured white light (Artec 3D, Luxembourg) to ensure the safety of the subject.

Referring again to FIG. 16, the method 1600 further includes obtaining body surface EMG data from the surface electrode patches. In various aspects, any suitable devices and elements may be used to obtain the EMG data without limitation. By way of non-limiting example, the electrodes of the electrode patches may be operatively coupled to an ADC box to digitize the electrode readings as illustrated in FIG. 5D. The digitized electrode readings may be received and/or stored at a receiver operatively coupled to the ADC box, and a computing device operatively coupled to the receiver may access the digitized signals for further analysis as described below.

The method 1600 further includes generating a body-uterus geometry at 1610. In various aspects, the body-surface geometry is generated by segmenting the body surface and uterine surface from the MRI data obtained at 1602 and registering the MRI body surface with the optical 3D scanned body surface obtained at 1606 in accordance with the methods described herein. In some aspects, the 3D optical body surface may be registered to the MRI body surface using a two-step process that includes a rigid alignment followed by a non-rigid alignment. One non-limiting example of registering the optical 3D scanned body surface to the MRI body surface is illustrated in FIG. 14.

Figure 14:
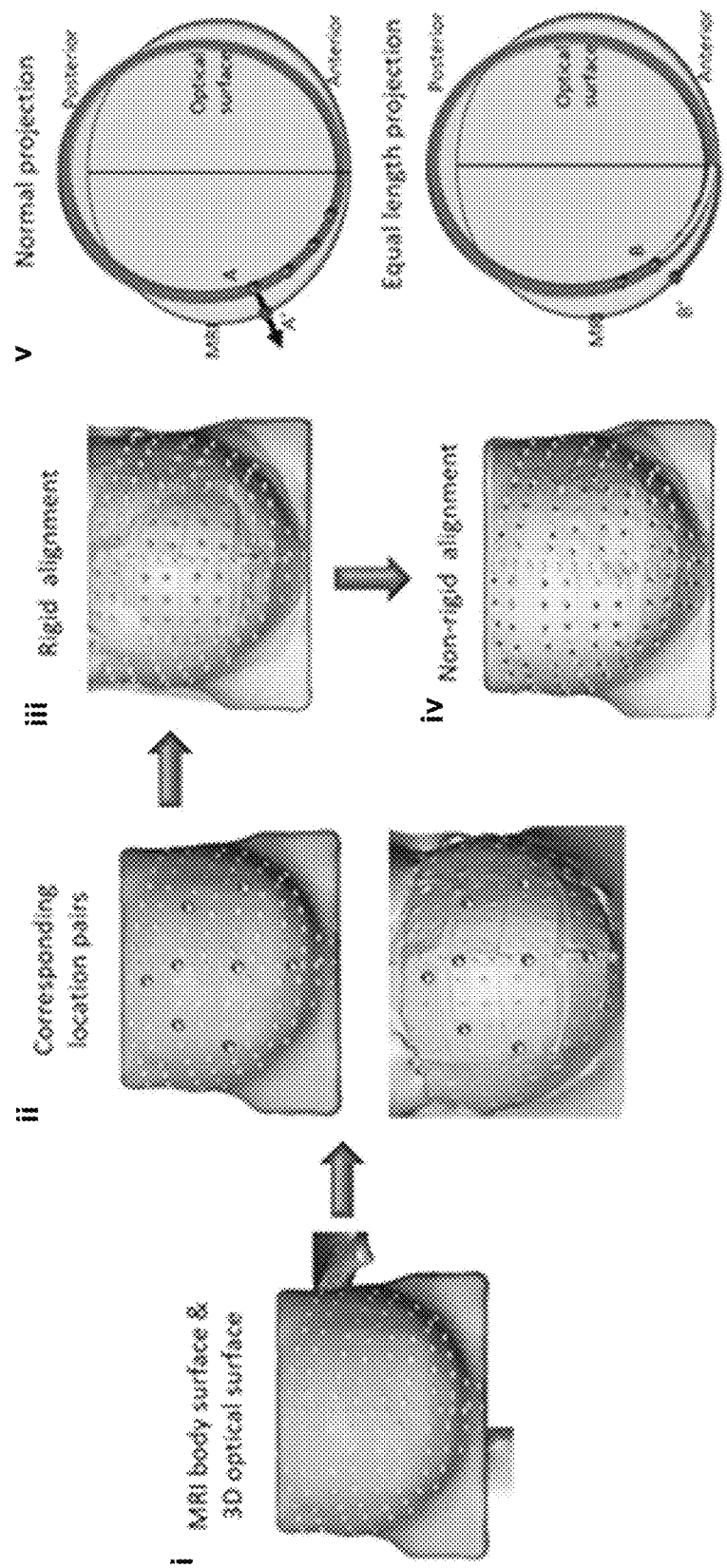
FIG. 14 is a schematic diagram illustrating steps in a method of registering 3D optically-scanned body surface contours to MRI anatomical maps.

As illustrated in FIG. 14, a least-squares rigid alignment may be implemented using a plurality of corresponding location pairs on the 3D scanned body surface and the MRI body surface (see step i). In various aspects, the location pairs are manually selected by a practitioner at step ii. Any suitable number of corresponding location pairs may be used for the rigid alignment at step iii without limitation. In various aspects, the rigid alignment may use at least 4 location pairs, at least 5 location pairs, at least 6 location pairs, at least 7 location pairs, at least 8 location pairs, at least 9 location pairs, at least 10 location pairs, at least 11 location pairs, at least 12 location pairs, or more. In various other aspects, the rigid alignment may use from about 4 location pairs to about 12 location pairs, from about 4 location pairs to about 10 location pairs, from about 4 location pairs to about 8 location pairs, from about 4 location pairs to about 8 location pairs, and from about 4 location pairs to about 6 location pairs. In one aspect, the rigid alignment may use from about 6 location pairs to about 8 location pairs.

Referring again to FIG. 14, the non-rigid alignment at step iv may be implemented as shown in step v as a normal projection, an equal length projection, and any combination thereof. In some aspects, the normal projection or the equal length projection is selected for portions of the body surfaces to be aligned based on the individual characteristics of the different body surface portions and the effectiveness of each non-rigid alignment method in different situations. By way of non-limiting example, equal length projection may be used for non-rigid alignment of the subject's left anterior surface of left lateral position and the outer anterior surface of the supine position, while normal projection may be used for non-rigid alignment of the subject's right anterior surface of left lateral position, the center anterior surface of the supine position, and the back surface of both positions.

Referring again to FIG. 16, the method 1600 further includes transforming the body-surface EMG measurements obtained at 1608 into a series of uterine surface potential maps at 1612. As used herein, a uterine potential map refers to a spatial distribution of uterine potentials at an instant time on the 3D uterine surface. Any suitable method of transforming the EMG measurements into uterine potential maps may be used without limitation. In one aspect, described in Example 1 below, an inverse computation is used to reconstruct uterine potentials based on the measured body surface potentials and patient-specific body-uterus geometry. In this aspect, the inverse computation is formulated as a Cauchy problem for the Laplace's equation (see Eqn. (1) in Example 1 below) with two boundary conditions (Dirichlet condition, Eqn. (2) and Neumann condition, Eqn. (3) in Example 1 below) on the body surface. The inverse computation method is described in additional detail in Example 1 below. By way of non-limiting example, representative uterine surface potential maps are provided in FIG. 8B.

Referring again to FIG. 16, the method 1600 further includes transforming the uterine surface potential maps obtained at 1612 into uterine electrograms and/or isochrones maps at 1614. As used herein, a uterine electrogram includes a series of potentials with respect to time at a specific uterine site. As used herein, an isochrone map characterizes the sequence of uterine activation derived from the local activation times during an observation window corresponding to a uterine contraction. By way of non-limiting example, representative isochrones maps and corresponding uterine electrograms are provided at FIGS. 5A and 5B, respectively.

Referring again to FIG. 16, the method further includes transforming the isochrones maps obtained at 1614 into at least one summary parameter at 1616. Non-limiting examples of suitable summary parameters include activation ratio, activation duration, synchronized ratio, slow conduction ratio, median propagation speed, and any other suitable summary parameter. As used herein, activation ratio refers to the ratio between the area of the active uterine region and the area of the entire uterine surface. As used herein, the activation duration refers to the time difference between the activation time of the first active uterine site and the activation time of the last active uterine site. As used herein, the synchronized ratio refers to the total number of synchronized pairs (adjacent uterine sites activated within 0.2 s of one another) over the total number of active pairs (all adjacent activated uterine sites). Propagation length, as used herein, refers to the Euclidian distance between two uterine sites in a non-synchronized pair. The propagation speed of non-synchronized pairs, as used herein, refers to the propagation length divided by the activation time difference. The slow conduction ratio, as used herein, refers to the percentage of active pairs with a propagation speed smaller than 1 cm/s. The median conduction speed, as used herein, refers to the median propagation speed of the non-synchronized pairs during an EMG burst.

In various aspects, a spatial-dependent (SP) regularization method is disclosed herein that considers both body-uterus eccentricity and the EMG noise level. As described in the examples below, a spherical model and a realistic geometry model were used to compare the reconstruction accuracy of the SP method to that of the CRESO method and the L-Curve method, another existing EMMI reconstruction method. As described in the examples below, the disclosed SP method reconstructed more accurate electrograms and potential maps than either of the other existing methods, especially in cases of high body-uterus eccentricity and noise contamination. The disclosed SP method significantly improves the accuracy and utility of EMMI, in particular as applied to the imaging of uterine contractions in three dimensions. Moreover, the SP method can be used to improve the accuracy of other electrical imaging modalities, such as electrocardiographic imaging.

Existing imaging systems for assessing uterine contractions during pregnancy lack sufficient accuracy to draw meaningful comparisons between different subjects and/or stages of pregnancy off the same subject. Existing electromyometrial imaging (EMMI) systems noninvasively image uterine activation using conventional regularization methods. This disclosed SP method can improve the EMMI's imaging accuracy, especially at conditions when conventional EMMI generated compromised accuracy.

In various other aspects, an atlas-based electromyometrial imaging (EMMI) technique is described that images uterine contraction patterns noninvasively with sufficient accuracy without using expensive imaging modalities such as MRI. This disclosed technique dramatically reduces the cost of EMMI and makes EMMI much more suitable for use in clinical contexts.

Existing EMMI techniques require a patient-specific body-uterus geometry derived from MRI scans. However, MRI scans are expensive, less accessible by patients in most clinics, and not safe for patients with metal implanted devices. The disclosed atlas-based electromyometrial imaging (EMMI) technique makes use of atlas body-uterus geometry in EMMI to noninvasively image and characterize the properties of electrical uterine contractions with image accuracy sufficient to make meaningful comparisons between subjects and to perform longitudinal monitoring of electrical uterine contractions at various stages of pregnancy of the same subject.

Additional description of various aspects of the method of EMMI mapping and monitoring of the uterine contractions of a subject is provided in additional detail in the Examples below.

III. Computing Systems and Devices

FIG. 1 depicts a simplified block diagram of a system 800 for implementing the methods described herein. As illustrated in FIG. 1, the system 800 may be configured to implement at least a portion of the tasks associated with the disclosed methods. In some aspects, the system 800 may be configured to implement at least a portion of the tasks associated with the disclosed SP method of image reconstruction with spatial-dependent regularization using the system 800 including, but not limited to: operating the EMMI system 820 to obtain a plurality of EMG signals over an array of body surface electrodes and using the computing device 830 to transform the plurality of EMG signals into a map of uterine surface electrical potentials using the disclosed spatial-dependent (SP) method as described herein.

The system 800 may include a computing device 802. In one aspect, the computing device 802 is part of a server system 804, which also includes a database server 806. The computing device 802 is in communication with a database 808 through the database server 806. The computing device 802 is communicably coupled to an MRI system 810 and a user computing device 830 through a network 850. The network 850 may be any network that allows local area or wide area communication between the devices. For example, the network 850 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 830 may be any device capable of accessing the Internet including, but not limited to, a desktop computer, a laptop computer, a personal digital assistant (PDA), a cellular phone, a smartphone, a tablet, a phablet, wearable electronics, smartwatch, or other web-based connectable equipment or mobile devices.

Figure 2:
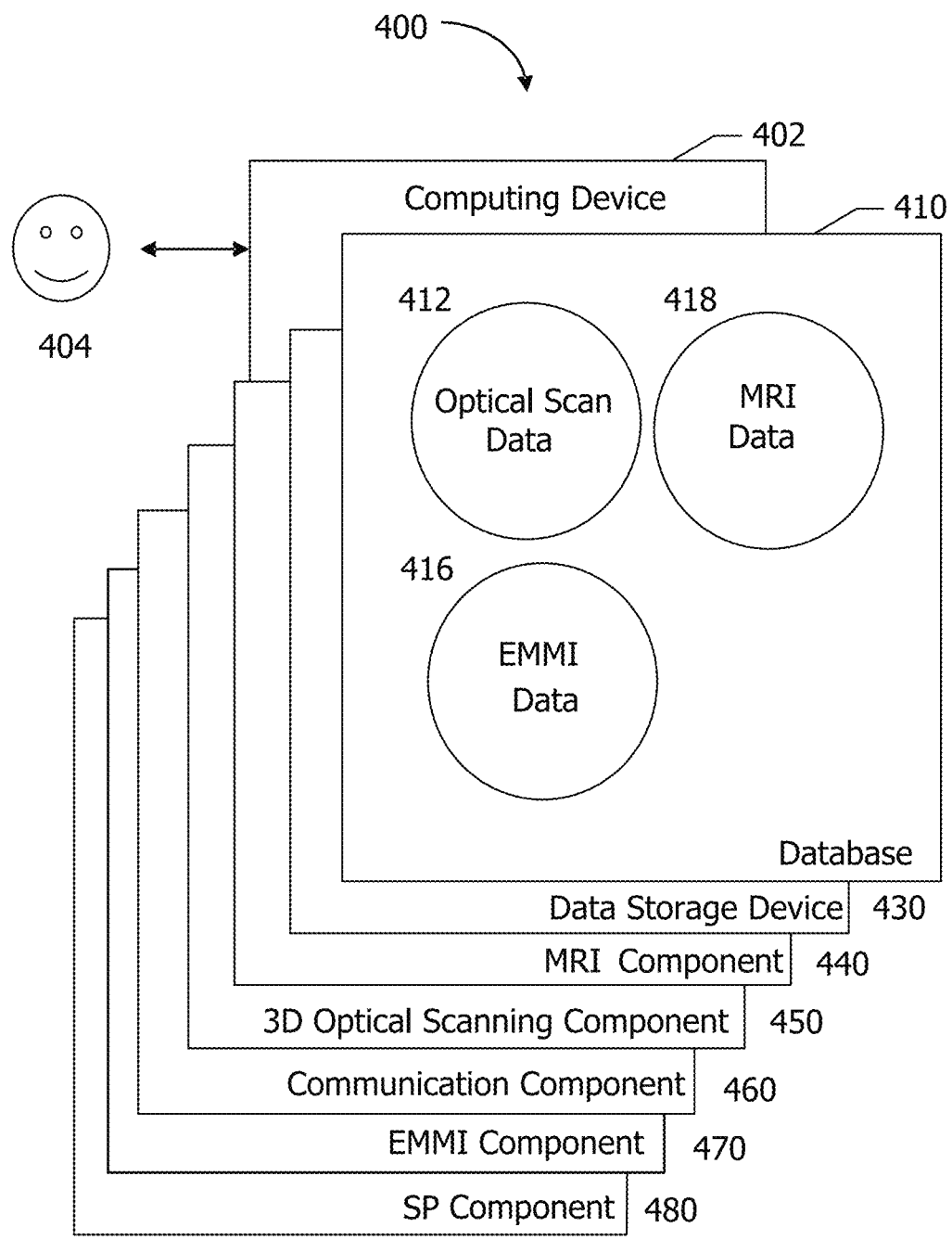
FIG. 2 is a block diagram schematically illustrating a computing device in accordance with one aspect of the disclosure.

In various other aspects, the computing device 802 is also communicably coupled to an MRI system 810 configured to obtain the structural MRI data used to produce MRI-based uterine and body surfaces as described herein. In additional aspects, the computing device 802 is further communicably coupled to an optical 3D scanner 815 used to produce the optically-based body surface as described herein. In other additional aspects, the computing device 802 is further communicably coupled to an EMMI system 820 configured to obtain and analyze EMG measurements as well as to implement electromyometrial imaging as described herein. In some aspects, the MRI system 810 is configured to obtain the structural MRI data used to produce MRI-based uterine and body surfaces as described herein. In additional aspects, the computing device 802 is further communicably coupled to an optical 3D scanner 815 used to produce the optically-based body surface as described herein. In other additional aspects, the computing device 802 is further communicably coupled to an EMMI system 820 configured to obtain and analyze EMG measurements as well as to implement electromyometrial imaging as described herein In other aspects, the computing device 802 is configured to perform a plurality of tasks associated with the method of reconstructing a map of uterine surface electrical potentials using the disclosed spatial-dependent (SP) as disclosed herein. FIG. 2 depicts a component configuration 400 of a computing device 402, which includes a database 410 along with other related computing components. In some aspects, the computing device 402 is similar to computing device 802 (shown in FIG. 1). A user 404 may access components of the computing device 402. In some aspects, the database 420 is similar to the database 808 (shown in FIG. 1).

In one aspect, the database 410 includes MRI data 418, optical scan data 412, and EMMI data 416. Non-limiting examples of MRI data 418 may include structural MRI data that is analyzed to determine the MRI-based uterine and body surface geometries used to implement EMMI mapping as described herein. Non-limiting examples of MRI data 418 may include structural MRI data that is analyzed to determine the MRI-based uterine and body surface geometries used to implement EMMI mapping as described herein. Non-limiting examples of suitable optical scan data 412 optical scan data that is analyzed to determine the optically-based body surface geometry used to implement EMMI mapping as described herein. Non-limiting examples of EMMI data 416 include any values of parameters defining the SP method of EMMI reconstruction, such as any of the parameters from the equations described herein. In one aspect, the body-uterus geometry data 412 may be combined with the disclosed methods of processing EMG signals and implementing EMMI mapping in accordance with the EKG measurements obtained by the EMMI system (see FIG. 1) to reconstruct the uterine surface potential map using the disclosed SP method, as described herein. Non-limiting examples of suitable optical scan data 412 optical scan data that is analyzed to determine the optically-based body surface geometry used to implement EMMI mapping as described herein. Non-limiting examples of EMMI data 416 include any values of parameters defining the methods of processing EMG signals and implementing EMMI mapping in accordance with the methods described herein.

The computing device 402 also includes a number of components that perform specific tasks. In the exemplary aspect, the computing device 402 includes a data storage device 430, an MRI component 440, a 3D optical scanning component 450, an EMMI component 470, an SP component 480, and a communication component 460. The data storage device 430 is configured to store data received or generated by the computing device 402, such as any of the data stored in database 410 or any outputs of processes implemented by any component of the computing device 402. The MRI component 440 is configured to operate an MRI system 810 to obtain structural MRI data from a patient. The 3D optical scanning component 450 is configured to operate a 3D optical scanning system to produce an optically-based body surface using the methods described herein. The EMMI component 470 is configured to obtain and analyze EMGs as well as to implement electromyometrial imaging as described herein. The SP component 480 is configured to transform the plurality of EMG signals into a map of uterine surface electrical potentials using the disclosed spatial-dependent (SP) method as described herein.

The communication component 460 is configured to enable communications between the computing device 402 and other devices (e.g. user computing device 830, MRI system 810, 3D optical scanning system 815, and/or EMMI system 820 shown in FIG. 1) over a network, such as network 850 (shown in FIG. 1), or a plurality of network connections using predefined network protocols such as TCP/IP (Transmission Control Protocol/Internet Protocol).

Figure 3:
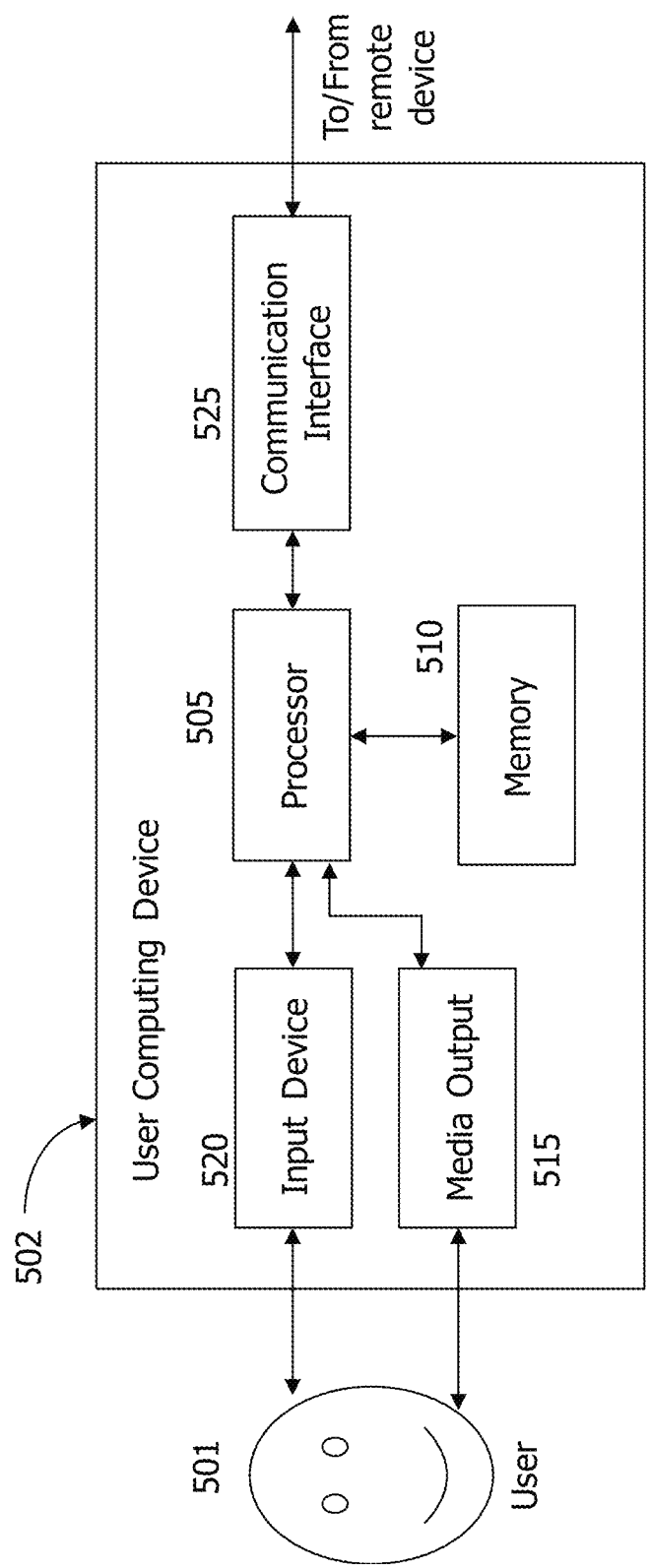
FIG. 3 is a block diagram schematically illustrating a remote or user computing device in accordance with one aspect of the disclosure.

FIG. 3 depicts a configuration of a remote or user computing device 502, such as the user computing device 830 (shown in FIG. 1). The computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
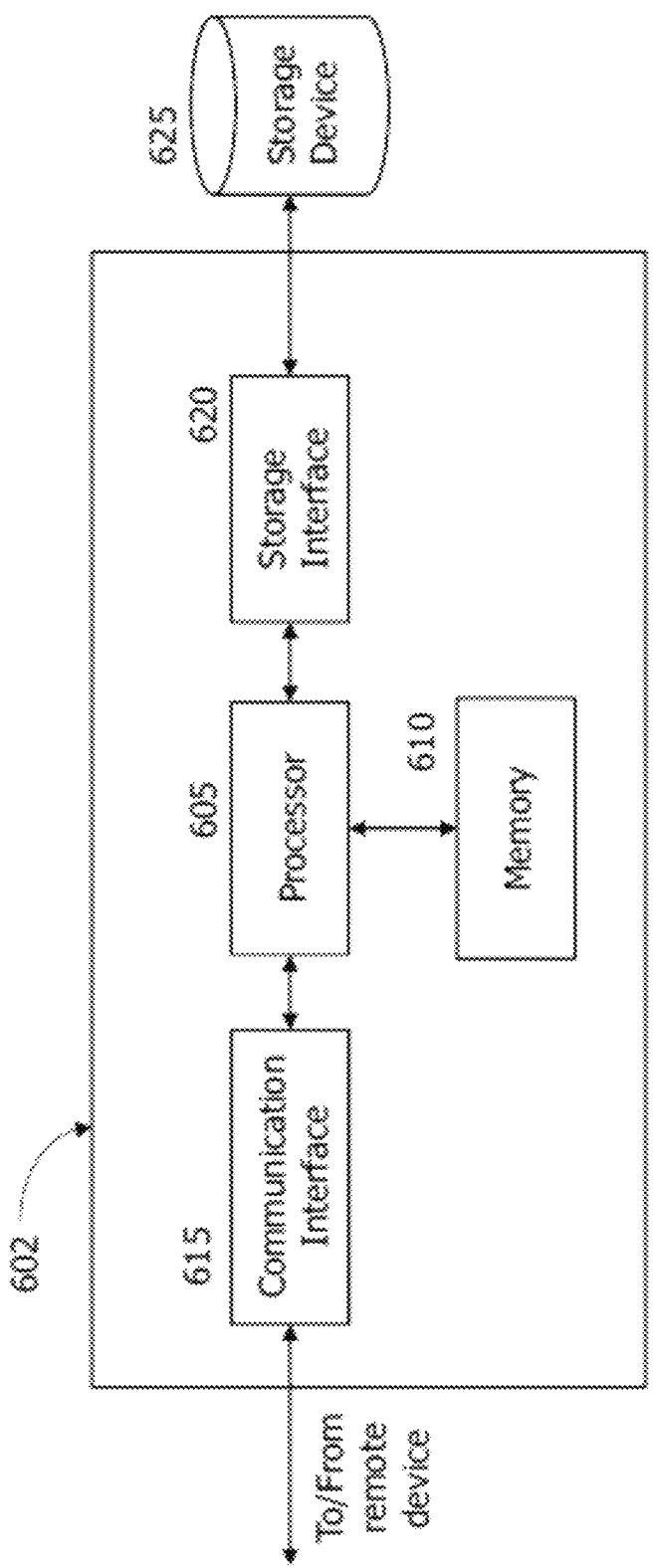
FIG. 4 is a block diagram schematically illustrating a server system in accordance with one aspect of the disclosure.

FIG. 4 illustrates an example configuration of a server system 602. Server system 602 may include, but is not limited to, database server 806 and computing device 802 (both shown in FIG. 1). In some aspects, server system 602 is similar to server system 804 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 830 (shown in FIG. 1) or another server system 602. For example, communication interface 615 may receive requests from user computing device 830 via a network 850 (shown in FIG. 1).

Processor 605 may also be operatively coupled to a storage device 625. Storage device 625 may be any computer-operated hardware suitable for storing and/or retrieving data. In some aspects, storage device 625 may be integrated in server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local, remote, o cloud-based processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, functional connectivity data, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function that maps outputs to inputs and utilize the predictive function to generate ML outputs based on data inputs. The example inputs and example outputs of the training data may include any of the data inputs or ML outputs described above.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate an ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, an ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program is provided, and the program is embodied on a computer readable medium. In one aspect, the system is executed on a single computer system, without requiring a connection to a sever computer. In a further aspect, the system is being run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

EXAMPLES

The following examples illustrate various aspects of the disclosure.

Example 1: EMMI Imaging of Labor Uterine Contractions

To demonstrate the feasibility of 3D noninvasive imaging of labor uterine contractions using EMMI, the following experiments were conducted.

A. Methods

The MRI scanner used for these experiments was a 3T Siemens Prisma/Vida with a radial volume interpolated breath-hold examination fast T1-weighted sequence. The resolution of the MRI image was 1.56 mm×1.56 mm, and the slice thickness was 4 mm. The MRI images were acquired with patient in a supine position. For patients unable to lie in a supine position, MRI images were acquired with the patients in a left lateral position instead.

The 3D optical scanner (Artec 3D, Luxembourg) used in these experiments used structured white light to capture the 3D surface information, which was safe for scanning pregnant women. The 3D accuracy of the scanner was 0.1 mm and the resolution was 0.5 mm. The 3D scanning of the back surface was taken with the patient sitting on the bed, and the 3D scanning of the abdominal surface was taken with the patient lying in supine position.

BioSemi pin-type electrodes were assembled into 2×4 patches with 3-cm inter-sensor distance for use in these experiments, shown illustrated in FIG. 5C. The assembled electrode patches allowed enhanced electrode contact with the skin on the pregnant women's abdominal surface with large curvatures. Up to 24 electrode patches (192 unipolar electrodes) were applied to each patient's body surface. The layout of the patches on the body surface was referred to the belly button on the anterior surface and to the spine on the posterior surface with a vertical-horizontal ruler coordinate (see FIG. 5B). This ruler coordinate was used to reproduce the layout between MRI scanning and bioelectricity mapping. The electrode patches were connected to an analog-to-digital converter (ADC) box (see FIG. 5D) and the bioelectricity signals from up to 192 unipolar electrodes were simultaneously recorded with a sampling rate of 2048 Hz.

The MRI images, optical 3D scanned surfaces, and measured electromyograms were processed using EMMI software provided in the form of a customized MATLAB software package installed on a laptop computer (see FIG. 5D). The EMMI software performed signal pre-processing to remove electrical noise and baseline drifts, to eliminate poor contact signals and to detect artifacts of movement. The EMMI software further performed body-uterus geometry construction to acquire the body-uterus geometry (coordinates of uterine and body surface sites and triangular meshes). The EMMI software additionally performed inverse computation employing a method of fundamental solutions to compute uterine surface potentials based on the reconstructed body-uterus geometry and the measured body surface potentials. The uterine surface potentials were further post-processed using the EMMI software for further data visualization and analysis. A detailed description of the components of the EMMI software is described below.

B. EMG Signal Pre-Processing

Raw data (see FIG. 7A) were filtered by a fourth-order butter-worth high-pass with a cutoff frequency of 0.34 Hz and a low-pass of 40 Hz, followed by down-sampling by 20 using a mean filter. An eighth order butter-worth low-pass with a cutoff frequency of 1 Hz was the applied, followed by multi-step artifacts detection applied to the band-passed signal to automatically detect the bad EMGs and bad body surface potential maps (BSPMs). FIG. 7B is a graph showing the resulting filtered EMG data. EMGs with mean absolute magnitudes larger than 100 times of the first quartile of the mean absolute magnitudes of all EMGs were defined as bad EMGs due to poor contact. BSPMs with mean absolute magnitudes larger than 10 times the median values of the mean absolute magnitude of all BSPMs were defined as bad BSPMs due to maternal/fetal movements.

C. Body-Uterus Geometry Construction

The sagittal slices of the MRI images were segmented slice by slice in Amira software to generate the uterine and body surface geometries separately. The 3D optical scanned body surfaces defining the layouts of the electrode patches were post-processed using Artec studio to achieve accurate and high-quality surfaces with electrode sensor locations. The surfaces from MRI images and 3D optical scans were represented by XYZ coordinates as well as triangular meshes.

The 3D optical surfaces were registered to the MRI body surface using a two-step alignment method, as illustrated in FIG. 14. As illustrated in step B, a least-square rigid alignment was conducted with an Amira function by defining 6-8 corresponding location pairs (see yellow points in step B) on the MRI-derived body surface (top) and the optically-scanned body surface (bottom). A non-rigid alignment (Normal projection or Equal length projection) was implemented using a customized MATLAB algorithm, as shown in step D of FIG. 14.

A normal projection, illustrated in the upper image of step E in FIG. 14, was used for the non-rigid alignment at the patient's right anterior surface of left lateral position, the center anterior surface of supine position, and the back surface of both positions. Referring to the upper illustration of step E, the green circle represents the optical surface, the blue circle represents the MRI surface from the top view, the arrow represents the normal direction of the point on the optical surface (A), and a red dot (A') represents the normal projected electrode location on the MRI surface.

An equal length projection, illustrated in the lower image of step E in FIG. 14, was used for the non-rigid alignment at the patient's left anterior surface of left lateral position and outer anterior surface of supine position. Referring to the lower illustration of step E projection, blue dots (B) represent electrode locations on the optical surface, red dots (B') represent projected electrode locations on the MRI surface, the yellow curve represents the length from location B to the vertical ruler, and the red curve represents the length from location B' to the vertical ruler; the lengths of the two curves were kept equal.

Once the registration was completed, the locations of the electrodes were marked and represented by XYZ coordinates. The resulting body surface electrode locations and the uterine surface derived from MRI images were constructed as the body-uterus geometry.

D. Inverse Computation

An inverse computation as described below was used to reconstruct uterine potentials based on the measured body surface potentials and patient-specific body-uterus geometry. The volume between the uterine surface and body surface $\Omega$ was assumed to be homogeneous and to contain no primary electrical sources and eligible inductive effects. The inverse problem was mathematically formulated as a Cauchy problem for the Laplace's equation (see Eqn. (1)) with two boundary conditions (Dirichlet condition, Eqn. (2) and Neumann condition, Eqn. (3)) on the body surface $F_B$:

$$\nabla^2 \phi(x) = 0, x \in \Omega \qquad \text{Eqn. (1)}$$

$$\phi(x) = \phi_{B(x)}, x \in \Gamma_B \qquad \text{Eqn. (2)}$$

$$\sigma \frac{\partial \phi(x)}{\partial n} = 0, x \in \Gamma_B \qquad \text{Eqn. (3)}$$

where $\Gamma_B$ represents the body surface, $\phi_{B(x)}$ is the measured body surface potentials at location x, $\sigma$ is the conductivity of the volume conductor $\Omega$ (assumed to be homogeneous), and n is the normal direction at x on body surface. Since the conductivity of the air was assumed to be essentially zero, the right side of Eqn. (3) was simplified to zero.

The method of fundamental solutions, a mesh-free method robust to noise, was employed to discretize Eqns. 1, 2, and 3 and to construct the relationship between the measured body surface potentials ($\phi_B$) and uterine surface potentials ($\phi_U$), as expressed in Eqn. (4). Tikhonov regularization was employed to stabilize the ill-posed inverse computation. A fix regularization value of 0.01 was used in the Tikhonov-based inverse computation.

$$\Phi_B = A\Phi_U \qquad \text{Eqn. (4)}$$

where $\Phi_B$ is a matrix of M×T, $\Phi_U$ is a matrix of N×T, A is a matrix of M×N, M represents the number of electrodes on the body surface, N represents the number of discrete points on the uterine surface. and T represents the number of potentials maps.

E. Data Visualization and Analysis

Three types of uterine signals were generated using the inverse computations described above: a uterine surface potential map, uterine electrograms, and an isochrone map. The uterine surface potential map was a spatial distribution of uterine potentials at an instant time on the 3D uterine surface. Each uterine electrogram characterized the potentials with respect to time at a specific uterine site. Typically, electrograms at around 320 uterine sites were calculated. The isochrone map characterized the sequence of uterine activation derived from the local activation times during an observation window. The observation window of an EMG burst was defined starting from a time point when the uterus was generally quiet to a time point when the uterus was activated and returned to quiescence. The activation time for an EMG burst at each uterine site was defined separately based on the magnitudes of the EMG burst in an electrogram.

Based on the isochrone maps, activation ratio was defined as the ratio between the area of the active uterine region and the area of the entire uterine surface. The activation duration was defined as the time difference between the activation time of the first active uterine site and the activation time of the last active uterine site. The activation time difference between each active neighbor uterine site pair was calculated. The active pair was defined as two adjacent uterine sites activated during an observation window. An active pair with an activation time difference less than 0.2 s (temporal resolution of down sampled signal) was defined as a synchronized pair, and the total number of the synchronized pairs over the total number of active pairs was defined as the synchronized ratio. Propagation length was calculated as the Euclidian distance of two uterine sites in a non-synchronized pair. The propagation speed of non-synchronized pairs was defined as the propagation length divided by the activation time difference. The slow conduction ratio represented the percentage of active pairs with a propagation speed smaller than 1 cm/s. The median speed was the median propagation speed of the non-synchronized pairs during an EMG burst.

F. Study Procedure 27 nulliparous patients were recruited for these experiments, but 16 patients were excluded for various technical reasons. 11 nulliparous patients with gestational ages ranging from 36 to 40 weeks completed both MRI scan and bioelectricity mapping; 2 patients were excluded from the analysis due to insufficient bioelectrical data. The clinical information, including cervical exams, TOCO strip measurements and delivery outcomes were recorded. The nine remaining patients were categorized into three groups based on their mean cervix dilation during the bioelectricity mapping: 4~6 cm, 6~8 cm and 8~10 cm. Representative cases of each category were analyzed in these experiments.

G. Detection of EMG Burst

Figure 15A:
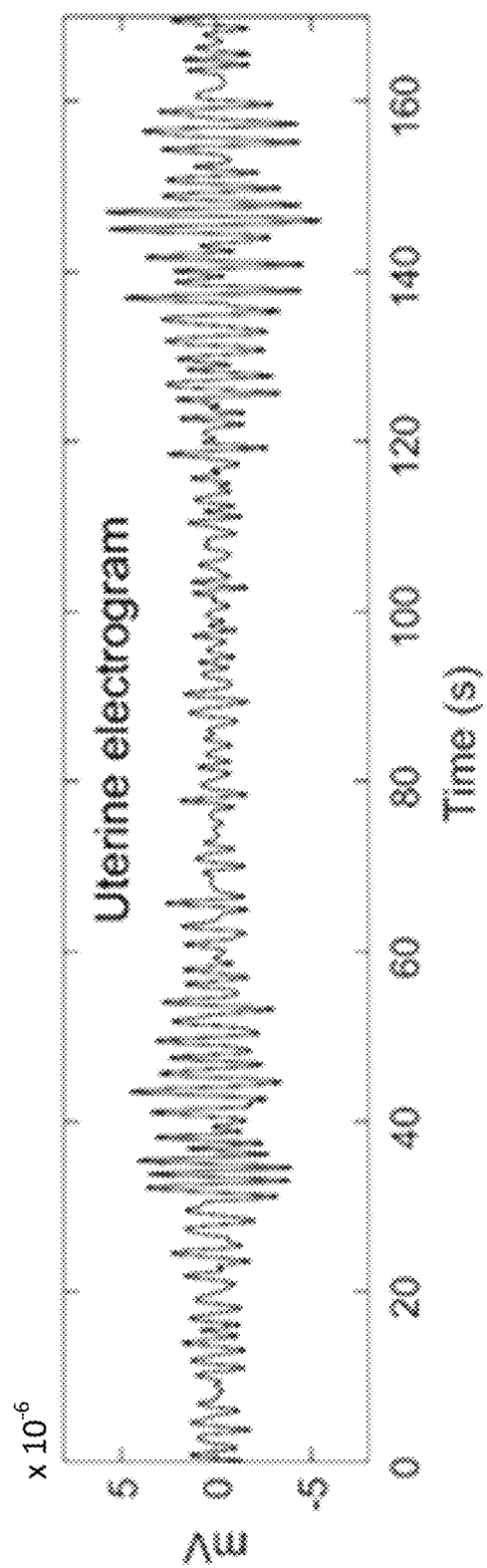
FIG. 15A is a graph of a representative uterine electrogram.
Figure 15B:
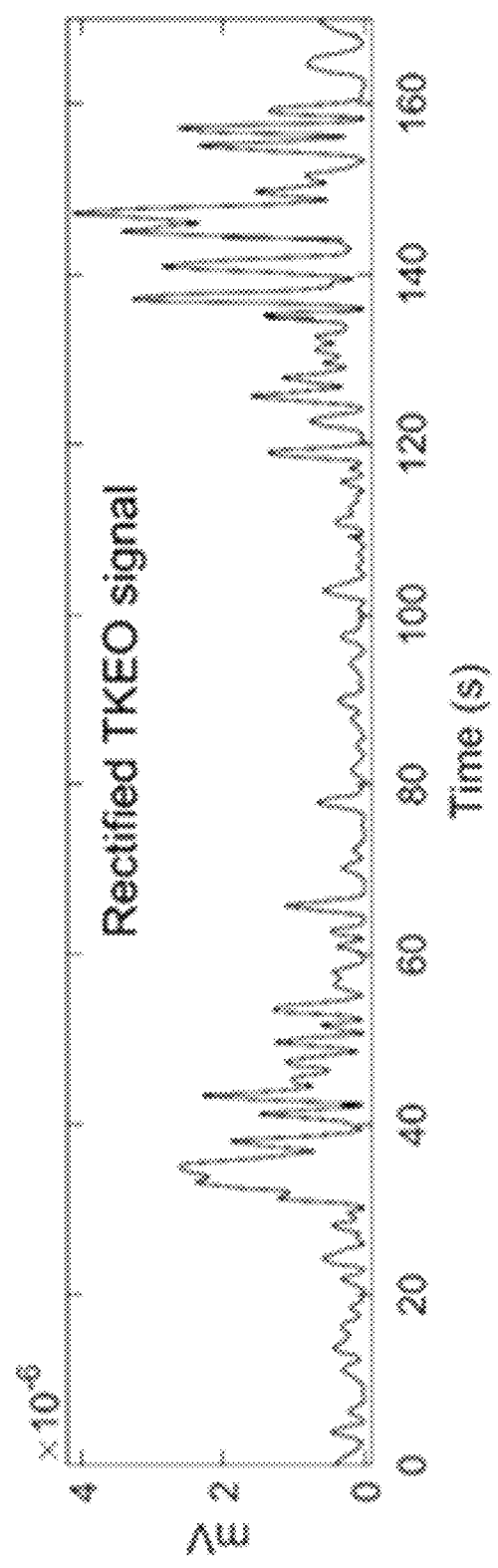
FIG. 15B is a graph of a rectified signal after applying the Teager-kaiser energy operator (TKEO) to the uterine electrogram of FIG. 15A.
Figure 15C:
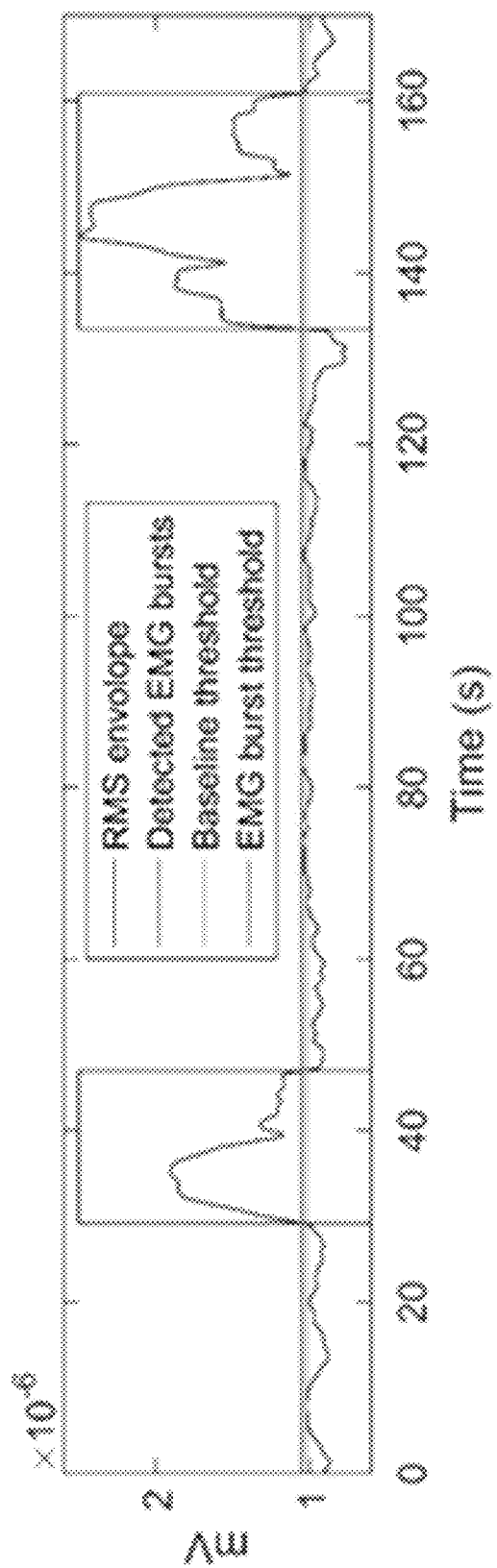
FIG. 15C is a graph showing an RMS (root mean square) envelope of the rectified TKEO signal of FIG. 15B (black line) and detected EMG bursts (blue line); the green line defines a baseline threshold and the red line defines the EMG burst threshold.

The uterine electrograms (FIG. 15A) were pre-conditioned using the Teager-Kaiser Energy Operator (TKEO) to improve the signal condition at the onset and offset of the EMG bursts (FIG. 15B). A root-mean-square (rms) envelope with a window length of 7 second was derived from the rectified TKEO signal (Black line in FIG. 15C). The threshold of the baseline (Green line in FIG. 15C) was defined as 1.01 times the median values of the RMS envelope. The baseline was defined as the RMS envelope that was lower than the baseline threshold. The threshold for defining the EMG burst was defined as the mean of the baseline plus twice the standard deviation of the baseline. The EMG burst was defined as the RMS envelope that was over the EMG burst threshold.

H. EMMI Procedure

Figure 6:
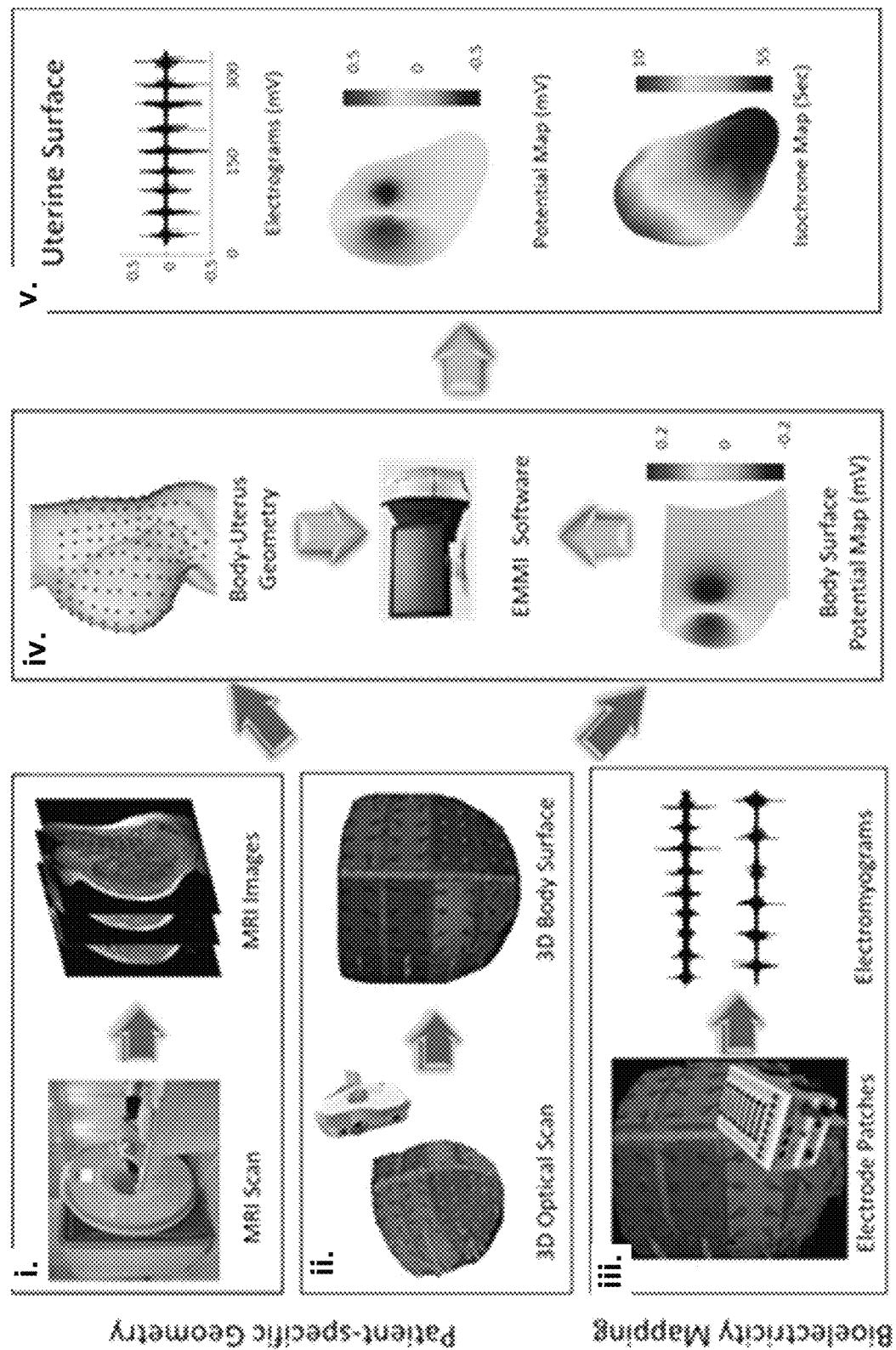
FIG. 6 is a flowchart of the elements of a process of EMMI using the EMMI system in accordance with one aspect of the disclosure.

EMMI was conducted in three phases, shown summarized in FIG. 6. MRI scans was conducted on patients at a gestation age of around 37 weeks. Each patient wore up to twenty-four MRI patches (up to 192 single markers) around the abdomen and lower back surface; the configuration of each MRI patch was matched to the corresponding configuration of the electrode patches worn during subsequent bioelectrical measurements as described below.

A portable electrical mapping device was used to perform multi-channel bioelectricity mapping on patients nearing active labor with cervix dilations of around 4 cm. Customized pin-type electrode patches were applied to each patient at locations on the body surface matched to the corresponding locations of the MRI patches used for the previous MRI scan. The duration of each body surface bioelectricity recording was around 15 minutes, and typically four recordings were conducted for each patient. To monitor any changes in the electrode patch positions due to the usage of clinical devices such as TOCO monitor, an optical 3D scanner was employed to record the electrode positions during the bioelectricity mapping. EMMI inverse imaging based on the MRI images, 3D body surface contours, and measured EMGs was performed using EMMI software to generate body-uterus geometry and body surface potential maps. The electrical information on the uterine surface, including electrograms (electrical activities over time at each uterine site), potential map (electrical activity distribution on the uterine surface at an instant time) and isochrone map (electrical activation sequence during a specific observation window) were reconstructed by solving the three-dimensional Cauchy problem using the method of fundamental solutions described above. The details of EMMI hardware and software were described above.

I. EMMI-Imaged EMGs, Potential Maps and Isochrone Map

Figure 10A:
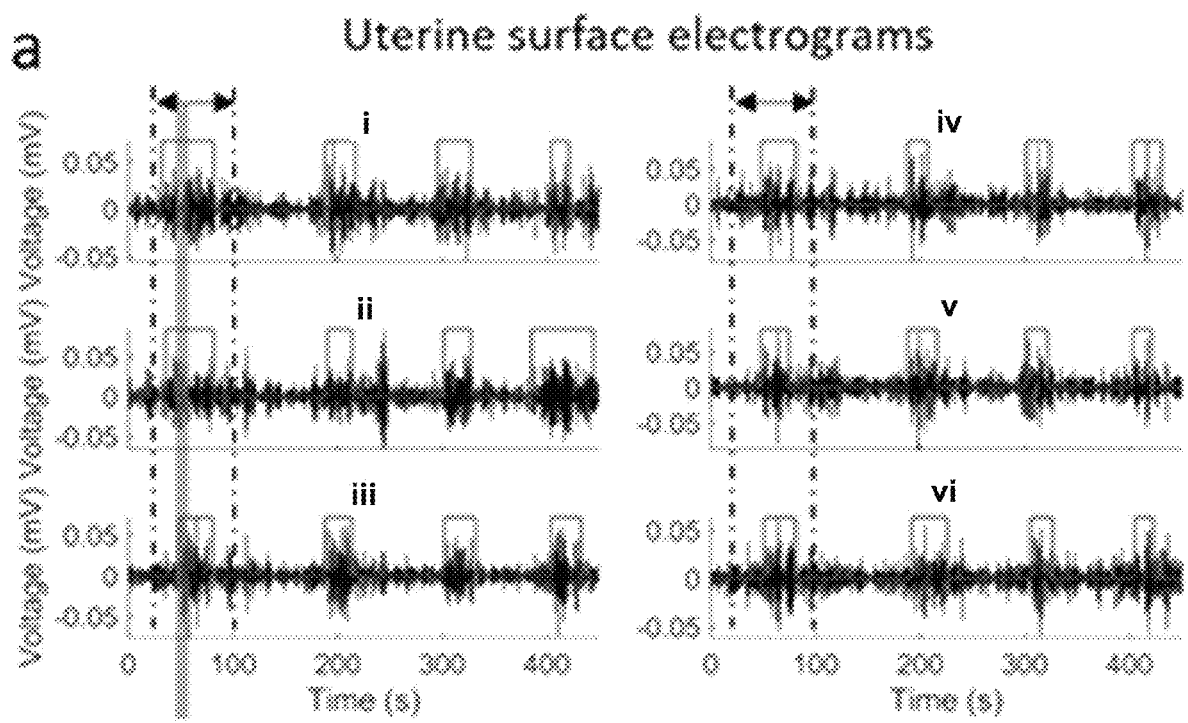
FIG. 10A contains a series of EMMI-imaged uterine electrograms corresponding to indicated sites marked in the anterior isochrones map of FIG. 10B.
Figure 10B:
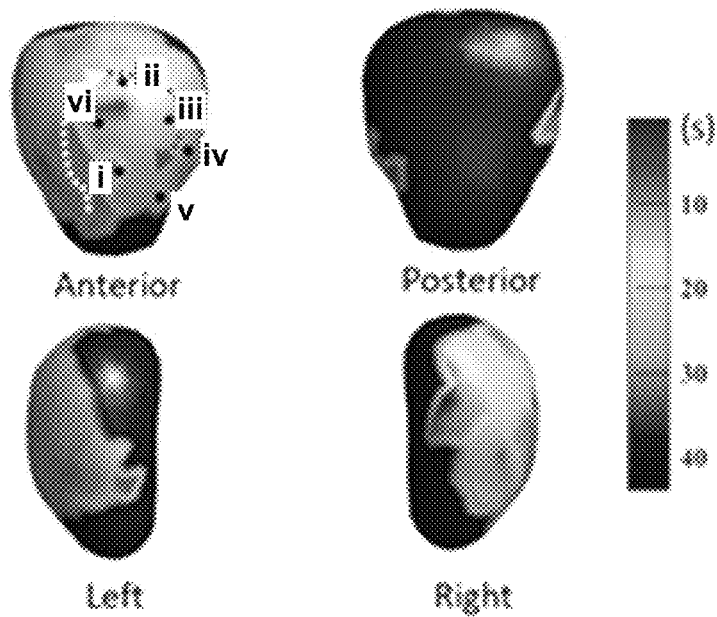
FIG. 10B contains four views of an isochrone map of the first EMG burst with an observation window marked by double arrows in FIG. 10A, with warm (red) color representing early activation, cool (blue) color representing late activation, and dark blue representing non-activation.

The measurements of one nulliparous patient were analyzed at a cervix dilation of about 4 cm. Six representative EMGs are displayed at locations i, ii, iii, iv, and v shown labeled in FIG. 10B. Referring to FIG. 10A, red rectangle demarcate activation times (onsets of the rectangles) as well as durations (widths of the rectangles) of EMG bursts at each uterine site. For each uterine contraction, the activation times and durations of the EMG bursts temporally varied for different contractions and spatially varied at the different uterine regions. As shown in FIG. 10A, the duration of the first EMG burst was the longest and the fourth EMG burst was the shortest at uterine site i within the demonstrated recording period, while at uterine site ii the fourth EMG burst was the longest and the second EMG burst was the shortest. Comparing the EMG bursts at different sites, EMG bursts activated earlier and lasted longer at uterine sites i and ii than the other four uterine sites, especially the first EMG burst.

Activation times at each uterine site were calculated within the observation window marked by double arrows in FIG. 10A for each uterine site. The activation times and position of each uterine site were used to construct the isochrone map shown in FIG. 10B. Within the isochrone map, early activation regions are represented as warm colors (red) represents, late activation regions are represented as cool colors, and dark blue represents no activation within the observation window. The isochrone map described a local activation sequence starting from lower anterior left (near uterine site i) to the middle anterior (near uterine site vi) along the pathway shown by overlaid arrows in FIG. 10B.

Figure 10C:
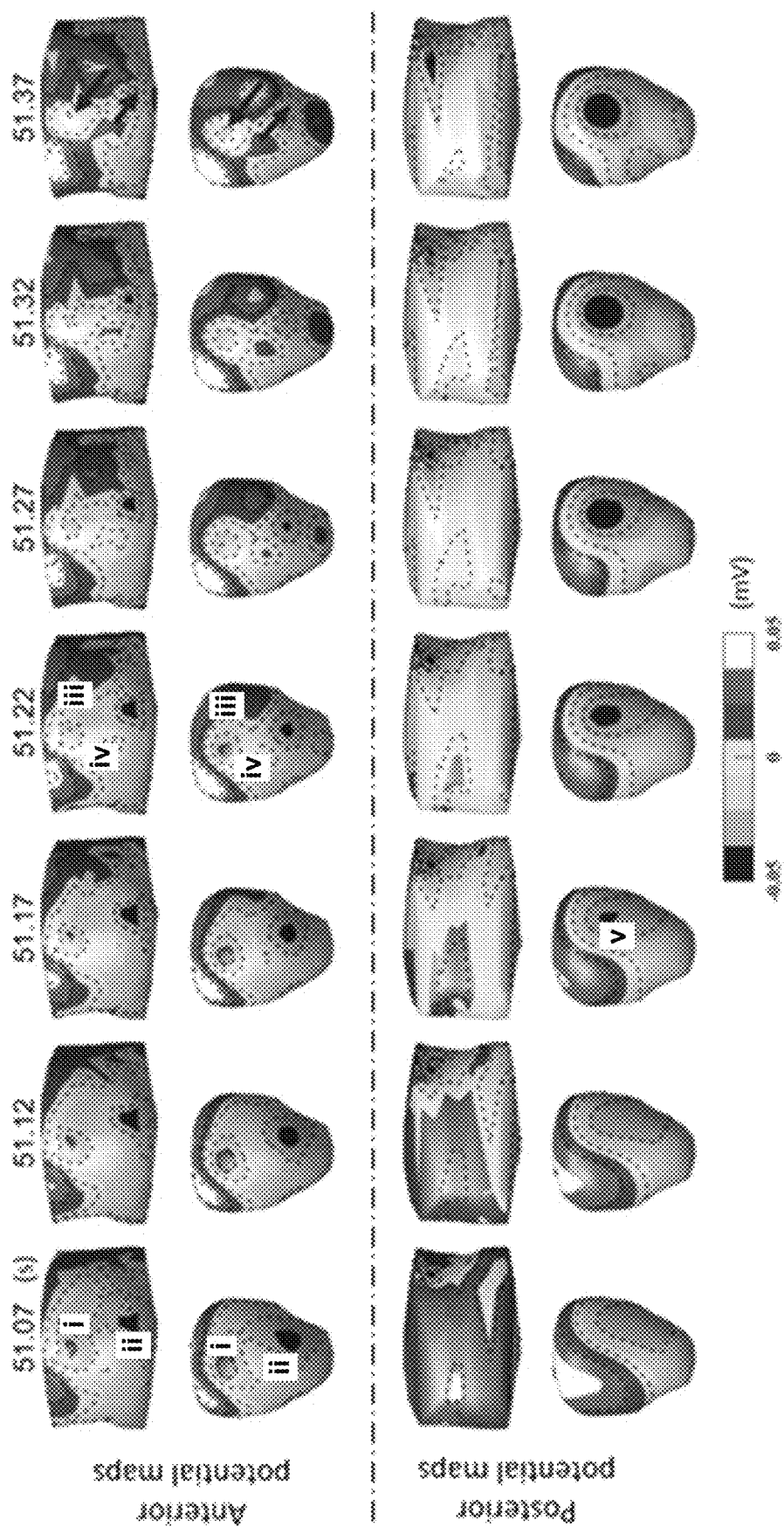
FIG. 10C contains successive anterior and posterior body surface potential maps (tops) and uterine surface potential maps (bottoms) within a 300-millisecond period (denoted as a blue slice in the electrograms of FIG. 10A) at instantaneous times denoted above the anterior body surface potential maps, with white color representing positive potentials and blue color representing negative potentials; dashed lines denote contours with the same potential values.

FIG. 10C shows anterior views (upper two rows) and posterior views (lower two rows) of seven representative body surface potential maps and EMMI-imaged uterine surface potential maps at a series of times during the 300-millisecond period marked by an overlaid blue rectangle in FIG. 10A. The 320 uterine sites were uniformly distributed on the uterine surface, while the 160 body surface electrodes were not uniformly distributed due to the large abdomen surface curvature, the simultaneous placement of clinical monitors such as TOCO, and the tape covering the epidural anesthesia tube on the back surface. The inter-site separation distance on the uterine surface was 25±2.2 mm, and the inter-electrode separation distance on the body surface was 46±33.5 mm.

Two negative potential regions (marked as regions i and ii) were detected at the first anterior uterine and body surface maps that diminished over time. Two maximal potential regions (marked as regions iii and iv) were detected starting at the fourth anterior potential maps that enlarged over time. Starting at the eighth potential map, two pairs of maxima-minima region with opposite directions co-existed. Comparing the anterior body surface maps with the uterine surface maps, the boundaries of maxima or minima regions in uterine maps were more explicit and sharper than their counterparts in the body surface maps. In the posterior potential maps, a minima region appeared on the third uterine surface (marked as v) that enlarged and moved upwards over time. However, the corresponding body surface potential maps barely showed any visible propagation patterns. Interpolation effects on the body surface maps were observed, especially on the posterior side due to the large inter-electrodes distance and non-uniform layout of the electrodes. In comparison, EMMI-imaged uterine surface potential maps had much higher spatial resolution, allowing faithful imaging of the electrical activities during uterine contractions.

To study activation sequences at different labor stages, the measurements of three nulliparous cases at cervix dilation around 4-9 cm were analyzed and isochrone maps of two representative uterine contractions were generated for each case. Characterization of each of the three nulliparous cases are summarized in Table 1 below:

TABLE 1

Selected Nulliparous Patient Cases

| Case Number | Labor Type | Gestation Age | Cervix Dilation | Time to Delivery |
| --- | --- | --- | --- | --- |
| 1 | Induction | 40 w 1 d | 4 cm | 4.5-5 hr |
| 2 | Induction | 37 w 1 d | 6-8 cm | 2-3 h |
| 3 | Spontaneous | 39 w 0 d | 7-9 cm | 1-2 hr |

Figure 11A:
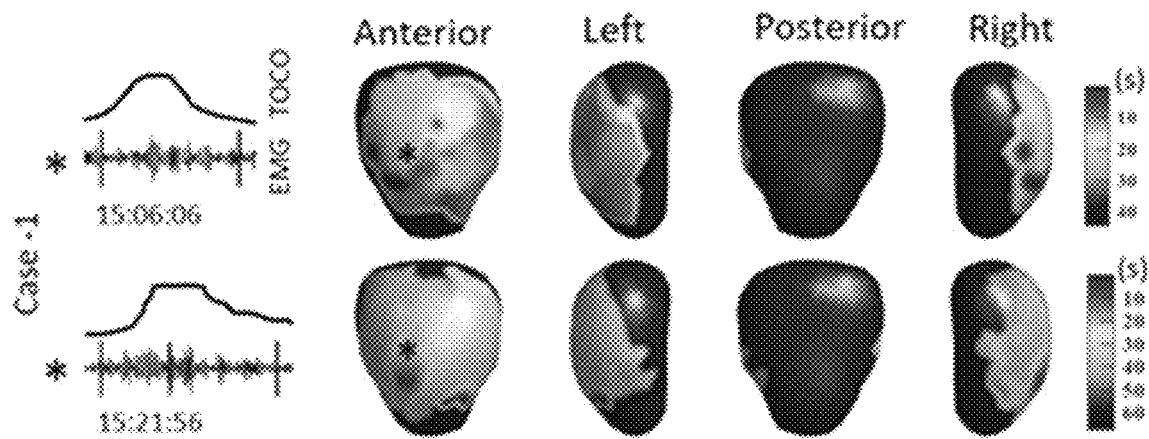
FIG. 11A contains representative EMG bursts and corresponding tocodynamometer (TOCO) signals simultaneously recorded at the star-denoted sites of the associated isochrone maps for a first case. Red and blue lines mark the time interval of the observation window, with the start time labeled below. Anterior, left, posterior, and right views are presented for each isochrone map; warm (red) color represents early activation, cool (blue) color represents late activation, and dark blue represents no activation during each respective observation window.

FIG. 11A shows the isochrones of two uterine contractions separated by about 15 minutes interval for the patient of case #1 under induced labor at a cervix dilation of about 4 cm. The two EMG bursts measured during contractions matched well with the TOCO detected uterine contractions (see left graphs of FIG. 11A). The early activation region (warm color) was positioned at the lower left anterior region of the first isochrone, and at the lower right anterior region of the second isochrone. However, the total active uterine areas (non-dark blue area) were similar between the two contractions. The activation ratio was defined as the percentage of the uterine surface that contributed to the measured electrical signals during uterine contraction. The mean activation ratio of the two representative contractions for case #1 was around 35%.

Figure 11B:
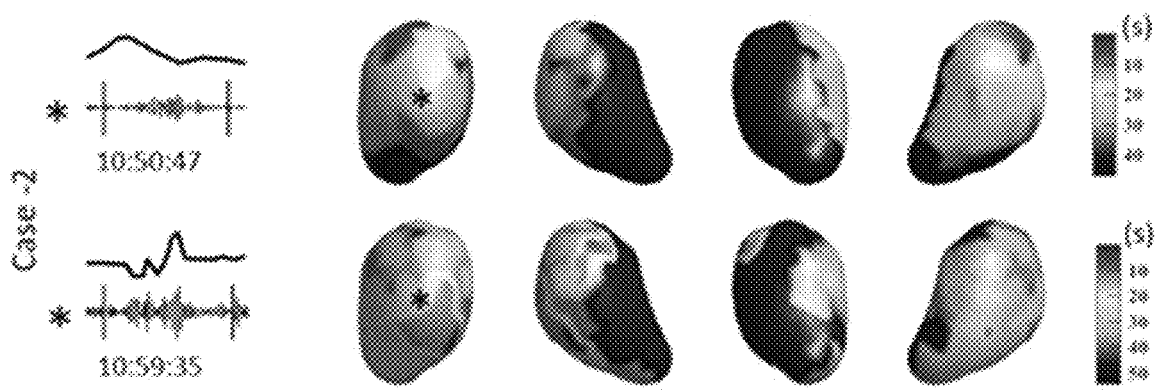
FIG. 11B contains representative EMG bursts, corresponding tocodynamometer (TOCO) signals, and isochrone maps for a second case, annotated as described in FIG. 11A.

FIG. 11B shows the isochrones of two uterine contractions separated by about 9 minutes interval for the patient of case #2 under induced labor at a cervix dilation of about 7 cm. The early activation regions were positioned at the right fundus region of the first isochrone and at the middle anterior region of the second isochrone. The activation ratio was around 55% of the uterine surface, similar to the activation ratio in the patient of Case #1 described above.

Figure 11C:
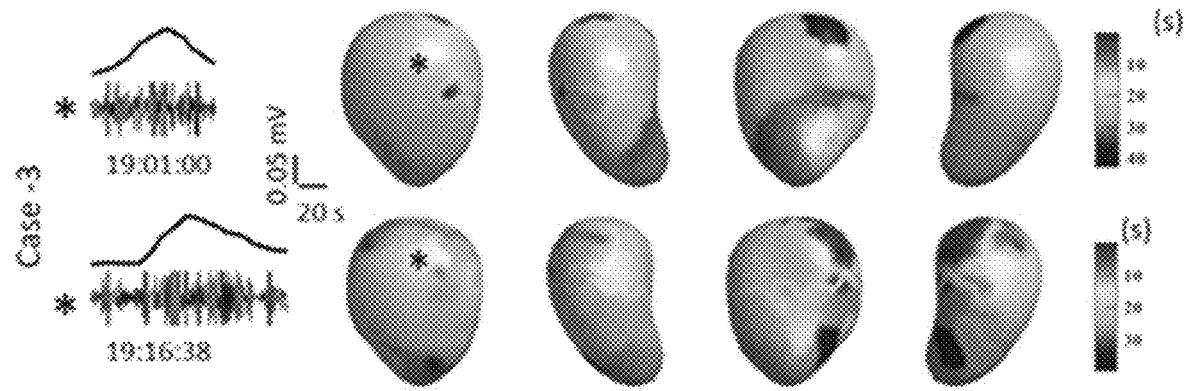
FIG. 11C contains representative EMG bursts, corresponding tocodynamometer (TOCO) signals, and isochrone maps for a third case, annotated as described in FIG. 11A.

FIG. 11C shows the isochrones of two spontaneous uterine contractions separated by about 15 minutes interval for the patient of case #3 at a cervix dilation of about 8 cm. The early activation regions were mainly located at the left anterior and fundus regions of the uterus of the first isocrone and at the posterior uterus region in the second isochrone. Although the non-active regions were at different locations between the two contractions, an activation ratio of about 87% of the uterine surface was detected for both contractions. Comparing FIGS. 10A, 10B, and 10C, the activation patterns changed across different EMG bursts and different patients, but the active ratio was consistent between patients.

The activation times of all EMG bursts measured for all cases were computed, and the activation and propagation features of the EMG bursts were analyzed based on these activation times. Nine EMG bursts were analyzed for each of cases #1 and #2, and 7 EMG bursts were analyzed in case #3. For each EGM burst, the activation ratios (FIG. 12A), activation durations (FIG. 12B), synchronized ratios (FIG. 12C), slow conduction ratios (FIG. 12D), and median speeds (FIG. 12E) were analyzed and summarized.

Figure 12B:
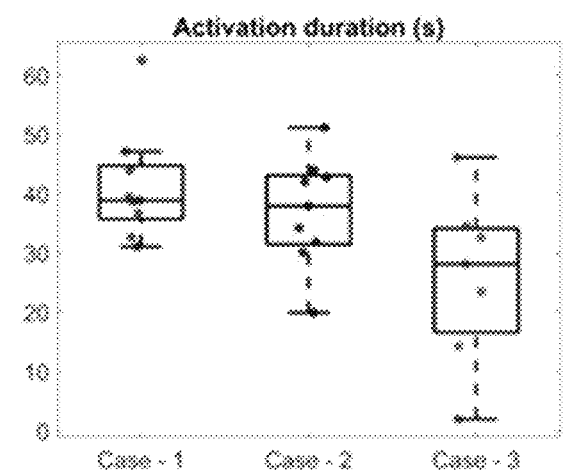
FIG. 12B is a graph summarizing activation durations of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.
Figure 12C:
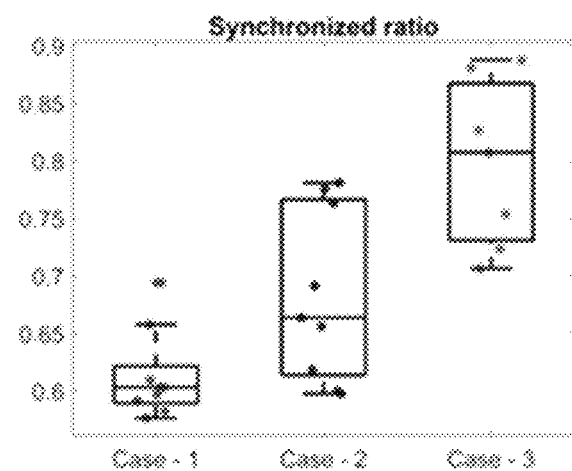
FIG. 12C is a graph summarizing synchronized ratios of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.
Figure 12D:
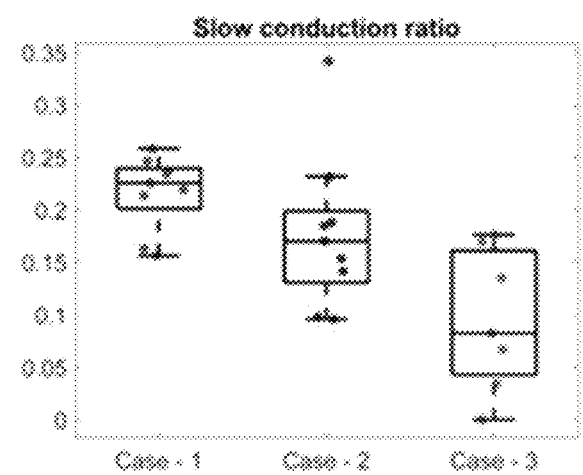
FIG. 12D is a graph summarizing slow conduction ratios of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.
Figure 12E:
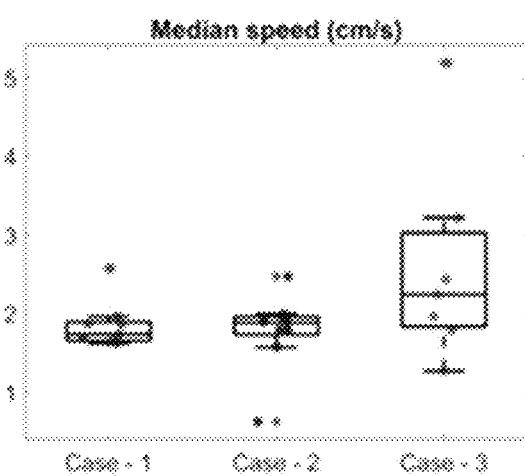
FIG. 12E is a graph summarizing median speeds of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.

The activation ratio (FIG. 12A) and synchronized ratio (12C) were significantly higher for case #3 relative to case #1, demonstrating that more and more uterine muscle was recruited into uterine contraction and synchronously active as the cervix dilation increases and labor is closer to the delivery. The activation duration (FIG. 12B) and the slow conduction ratio (12D) were lower in case #3 relative to case #3, suggesting that it took less time for the uterine muscle to complete a contraction, and there was lower areas of conduction blocked regions in the activated uterine muscle as the cervix dilation increased and labor was closer to the delivery. The median speed (FIG. 12E) was higher in case #3 relative to case #1, suggesting that the propagation speed increased as the labor status was nearer to the delivery. The increase of the propagation speed was consistent with the decrease of activation duration (FIG. 12B).

Figure 12F:
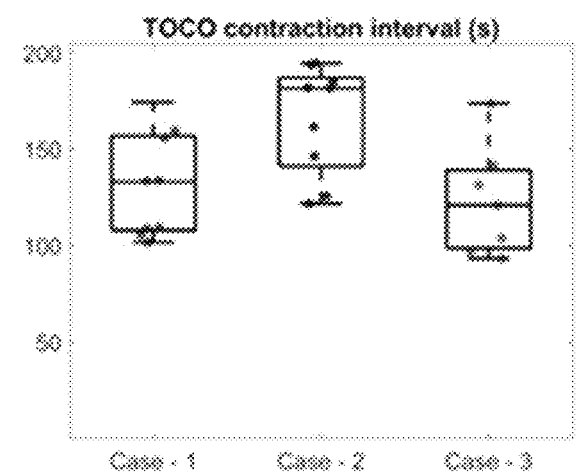
FIG. 12F is a graph summarizing TOCO contraction intervals of 9 EMG bursts from case #1 (FIG. 11A), 9 EMG bursts of case #2 (FIG. 11B), and 7 EMG bursts of case #3 (FIG. 11C); standard boxplots are shown with red, blue and magenta dots representing data from case #1, 2, and 3, respectively.

Contraction intervals were also measured for each uterine contraction using TOCO strips (FIG. 12F), which are typically used in clinical estimation of labor status. The contraction interval was defined as the duration between the peak of one uterine contraction to the peak of its previous uterine contraction. The TOCO measured uterine contractions were matched with EMG bursts. The contraction interval for the patient of case #2 was longer than the patients of the other two cases, and the contraction interval of the patient of case #3 was slightly shorter than that of the patient of case #1, demonstrating that TOCO measurements failed to reflect the labor status of the patients.

J. Early Active Regions

Figure 13A:
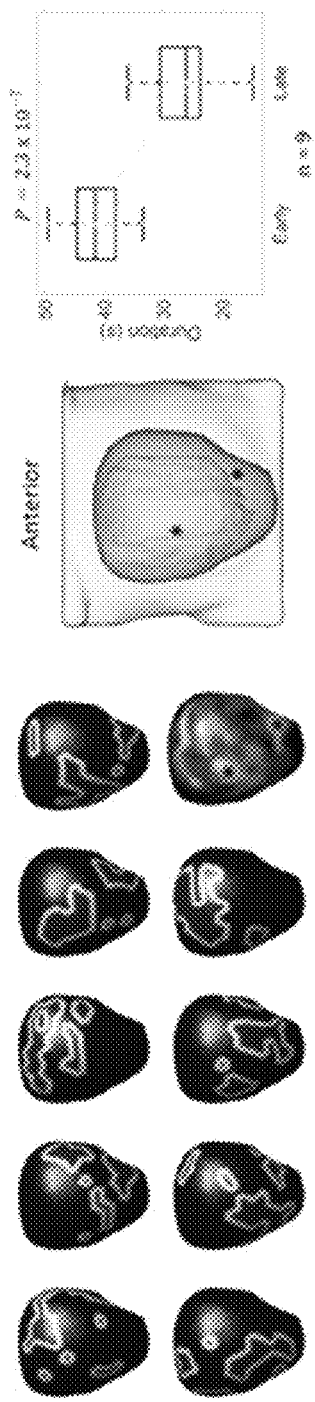
FIG. 13A contains a series of heatmaps of early regions of EMG bursts and probabilities of early activations happening at each uterine site among 9 successive EMG bursts from case #1 (FIG. 11A); red color in the red-blue heatmaps represents the early regions. Bright colors in the heatmaps represent high probabilities of early activations and dark colors represent low probabilities of early activations. Representative body-uterus geometry, including placenta geometry, is shown on the left, where green, red and yellow colors represent the body, uterus, and placenta surfaces, respectively. Boxplots summarizing the median duration of EMG bursts at early and late uterine sites are shown on the right, along with the sample size and p-value of a one-tailed paired t-test.
Figure 13B:
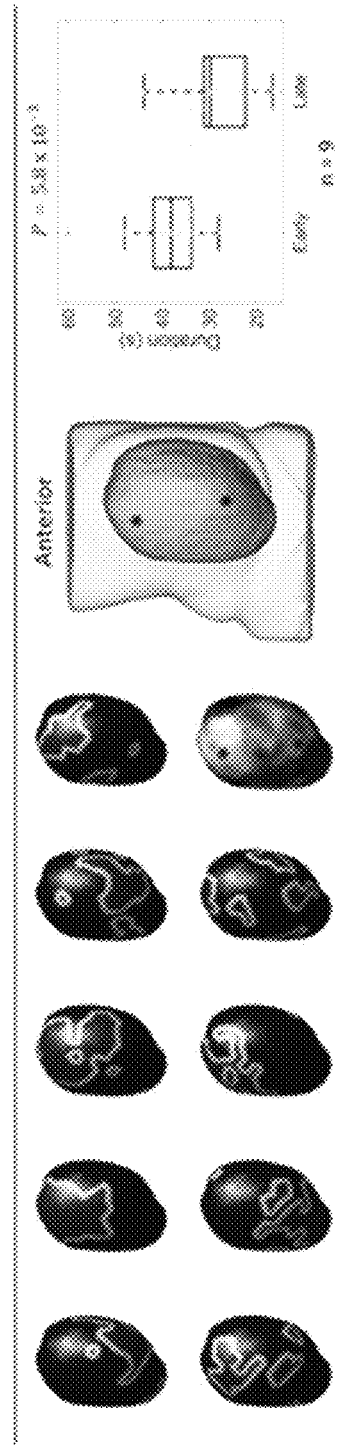
FIG. 13B contains a series of heatmaps of early regions of EMG bursts and probabilities of early activations happening at each uterine site among 9 successive EMG bursts from case #2 (FIG. 11B) and corresponding boxplots summarizing the median duration of EMG bursts at early and late uterine sites; features of the heatmaps and boxplots are labeled in a manner similar to FIG. 13A.
Figure 13C:
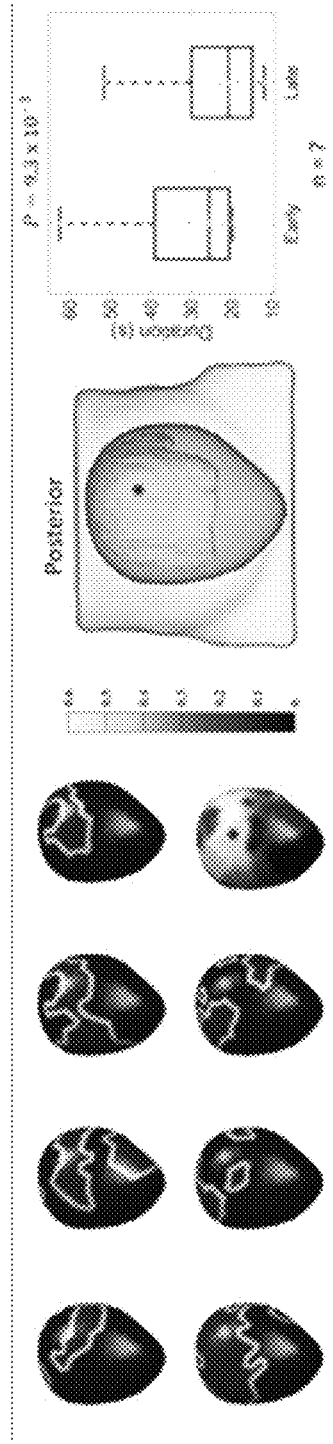
FIG. 13C contains a series of heatmaps of early regions of EMG bursts and probabilities of early activations happening at each uterine site among 7 successive EMG bursts from case #3 (FIG. 11C) and corresponding boxplots summarizing the median duration of EMG bursts at early and late uterine sites; features of the heatmaps and boxplots are labeled in a manner similar to FIG. 13A.

Based on the isochrones shown in FIGS. 11A, 11B, and 11C, the early active regions were dramatically different among EMG bursts. Early activation sites were defined as those uterine sites with activation times earlier than the first quartile of the activation times at all active uterine sites during an EMG burst, and the late activation sites were defined as uterine sites with activation times later than the third quartile of the activation times at all active uterine sites during an EMG burst. Early and late regions of EMG bursts for the patients of cases #1, #2, and #3 were identified based on analysis of isochrones similar to those shown in FIGS. 11A, 11B, and 11C. Spatial heatmaps of early and late regions of EMG bursts are illustrated in FIG. 13A (case #1, 9 successive EMG bursts), FIG. 13B (case #2, 9 successive EMG bursts), and FIG. 13C (case #3, 7 successive EMG bursts). In each of the maps of FIGS. 13A, 13B, and 13C, early regions are labeled red and late regions are labeled blue. The heatmaps for each case were further analyzed to produce probability distribution maps, in which a bright (yellow) color represents a high probability of early EMG bursts and a dark color (red/black) represents a low probability of early EMG bursts, as summarized in the color bar provided in FIG. 13C. The geometry of each patient's body (green), uterus (red), and placenta (yellow) are also shown illustrated next to each respective probability map in FIGS. 13A, 13B, and 13C. The regions with highest probability of early EMG burst are marked by black stars in the probability map and the geometry map. Early active regions tended to lie within an area where the placenta attached to the uterus.

The durations for each EMG burst were calculated at all uterine sites classified as early active sites and late activation sites as defined above for each of cases #1, #2, and #3. The median duration of EMG bursts at the early sites and late sites are summarized in the boxplots of FIGS. 13A, 13B, and 13C for cases #1, #2, and #3, respectively. A one-tail paired-t test was conducted with the null hypothesis that there is no difference in the EMG duration between the early sites and late sites. The null hypothesis was rejected for all three cases, demonstrating that the EMG bursts at early sites lasted significantly longer than those at the late sites (P-value<0.01).

The results of these experiments demonstrated that 3D noninvasive imaging of labor uterine contractions using EMMI was capable of imaging activation patterns, identifying early activation regions, and characterizing the propagation speeds of uterine contractions. EMMI demonstrated great potential for characterizing mechanisms of labor maturation, abnormal uterine contractions, and preterm births. Electrical activation patterns dynamically changed from contraction to contraction, suggesting the absence of a consistent "pacemaker"-initiated stable activation pattern. Although the early activation regions may change dramatically from one contraction to the next, the mean early activation maps (FIGS. 11A, 11B, and 11C) indicated that the same uterine regions consistently demonstrated early activation within successive observation windows for each patient. EMMI identified the most promising early activation regions collocated with placenta locations, which was consistent with previously published findings that electrical early activation sites may originate from placenta implantation sites. EMMI further identified late activation regions and found that uterine surface EMG burst durations were significantly longer in early activation regions than corresponding burst durations in the late activation regions (see FIG. 12B); those uterine regions that activate early and for long activation duration may drive contraction of the uterus.

Example 2: Clinical EMMI Imaging Procedures

To demonstrate the feasibility of 3D noninvasive imaging of labor uterine contractions using EMMI in a clinical setting, the following experiments were conducted.

A. Design of MRI Patch and Electrode Patch

In one aspect, MRI and electrode patches may be fabricated using a protocol as described below. Templates of MRI and electrode patches may be produced on printing paper using a design similar to the template illustrated in FIG. 5A. Using the templates, MRI and electrode patches may be cut from clear vinyl and silicone rubber sheets. Each rectangular patch may have dimensions of 120 mm by 60 mm as illustrated in FIG. 5A, and/or square patches with dimensions of 60 mm by 60 mm.

To produce the MRI patch, a template as described above may be overlaid with a clear vinyl patch. MRI-compatible markers such as Vitamin E liquid softgels may be positioned on the vinyl patch at the circle centers of the template and fastened to the vinyl patch surface, as illustrated in FIG. 5B.

To produce the electric patch, the circle locations of the template of FIG. 5A may be marked on the silicone rubber patch and holes may be punched at each location. Electrode holders may be positioned over each hole and attached using a double-sided adhesive collar, with the center of each electrode holder aligned with the center of each hole on the silicone rubber. An X-ring and a pin-type active electrode may be assembled within each electrode holder to complete the assembly of each electrode patch. FIG. 5C is an image of an electrode patch in one aspect. Double-sided adhesive strip tape may be applied to the back side of each electrode patches along the long edges of each patch and the patches may be stored for subsequent use.

B. MRI Scanning

In various aspects, the body surface and uterine surface of a patient may be obtained using MRI. MR-compatible marker patches produced as described above (see FIG. 5B) may be placed on the body surface of the patient. For placement of patches on the back surface of the patient, the patient may be positioned in a sitting position on a medical exam bed. A vertical ruler may be placed along the spine of the subject with one end of the ruler positioned at the top of the buttock cleavage. A horizontal ruler may be placed at the level of the patient's iliac crest with the center crossing over the vertical ruler. Rectangular patches may be placed side by side, with the length of each patch aligned with the vertical ruler. The rectangular patches may extend laterally from the intersection of the horizontal and vertical rulers to both lateral sides of the subject in a bilateral symmetric pattern.

For placement of MRI patches on the abdominal surface, the patient may be positioned in a supine position on a medical exam bed with the head of the table elevated to an angle of about 40 degrees. A vertical ruler may be positioned along the midline of the patient's abdominal surface, with the 6-cm mark of the ruler positioned near the fundus region. The center of a horizontal ruler may be attached at the 6-cm mark of the vertical rule, and the horizontal ruler may be attached to the patient's center with each end of the horizontal ruler extending laterally along the natural curvature of the subject's pregnant abdomen. For the upper left abdominal surface, a rectangular patch may be placed with the patch's length positioned above the horizontal ruler and the patch's width positioned next to the vertical ruler. A second rectangular patch may be placed side by side with the first patch along the horizontal ruler. Third and fourth patches may be placed side by side with each patch's length under the horizontal ruler in vertical alignment with the first and second patches, respectively. For the lower left abdominal surface, the rightmost patches may be placed along the vertical ruler, and patches away from the vertical ruler may be placed referring to the above patches. Placement of the right abdominal surface may follow the same procedure as described above for the left abdominal patches. Upon completion of the placement of all MRI patches, photos and notes of the patch layout and readings on the rulers may be recorded for the ruler intersections on the patient's back and navel.

To perform MR scanning, an MR technician may set up an MR scanner (Siemens, VIDA), position the patient on the MRI bed in a supine position, and cover the patient's lower abdomen with a 32-array MRI coil, as illustrated in FIG. 6 at step i. In some aspects, the MRI scan may use the T1-weighted sequence with volume-interpolated breath-hold examination (VIBE) (TR 4.07 ms, TE 1.78 ms, flip angle 10°) and multiplanar reconstruction of the data set (FOV 500×500 mm, matrix 320×320, voxel size 4×1.56× 1.56 mm). The MRI data may be stored in DICOM format for later use as described below.

C. Bioelectricity Mapping and 3D Optical Scan Section

The electricity mapping may be conducted when the cervix dilation of the patient reaches about 4 cm. Each of electrode cavities of the electrode patches described above (see FIG. 5C) may be filled with conductive gel and the release liner of the double-sided tape may be peeled off. The electrode patches may be placed on the patient's back and abdomen following the notes and procedures described above for the MRI patches, avoiding those regions with epidural tapes on the back surface and the TOCO and/or fetal monitors on the abdominal surface. Upon completion of the placement of all electrode patches, photos and notes of the patch layout and readings on the rulers may be recorded for the ruler intersections on the patient's back and navel.

After placing the electrode patches, four grounding electrodes, with "LL" electrode on the left thigh, "LA" electrode on the left shoulder, "RA" electrode on the right shoulder, and "DRL" electrode on abdominal surface near the navel may be placed. Optical 3D scans of the patient's abdominal and lower back surface may be obtained using a hand-held optical scanner to precisely record the locations of the placed electrodes. The electrode patch cables and grounding electrode cables of the bioelectricity mapping hardware (see FIG. 5D) may be connected to the electrode patches and grounding electrodes attached to the patient.

Once the electrode patches and grounding cables are connected, the BioSemi software may be operated using the laptop and the ADC box may be turned on (see FIG. 5D). If the status light is yellow, the grounding electrodes may not have good contact with the patient's skin, the grounding electrode may need repositioned with additional gel and replaced until the status light turns blue.

The BioSemi software may be operated in an Electrode offset mode and electrodes having large offset may be adjusted or repositioned to improve the electrode's contact. A file may be started in the BioSemi software to save the data streams of bioelectricity signals in real-time to obtain a 900-second recording. After completion of the recording, BioSemi the multi-electrode measurements may be stored in a BDF file. Recording may be repeated after checking the status of the subject.

After the last recording, the ADC box may be disconnected, along with the electrode patches, the grounding electrodes, the optical fiber, and USB cable. The electrode patches and the grounding electrodes may then be removed from the subject, and the subject's abdominal and lower back surface may be cleaned with a towel. The electrode patches and grounding electrodes may be stored in cleaning boxes. The electrode patches and grounding electrodes in may be cleaned in a soil room and disinfected with Santicloth. The disinfected electrode patches may be naturally air-dried and taped for subsequent use.

D. Segmentation and Surface Generation of Uterus and Body from MRI Data

The body-uterus geometry may be generated by performing segmentation of the MRI data acquired as described above. Amira software may be launched, loaded with a subject's MR DICOM data, and used to perform segmentation of the uterus within the MRI data and to generate uterine and body surfaces of the subject as described below.

Within the Segmentation module, the "New" icon may be clicked to create a new label, and the "Edit|Adjust range to|Data histogram" icon may be clicked to change the image contrast. Within the Sagittal View, the Brush tool may be selected to label the uterus boundaries of the MR images, fill the region, and add to the label file. This segmentation step may be repeated every 3-5 sagittal slices. After manual labeling for uterus boundaries, the segmented regions may be selected and interpolated to generate uterus segmentation over all slices of the data to complete segmentation of the uterine surface.

After creating a new label, the Magic wand tool may be used to set the threshold of the masking created above at the first local minimum of the data histogram, and refine the threshold until the whole body is highlighted in blue. After selecting all slices, any blue region may be selected, and the body segmentation may be added into the label file. Segmentation|Fill holes|All slices|+ may be used to fix any holes within the body segmentation.

The Project module may be used to generate the surface data from the label files of uterus and body surface. After choosing a surface file, Simplification Editor may be used to reduce the face number of the surface by 50%. After applying parameters to Smooth Surface (iteration=20, lambda=0.6), the selected surface may be remeshed. The uterine and body surfaces may be simplified and remeshed in an iterative manner until the body surface has about 18000 faces and the uterine surface has about 640 faces. The final surfaces may be saved in STL format.

E. Generation of Body Surface from Optical 3D Scans

Post-processing of optical 3D scan data may be performed using Artec studio 12 professional. The optical 3D file may be loaded, and the target optical scan may be selected and duplicated. The selected scan may be post-processed using the Autopilot module. In the model creation module, various scan parameters may be selected including, but not limited to, scan quality (geometry, texture), object size, hole-filling method (Watertight), and any other relevant parameter. After reviewing and erasing redundant regions, an automatic refinement of the scan may be performed, unnecessary regions may be removed, and the resulting surface may be saved in STL format.

F. Alignment of Optical 3D Scans and MRI Data

In-house developed TCL scripts for Amira may be used to align the optical 3D scan data to the MRI surface and generate the body-uterus geometry. The STL format surfaces generated above may be loaded into the pre-programmed Amira project. The prompt TCL command line may be run in the command line to prepare Amira objects for rigid alignment for the abdominal surface. Two Viewers (horizontal) may be selected, and the visibility of Artec-torso may be enabled in the left viewer and the MRI-isosurface may be enabled in the right viewer. 5-6 landmarks may be placed on both surfaces accordingly and the prompt TCL command line may be run to apply the rigid alignment. This rigid alignment may be repeated for the back surface.

Enabling only the visibility of the rigid-aligned Artec-torso surface in a single viewer, the prompt TCL command line may be run to prepare Amira objects for non-rigid alignment. Landmarks corresponding to electrode locations may be added on the optical 3D scan surface and MRI body surface. The landmark files may be stored for non-rigid alignment.

The MATLAB function may be used for subsequent non-rigid alignment. The prompt TCL command line may be run to import the auto-aligned electrode landmarks and to refine electrode landmarks based on notes and photos taken during the MRI scan as described above. The refined landmarks may be exported as landmarks files for the electrode locations, and the MATLAB function may be run to generate the body-uterus geometry in MAT format.

G. Electrical Signal Preprocessing

MATLAB may be used to run an in-house developed EMG pre-processing MATLAB function. The file name and electrode patches placed on the body surface may be input and saved. An in-house developed artifacts detection MATLAB function may be used to automatically detect the local and global artifacts.

H. Uterine Electrical Signal Reconstruction and Characterization

After the body-uterus geometry is generated and electrical signal is preprocessed, these data may be loaded into MATLAB, and an in-house developed EMMI reconstruction MATLAB function may be used to compute the electrical signals on uterine surface. An in-house developed EMG burst analysis MATLAB function may be used to automatically detect the onsets and offsets of each EMG burst. An observation window may be selected on the overlay cluster figure, the activation time at each uterine site during each observation window may calculated, and the isochrone of each observation window may be generated.

I. Representative Results

Bioelectricity mapping hardware is shown in FIG. 5D and the connection of each component is marked in detail. FIG. 6 is a flowchart illustrating the procedures implemented using the disclosed EMMI system, which includes the MRI scan of the subject wearing MRI patches at step i, the 3D optical scanning at step ii, the bioelectricity mapping at step iii, the generation of body-uterus geometry at step iv and the schematic results of EMMI at step v as described above.

Figure 7A:
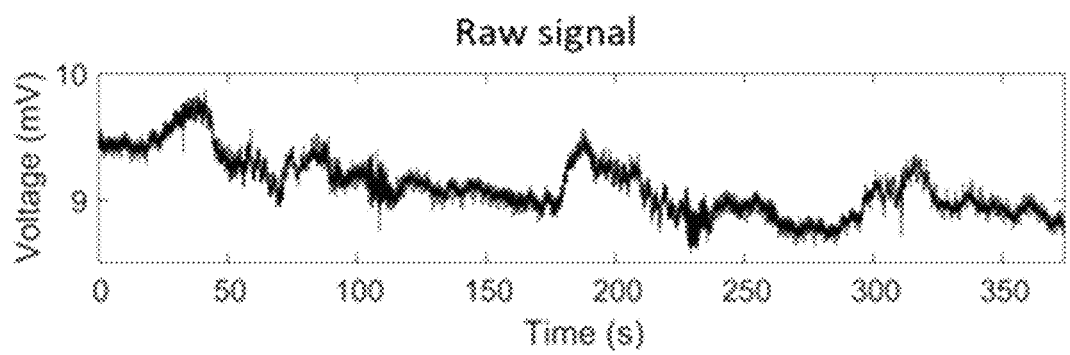
FIG. 7A is a graph of a 375-second raw signal recorded from a pin-type electrode on the body surface.
Figure 7B:
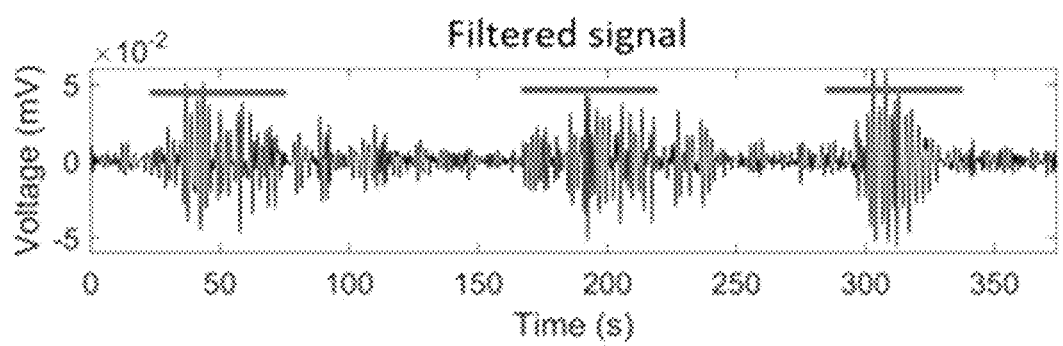
FIG. 7B is a graph of the raw signal of FIG. 7A after application of Butterworth Lowpass filtering, downsampling, and Butterworth high pass filtering; green lines mark the locations of EMG bursts.

FIG. 7A shows a raw body surface electrogram, obtained using a sampling rate of 2048 Hz. The raw signal is severely contaminated by the baseline drift, maternal EKG, maternal breathing, etc. A fourth order Butterworth high pass filter with a cut off frequency at 0.34 Hz, an eighth order Butterworth low pass filter with a cut off frequency at 40 Hz, a down sample by 20 times, and an eighth order Butterworth low pass filter with a cut off frequency at 1 Hz were applied to generate a filtered signal shown in FIG. 7B. Three clear EMG bursts are marked with green lines in FIG. 7B.

Figure 8A:
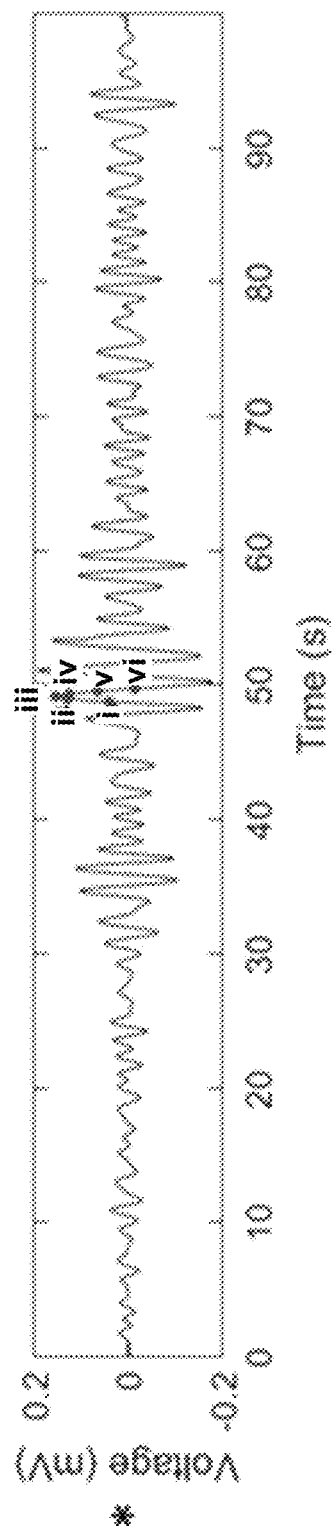
FIG. 8A is an electrogram obtained at an electrode position marked by an asterisk in the anterior view of row i in FIG. 8B.
Figure 8B:
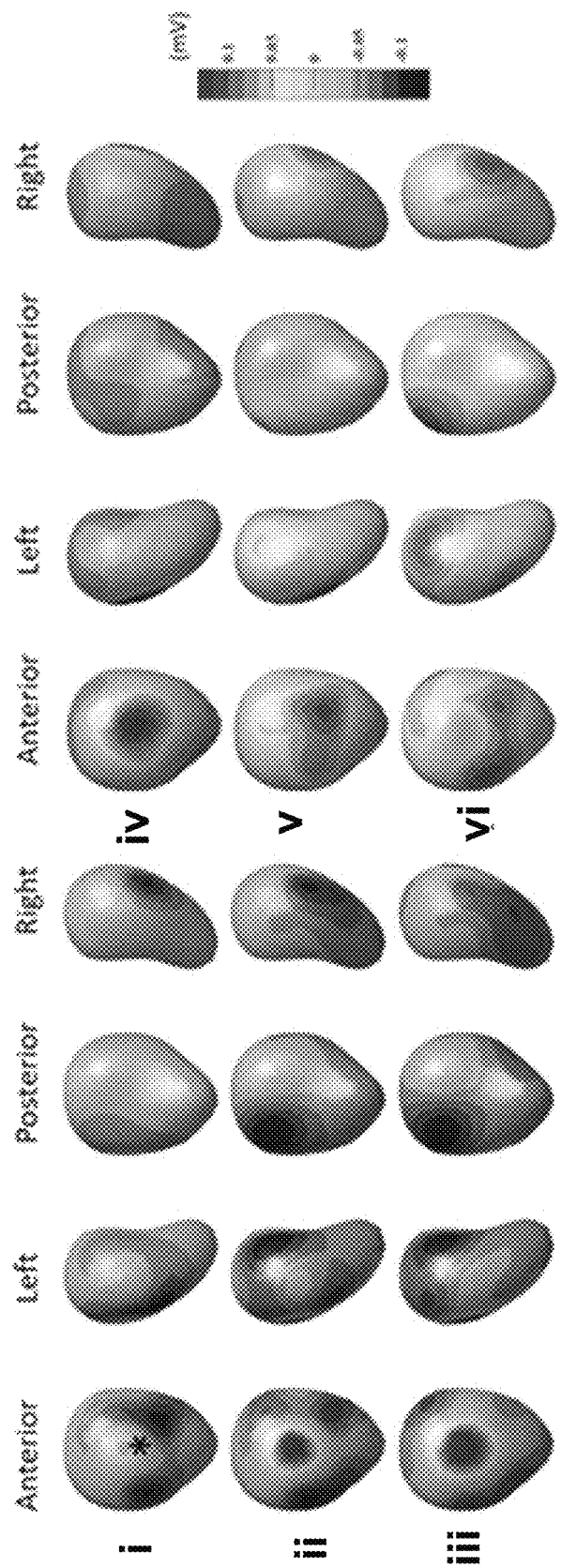
FIG. 8B includes potential maps corresponding to various times labeled as red dots on the electrogram of FIG. 8A.

FIG. 8B shows six successive uterine surface potential maps (labeled i, ii, iii, iv, v, and vi) with 0.2 s temporal space in anterior, left, posterior and right view. The warm color represents positive potentials and cool color represents negative potentials. The respective time of each uterine potential is labeled in the electrogram of FIG. 8A, which was obtained from the star site labeled in FIG. 8B, map i. A positive region at the star site in map i of FIG. 8B initially appears, enlarges in maps ii, iii, iv, and v of FIG. 8B, and diminishes in map vi of FIG. 8B, demonstrating that EMMI was able to show the dynamic progression of the uterine contractions in 3D with the potential maps.

Figure 9A:
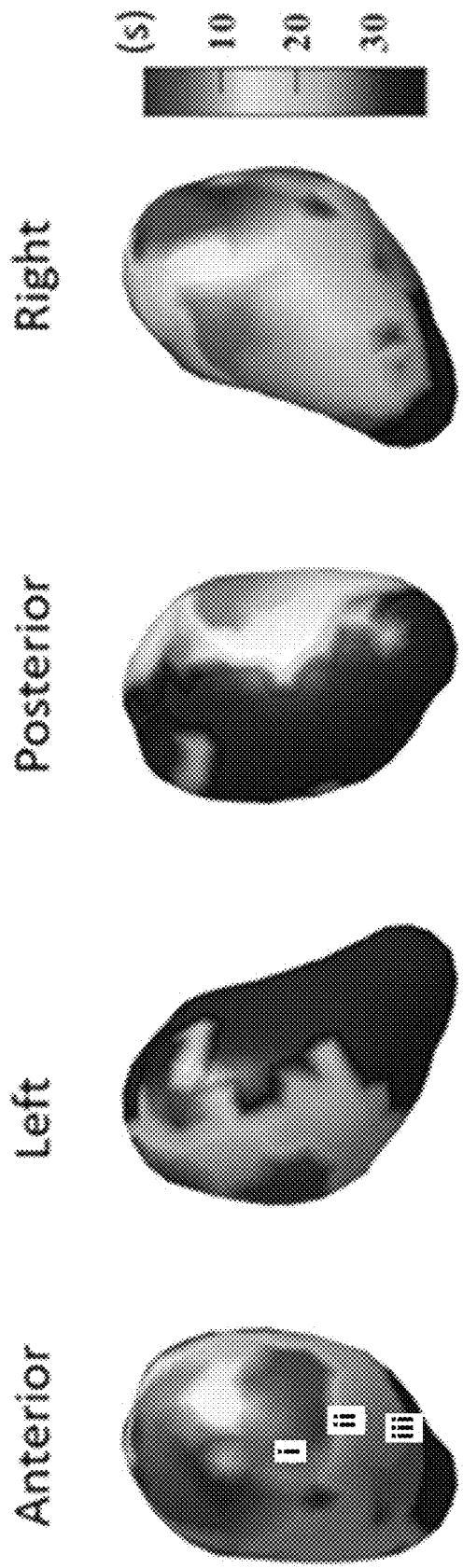
FIG. 9A contains four views of an isochrone map with warm (red) color representing early activation, cool (blue) color representing late activation, and dark blue representing non-activation.
Figure 9B:
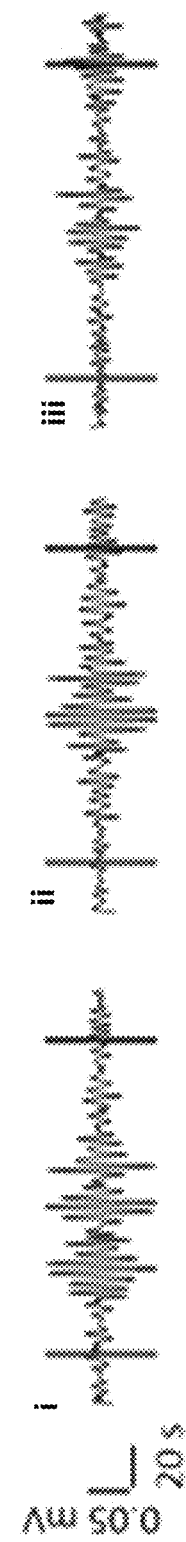
FIG. 9B contains uterine electrograms from sites I, ii, and iii shown marked in the anterior view isochrone map of FIG. 9A; red and blue vertical lines mark the start and end of the observation window for this isochrone.

FIG. 9A shows the isochrone maps within an observation window marked by blue and red vertical lines in FIG. 9B. The warm (red) color represents early activation, cool (blue) color represents late activation, and dark blue represents no activation in the specific observation window. The isochrone map of FIG. 9A displays an activation sequence where the uterine contraction initiates at the right fundus of the uterus, and propagates to the anterior and right of the uterus, while the left posterior of the uterus is relatively quiet. Three representative uterine electrograms from sites labeled I, ii, and iii are shown in FIG. 9B. The EMG burst at site i is active earlier than the corresponding EMG bursts at sites ii and iii, which is summarized in the isochrone map of FIG. 9A. This result demonstrates that EMMI can show the uterine contraction sequence, simplifying the location of leading contraction regions.

Example 3: Spatial-Dependent Regularization to Solve the Inverse Problem in Electromyometrial Imaging To develop and validate a spatial-dependent (SP) regularization method to improve EMMI's accuracy, the following experiments were conducted. The SP method was developed using a spherical geometry with a current dipole source to calculate site-specific regularization parameters based on the eccentricity of body-uterus geometry and SNR of body surface signals. A realistic uterus model with multiple dipole sources was employed to validate the SP method. The reconstruction accuracy of the SP method was compared to those of the CRESO and the L-Curve methods in terms of electrograms and potential maps.

Several methods have been developed to clinically monitor uterine contractions, such as tocodynamometers, which measure body surface contour displacements caused by uterine contractions, and intrauterine pressure catheters. However, the latter method is invasive and poses maternal and neonatal risks, and neither method can assess uterine contractility at high spatial and temporal resolution. In a non-clinical method, electromyography (EMG), 4 to 64 electrodes are placed on a small region (around 4 cm by 4 cm) of the body surface and used to monitor myometrial electrical activity. EMG measured electrical signals preceding uterine contractions can predict preterm birth. However, EMG cannot provide sufficient spatial resolution and coverage to reflect the detailed uterine electrophysiological patterns during contractions. Thus, we cannot answer basic questions such as where uterine contractions initiate, whether they always propagate in the same manner and speed, how contractions in different uterine regions correlate with one another, and what differentiates productive (leading to labor and delivery) contractions from non-productive preterm contractions.

Figure 18:
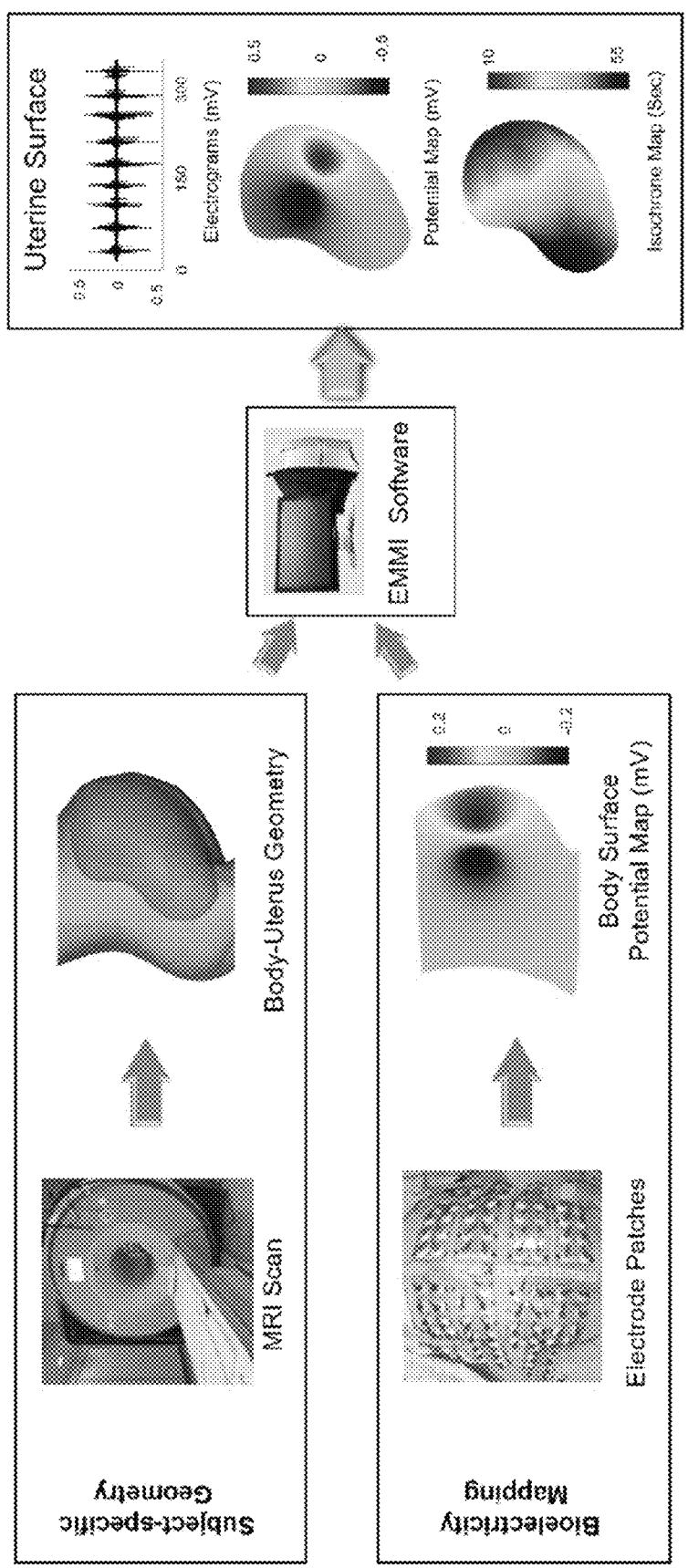
FIG. 18 is a schematic diagram illustrating elements of an EMMI method for monitoring uterine contractions in accordance with an aspect of the disclosure.

To address this limitation, we developed electromyometrial imaging (EMMI). In EMMI, a subject wearing magnetic resonance imaging (MRI) markers undergoes MRI to derive a body-uterus geometry (FIG. 18). Then, when the subject is in labor, up to 256 electrodes (in the same positions on the body surface as the MRI markers) are used to measure EMG and generate body surface potential maps. Next, EMMI software solves an inverse problem (the Cauchy problem) to combine the subject-specific body-uterus geometry with the measured body surface EMG and thus reconstruct uterine surface electrical potentials. EMMI is based on a similar method used to monitor heart activity, electrocardiographic imaging (ECGI).

Because the inverse reconstruction procedure underlying both EMMI and ECGI is ill-posed, a small amount of noise in the measured body surface electrical signals could cause large errors in the reconstructed electrical signals on the uterine or heart surface. To stabilize the inverse computation underlying ECGI, several regularization methods have been proposed. The most widely used is the zero-order Tikhonov (ZOT) regularization method, with composite residual and smoothing operator (CRESO) determining a global regularization parameter, $\lambda$, which is applied to all sites on the heart. This method is also used in EMMI. However, because the same $\lambda$ is applied to all heart/uterine sites, under-regularization could occur for some sites, and over-regularization could occur for other sites, impairing re-construction accuracy. For example, a spherical geometry model was previously used to demonstrate the optimal $\lambda$ in EMMI will differ depending on the distance between a site on the heart surface and the nearest body surface site. This under- and over-regularization is likely a more severe problem for EMMI than for ECGI because the uterus is farther from the center of the body along the anterior-posterior axis than is the heart.

One approach to solving this problem is to use optimized for each uterine site. However, no methods have been developed to compute site-dependent. Here, we developed and tested a spatial-dependent (SP) method to compute site-specific for EMMI, which can also be applied to ECGI. We show that the SP method produces more accurate EMMI reconstructions than the CRESO or L-curve methods.

A. Materials and Methods

Zero-order of Tikhonov regularization method: EMMI reconstructs uterine surface potential maps (USPMs) during uterine contractions by combining the body surface potential maps (BSPMs) and subject-specific body-uterus geometry segmented from MRI images. The basic mathematical formulation underlying this inverse problem can be described by Laplace's equation in three-dimensional space (1) and two types of boundary conditions on the body surface (2, 3).

$$\phi(x) = \phi_B(x), x \in \Gamma_B \quad (1)$$

$$\text{Dirichlet condition } \nabla^2 \phi(x) = 0, x \in \Omega_{UB} \quad (2)$$

$$\text{Neumann condition } \sigma_{\Omega_{UB}} \frac{\partial \phi(x)}{\partial n} = 0, x \in \Gamma_B \quad (3)$$

$\Gamma_B$ represents the body surface, $\varphi B$ (x) is the BSPM on the body surface at location x, and n denotes the normal direction to the boundary of $\Gamma_B$. $\sigma\Omega_{UB}$ is the conductivity of the volume between the uterine surface and the body surface, ΩUB, and is assumed to be homogeneous. Because the conductivity of air, the right side of (3) is zero.

According to Green's theorem, equations (1, 2, 3) can be discretized by the boundary element method. As shown in (4), BSPM and USPM, φU, are associated by transfer matrix A, which encodes the subject-specific body-uterus geometry $$\varphi B = A \varphi U \quad (4)$$

Because transfer matrix A is numerically ill-conditioned, the inverse problem cannot be solved by directly inverting matrix A. A well-established technique for such cases is the ZOT regularization method, which solves a least-square problem with an $L_2$ norm regularization term, shown as (5), where is λ a positive scalar regularization parameter.

$$\min_{\lambda>0}\{\|A\phi_U - \phi_B\|^2 + \lambda\|\phi_U\|^2\} \quad (5)$$

In the ZOT method, a singular value decomposition (SVD (6)) is implemented.

$$A = U\Sigma X^T \quad (6)$$

where U is an M×M matrix with columns that are singular vectors spanning the data space $\varphi_B$, and X is an N×N matrix with columns that are singular vectors spanning the model space $\varphi_U$. M and N represent the numbers of body and uterine surface sites, respectively. Σ is a diagonal matrix of singular values $\sigma_i$, where $\sigma_1 \geq \sigma_2 \geq \ldots \geq 0$ and i=1, 2, ..., $\sigma_{min}\{M,N\}$.

The inverse solution of the ZOT method is represented by SVD components, shown as (7).

$$\Phi_U = \sum_{i=1}^{q} \frac{\sigma_i^2}{\sigma_i^2 + \lambda} \frac{U_{\cdot,i}^T \phi_B}{\sigma_i} X_{\cdot,i} \quad (7)$$

where λ is the ZOT regularization parameter, q is the number of non-zero singular values, and i indicates the $i_{th}$ singular value, $\sigma_i$. $U_{\cdot,i}$ represents the $i^{th}$ singular vector of matrix U, which is correlated with $\sigma_i$. Similarly, $X_{\cdot,i}$ represents the $i^{th}$ singular vector of matrix X. We define $d_i$ as a decomposition of the body surface potential $\varphi_B$ onto singular vectors of U, shown in (8).

Substituting (8) into (7), $$\Phi_U = \sum_{i=1}^{q} \frac{\sigma_i^2}{\sigma_i^2 + \lambda} \frac{d_i}{\sigma_i} X_{\cdot,i} \quad (9)$$

Traditional methods to determine the regularization parameter, λ: In (9), φU can be regarded as the linear weighted summation of the singular vectors $X_{\cdot,i}$, i=1, 2, ..., q, where the linear coefficients are determined by $d_i$ and $\sigma_i$. The two values are derived from SVD components and body surface measurements. If λ is not optimized, the inverse solution will likely be over- or under-regularized. The CRESO and L-Curve methods are widely used empirical method to determine the λ for ZOT regularization in ECGI. The CRESO method aims to determine the smallest positive λ that results in the maximum of C(λ), as shown in (10). The L-Curve method locates the "corner" of the L-shaped curve which indicates the relationship between the norms of φU and residual AφU-φB in a log-log plot with λ as a variable.

$$\max_{\substack{\lambda>0 \\ \min\lambda}}\left\{C(\lambda) = \frac{d}{d\lambda}[\lambda\|\phi_U\|^2] - \frac{d}{d\lambda}[\|A\phi_U - \phi_B\|^2]\right\} \quad (10)$$

3) Spatial dependent (SP) method to determine λ: Based on the SVD components (7), we formulated the inverse solution of the SP method as (11), where k is $k^{th}$ site on the uterine surface, $\lambda_k$ is the regularization parameter of potentials for the $k^{th}$ uterine site, and q is the number of non-zero singular values. $\lambda_{SP}$ is determined by the distance from uterine sites to body surface, L, which is calculated from the body-uterus geometry and the signal-to-noise ratio (SNR) of the BSPMs (12).

$$\phi_{U_k} = \sum_{i=1}^{q} \frac{\sigma_i^2}{\sigma_i^2 + \lambda_k} \frac{d_i}{\sigma_i} X_{k,i} \quad (11)$$

$$\lambda_{SP} = [\lambda_1, \lambda_2, \ldots, \lambda_k, \ldots, \lambda_N]^T = f(L, SNR) \quad (12)$$

where k=1, 2, ..., N, where N is the number of uterine sites, i is the index of singular vector.

B. Bio-Electricity Simulation

Geometries setup: We modeled a three-layer spherical geometry (FIG. 19A) in which the inner-most, middle and outer layers represented the intrauterine space, myometrium, and the body surface, respectively. The radius of each layer was based on the average size of a pregnant woman at 9 months' gestation (Table I). To validate SP method, we used a non-spherical uterus geometry, RPI-9 (FIG. 19B), developed by the Rensselaer Polytechnic Institute to model of a woman at 9 months' gestation. To simplify the bio-electric simulation and generate a closed-shape body surface geometry, an ellipsoid with similar size as the abdominal and lower-back surface of the 9-month pregnant woman was set as the body surface (FIG. 19C). In both geometries, the intrauterine surface was derived by shrinking the uterine surface by 30 mm along the normal direction. We defined 900 uterine sites and 1400 body surface sites for both geometries (FIGS. 19A and 19B). Anterior uterine sites (large index) are closer to the body surface, and posterior uterine sites (small index) are farther from the body surface. We formatted the distances from uterine sites (e.g. point i in FIG. 19C) to their nearest body surface sites (e.g., point ii in FIG. 19C) to L. FIGS. 20A, 20B, 20C, and 20D show the distribution of L in the spherical geometry.

Physics setup: The volumes and surfaces of body-uterus geometry are shown in a two dimensional schematic (FIG. 19C). The volume spaces, $\Omega_{UB}$, $\Omega_{AU}$, and $\Omega_A$ represent the volume conductor between the uterine and body surfaces, the myometrium, and the amniotic fluid, respectively, with respective conductivities $\sigma\Omega_{UB}$, $\sigma\Omega_{AU}$, and $\Omega_A$. $\Gamma_B$ and $\Gamma_U$ represent body and uterine surfaces, respectively. Table I lists the conductivity values for each volume space.

TABLE I

| Bio-electricity Simulation Parameters | | | |
|---|---|---|---|
| Geometry Setting | | Conductivity Setting | |
| Radius | Value | Conductivity | Value |
| $R_A$ | 13 cm | $\sigma_{\Omega_A}$ | 0.5 S/m |
| $R_U$ | 16 cm | $\sigma_{\Omega_{AU}}$ | 1.74 S/m |

TABLE I-continued

Bio-electricity Simulation Parameters

| Geometry Setting | | Conductivity Setting | |
| --- | --- | --- | --- |
| Radius | Value | Conductivity | Value |
| $R_B$ dis $(O_U, O_B)$ | 27 cm 9 cm | $\sigma_{\Omega_{UB}}$ | 0.2 S/m |

Similar to the electrical activity preceding cardiac contractions, the electrical activity preceding uterine contractions can also be represented by current dipoles. The current dipole was placed at the intrauterine surface $\Gamma_A$ to simulate local myometrial contractions. The current dipole directions were set along the normal direction of the intrauterine surface as well as the two tangent directions (arrows in FIG. 19A). Single current dipoles (constant magnitude, Table II) were sequentially placed on all discrete sites on $\Gamma_A$ to simulate a time series of BSPMs and USPMs. To simulate complex uterine contractions, multiple current dipoles with random tangent directions were placed at random locations on the intrauterine surface $\Gamma_A$. The magnitudes of the dipoles were set as a sine wave with frequency 0.5 Hz (Table II), which is the mean frequency of uterine contractions during active labor. To model measurement noise, white Gaussian noise was added to the simulated BSPMs. Simulated USPMs were considered as the ground truth for the reconstructed USPMs. COMSOL multi-physics finite element modeling software (COMSOL Multiphysics, version 5.3a) was used to implement this simulation.

TABLE II

Bio-electricity Simulation Equations

| | | |
| --- | --- | --- |
| Current Conservation | | $\nabla \cdot J = Q_{j,v}$ |
| | | $J = \sigma E + Je, \Omega_A, Q_{U\ B}, Q_{AU}$ |
| | | $E = -\nabla V$ |
| Electrical Insulation | | $n \cdot J = 0, \Gamma_B$ |
| Single Current Dipole | Magnitude | $p = 10^{-5}$ A-m |
| | Direction | Normal, tangent |
| | Position | Each site on intrauterine surface |
| Multiple current Dipoles | Magnitude | $p = 10^{-5} \sin(2\pi ft)$ A-m |
| | Frequency | $f = 0.5$ Hz |
| | Sampling rate | $Fs = 10$ Hz |
| | Direction | Random tangent |
| | Position | Random site on intrauterine surface |

C. To quantitatively evaluate the accuracy of inverse re-construction, uterine electrograms and potential maps were reconstructed with CRESO, L-Curve, or SP methods and then compared with the ground truth by using correlation coefficients (CC) and relative error (RE), defined as follows:

$$CC = \frac{\sum_{i=1}^{n}\left(V_i^T - \overline{V^T}\right)\left(V_i^R - \overline{V^R}\right)}{\sqrt{\sum_{i=1}^{n}\left(V_i^T - \overline{V^T}\right)^2}\sqrt{\sum_{i=1}^{n}\left(V_i^R - \overline{V^R}\right)^2}} \quad (13)$$

$$RE = \sqrt{\frac{\sum_{i=1}^{n}\left(V_i^T - V_i^R\right)^2}{\sum_{i=1}^{n}\left(V_i^T\right)^2}} \quad (14)$$

For electrograms, n denotes the number of time frames within the electrograms. $V^T$ and $V^R$ are the $i^{th}$ time frame of true uterine potentials and reconstructed uterine potentials, respectively. $\overline{V^T}$ and $\overline{V^R}$ are the average true and reconstructed, respectively, uterine potentials over all time frames. For potential maps, n is the number of uterine surface sites. $V_i^T$ and $V_i^R$ are the true and reconstructed, respectively, uterine potentials at the $i^{th}$ uterine site. $\overline{V^T}$ and $\overline{V^R}$ are the average true and reconstructed, respectively, uterine potentials over all uterine sites. A CC value close to 1 indicates high morphology similarity, and a RE value close to 0 indicates low magnitude error.

D. Methodology to Compute ASP

Figure 20A:
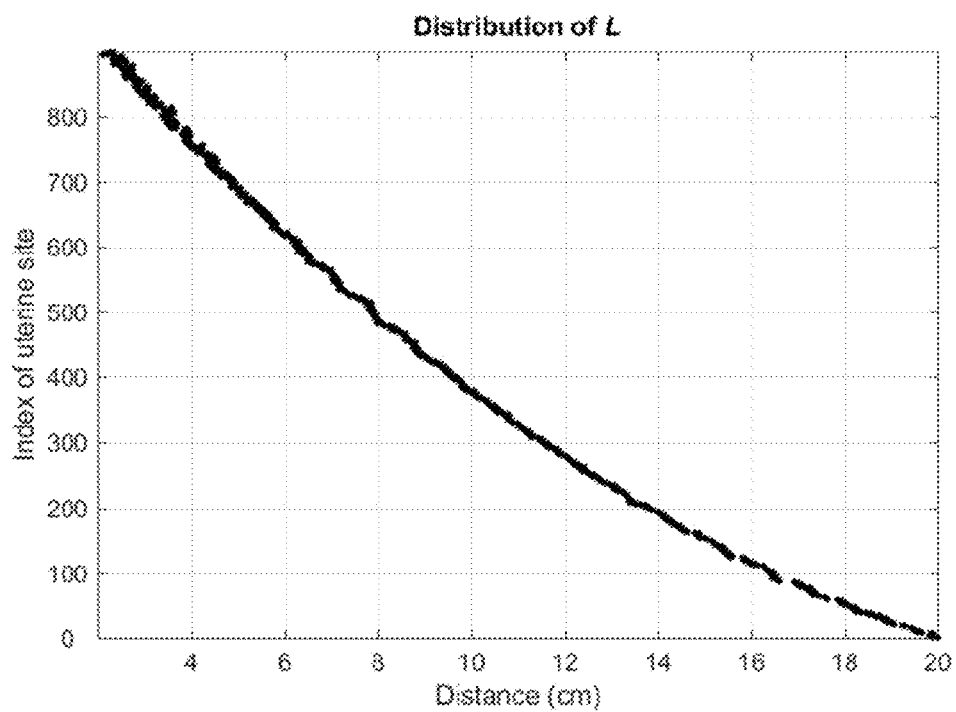
FIG. 20A is a graph showing a distribution of distances from uterine sites to nearest body surface sites (L) in the three-layer spherical geometry of FIG. 19.
Figure 20B:
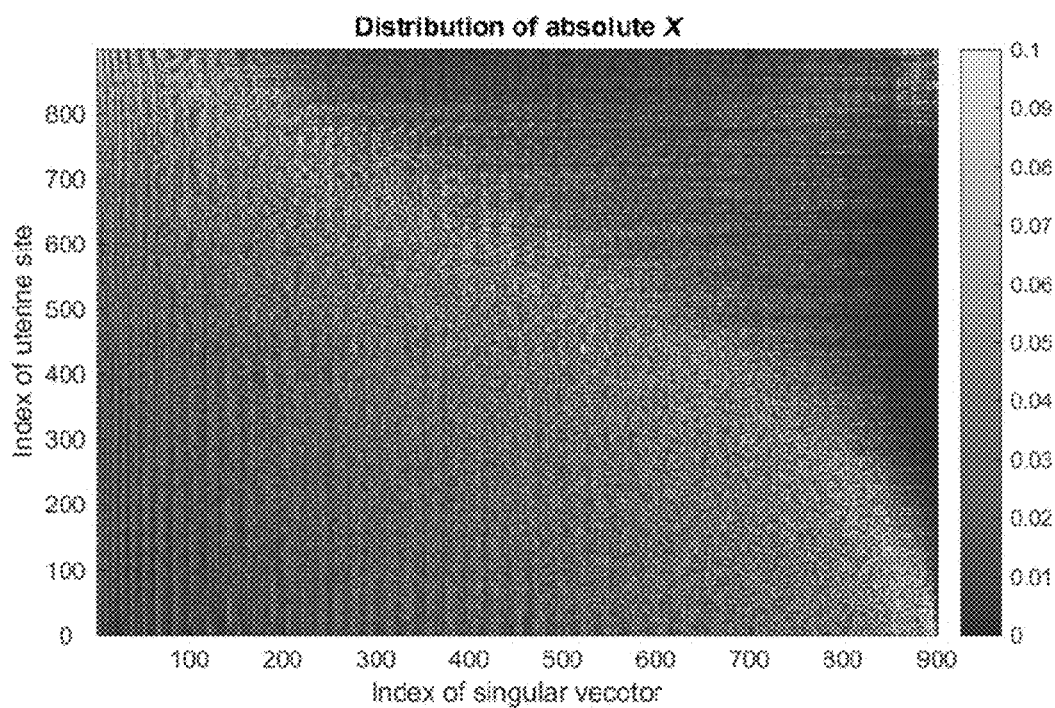
FIG. 20B is a graph showing a distribution of absolute values of X. Columns are the singular vectors, and rows correlate with uterine sites. Yellow color and blue color represent large and small values, respectively.

1) Definition of power threshold function: The distribution of absolute X (6) values for the spherical geometry (FIG. 19A) is shown in FIG. 20B. Because each row of X is associated with potentials at each uterine site (11), and the distribution of X values at each row is different (FIG. 20B), site-specific λ values are needed for an accurate inverse computation. Specifically, the larger absolute X values of anterior sites (row index 600 900) are distributed within lower indexed singular vectors, and larger absolute X values of posterior sites (row index 1~300) are located within higher indexed singular vectors.

We used the ZOT method to consider all singular values (σ) of transfer matrix A as candidate regularization parameters to reconstruct a series of uterine potentials from BSPMs. The optimal uterine surface site-specific $\lambda_k$ was defined as the singular value $\sigma_{i(k)}$ that maximized the CC value between the reconstructed and true electrograms at the $k^{th}$ uterine site, where i(k) denotes the index of the correlated singular value $\sigma_{i(k)}$. We defined the optimal energy level at each uterine site as (15, 16):

$$p_k = \sum_{i=1}^{i(k)} X_{k,i} \quad (15)$$

$$p = [p_1, p_2, \ldots, p_k, \ldots, p_N]^T \quad (16)$$

where $p_k$ denotes the power threshold value of the $k^{th}$ uterine site and N is the number of uterine sites.

To assess the relationship between optimal energy level and L, we simulated body surface potentials with 100 levels of white Gaussian noise, with average peak-to-peak magnitude from 8% to 32% and spherical geometry (FIG. 19A). We calculated the optimal energy level p for each set of BSPMs and then computed the Pearson CCs between the optimal energy level and L. p was negatively linearly related with L with mean CC lower than 0.8. Therefore, we named the optimal energy level as the power threshold and defined a power threshold function as (17).

$$p' = a \times (b - \ell) \quad (17)$$

where p' represents power threshold of all uterine sites, a and b are variables, and $\ell$ represents normalized L to the length of one.

Next, we calculated optimal parameters of a and b at each noise level by using the least-squared method to minimize the error between p and p'. The optimal parameters of the 100 sets of BSPMs are a=3.46±0.78, b=2.2±0.14, and fitting accuracy (18) $R^2$=67%±6.5%.

$$R^2 = 1 - \frac{\sum_k (p_k' - p_k)^2}{\sum_k (p_k - \bar{p})^2} \quad (18)$$

where k=1, 2, ..., N denotes the index of uterine site, p and p' represents optimal and defined power threshold, and $\bar{p}$ represents the mean value of optimal p values. The $R^2=1$ means no fitting error.

Based on the standard deviation of a and b, b changes slightly. Then, we set b as its mean value, 2.2, and used the same least square method to find optimal a. The fitting accuracy $R^2$ of b as a variable and as a constant were compared, and the difference of $R^2$ is 0.4%±0.37%, which only decreases slightly when b was set as the mean value. Therefore, b was set as a constant with the value of mean b=2.2 and a was set as a variable. Then, power threshold function becomes (19).

$$p'=a\times(2.2-\ell) \tag{19}$$

$$a=h(L,SNR) \tag{20}$$

where a is a variable, which is related to the body-uterus geometry and measured signal quality derived above.

The optimal $p_k$ is paired with optimal $\lambda_k=\sigma_{i(k)}$ (15). If we can determine p' values, then the boundaries connecting points [i'(k), k], k=1, 2, ... N, where summation of $X_{k,i}$, i=1, 2, ..., i'(k) equals its correlated power threshold $p'_k$ could be extracted, and i'(k) denotes the index of singular vectors. The median values of the boundaries at each row were then smoothed with a window size 5% of the number of uterine sites to determine a set of [i(k), k], k=1, 2, ... N, where i(k) is the index of singular vector. This process, which calculates $\lambda_{SP}$ from p' is represented by function g as (21).

$$[i(1),i(2),\ldots,i(k),\ldots,i(N)]^T=g(p') \tag{21}$$

$$\lambda_{SP}=[\lambda_1,\lambda_2,\ldots,\lambda_k,\ldots\lambda_N]^T=[\sigma_{i(1)},\sigma_{i(2)},\ldots,\sigma_{i(k)},\ldots\sigma_{i(N)}]^T$$

Figure 20C:
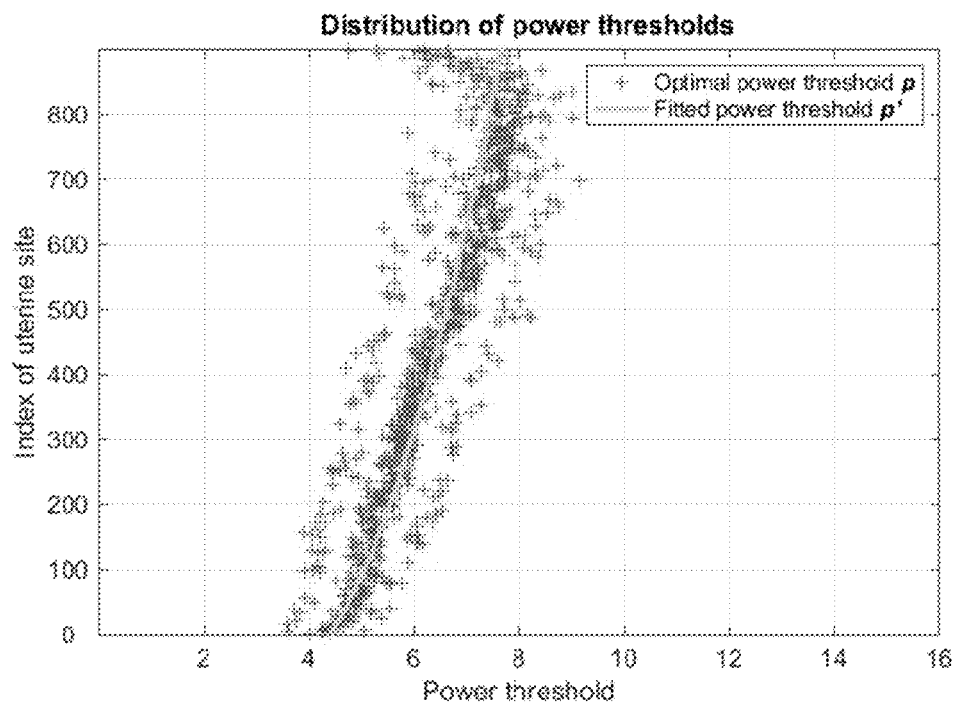
FIG. 20C is a graph showing an example of a distribution of optimal power threshold values and least-square fitted threshold values.
Figure 20D:
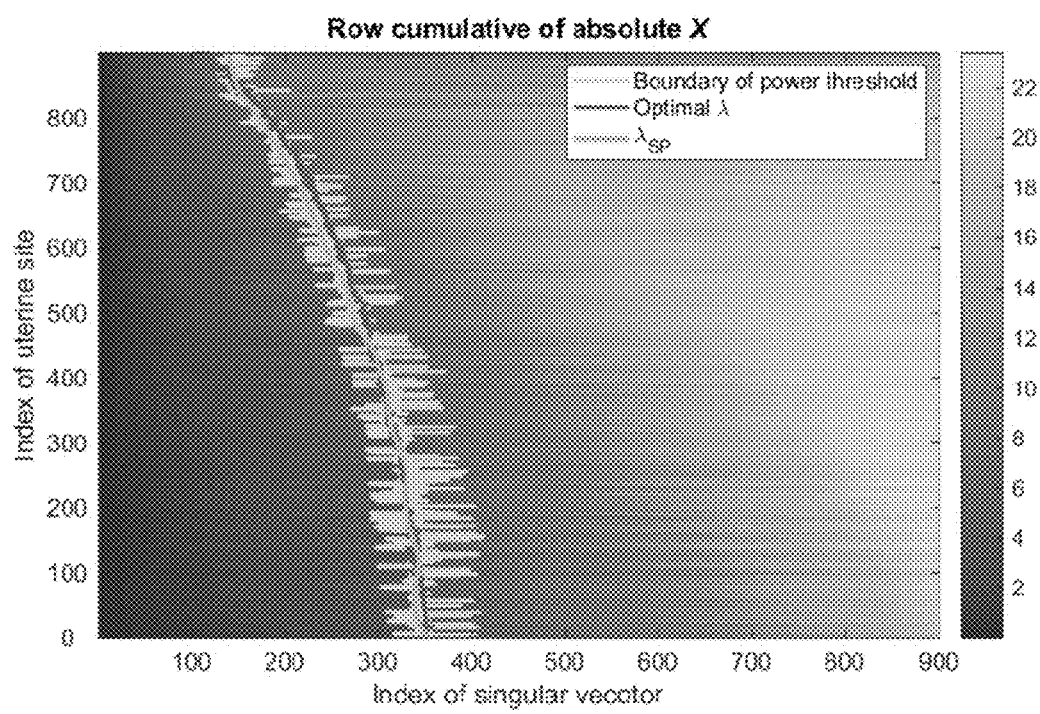
FIG. 20D is a graph showing a row cumulative of absolute X, optimal λ (magenta) and sp (blue). Yellow line represents the boundaries where cumulative X equals fitted threshold values. BSPM used for this power threshold function was generated by adding noise with average peak-to-peak magnitude 15% of the signal.

We use the BSPMs contaminated by noise with average peak-to-peak magnitudes equal to 15% of the signal and the spherical geometry as an example. The optimal power threshold values p of this data set and the best fitted p' of optimal p (generated by the least-mean square method) are shown in FIG. 20C. FIG. 20D shows the cumulative absolute X values along each row, optimal λ, the boundary of points [i'(k), k], k=1, 2, ... N, and $\lambda_{SP}$.

Figure 21A:
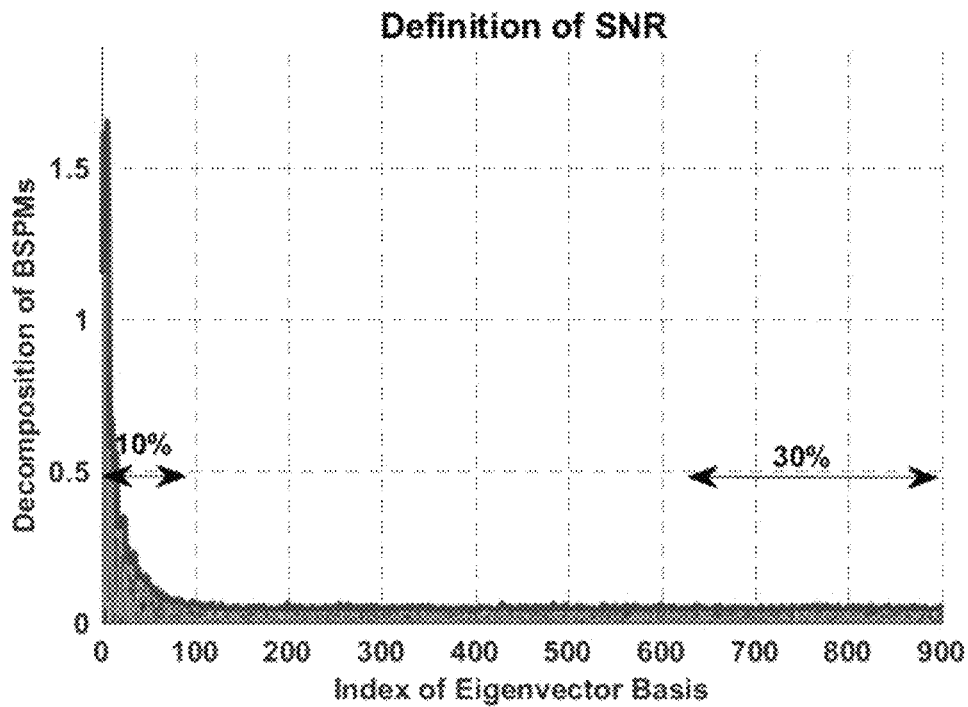
FIG. 21A is a graph illustrating the process of defining SNR of test data set; red line denotes maximum values over all decomposed BSPMs; different colors denote d of the BSPM.
Figure 21B:
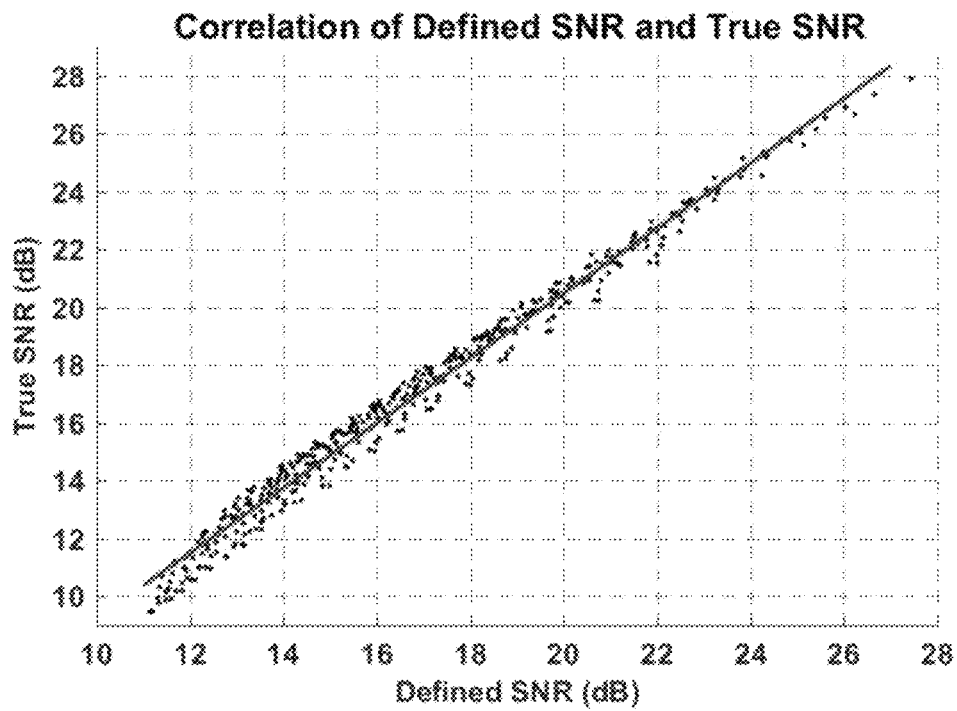
FIG. 21B is a graph showing a linear correlation between defined and true SNRs; $R^2=0.98$.

Derivation of an as a function of L and SN R: We developed a linear regression model to find a for a general geometry and signal. Because pregnant women differ in size and body mass index, the eccentricity of the body-uterus geometry differs for each woman. Therefore, we defined e, the eccentricity of body-uterus geometry (22). True signal-to-noise ratio (SNR, in decibels (dB)) can be calculated with the true signal power and the added noise power using (23), where P represents the power of the signal or the noise. We used decomposed BSPM, d, to calculate the defined SNR. d is a list of decompositions $d_i$ (FIG. 21A). Considering the discrete picard condition for the inverse problem, the mean power of the last 30% of d is defined as noise power $P_{noise}$, and the mean power of the first 10% of d is defined as signal power $P_{signal}$. Then defined SNR for each BSPM can be calculated with (23). FIG. 21B shows the linear correlation between the true SNR and the defined SNR, which are 98% linearly correlated. The SNR of each data set is defined as the mean defined SNRs of all BSPMs.

$$e=\sqrt{\frac{\sum_{k=1}^{N}(L_k-\bar{L})^2}{N-1}} \tag{22}$$

$$SNR=10\log_{10}\frac{P_{signal}}{P_{noise}} \tag{23}$$

Here, 20 spherical geometries were developed with displacement dis($O_U$, $O_B$) from 0 cm to 9 cm, and the other simulation settings in Table I and Table II were unchanged. We then used COMSOL Multiphysics software and a single current dipole to derive paired body and uterine surface potentials under these 20 geometry settings. We also added 20 different levels of white Gaussian noise, with average peak-to-peak magnitude from 25 microvolt to 100 microvolt (8% to 42% of signal) to the body surface potentials. Thus, we generated 400 data sets, each with a pair of body and uterine surface potentials. We then acquired the optimal a, $a_{opt}$, for each data set by using the least-square method to minimize the root-mean-square error of CC values between the reconstructed and true electrograms and potential maps. We calculated the Pearson CCs between $a_{opt}$ and e, and between $a_{opt}$ and SN R, respectively. We found that $a_{opt}$ is linearly related with SN R, (CC 0.94), but is not linearly related with e (CC 0.12). To find a linear model, we defined a new parameter r, the ratio between the area from the y axis to the curve of SP over the total cumulative X area, which is uniquely determined as a nonlinear function of a as (24). We calculated $r_{opt}$ with (24) and computed the CC value between $r_{opt}$ and e and SNR, respectively, which are 0.7 and 0.9. Then we used 90% of the data set with pairs of r e SNR as the linear regression training set and generated the linear regression model as (25) to represent r. The a values could be calculated by (26).

$$r(a)=\frac{\sum_{k=1}^{N}i(k)}{N^2}=\frac{\overline{g(p')}}{N}=\frac{\overline{g(a\times(2.2-l))}}{N} \tag{24}$$

where i(k) is the index of the singular value σi(k).

$$r=q\times[e,SNR,1]^T \tag{25}$$

in which, r represents the area ratio, e represents eccentricity, and q=[0.0015, 0.0113, −0.0254], with $R^2$=0.96.

$$a=\min_{a>0}\{\|r(a)-r\|\} \tag{26}$$

Figure 21C:
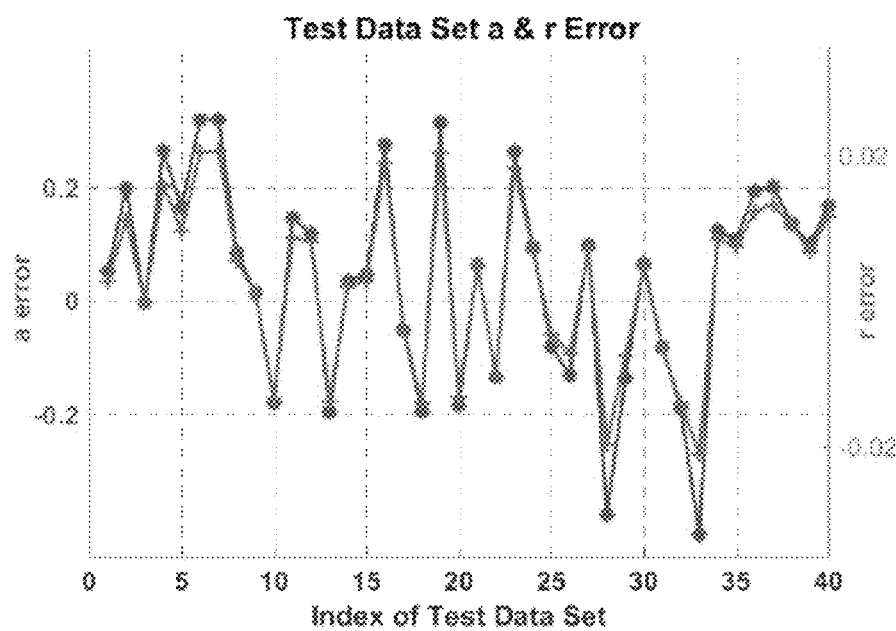
FIG. 21C is a graph showing the test error of parameters a (blue) and r (orange).
Figure 21D:
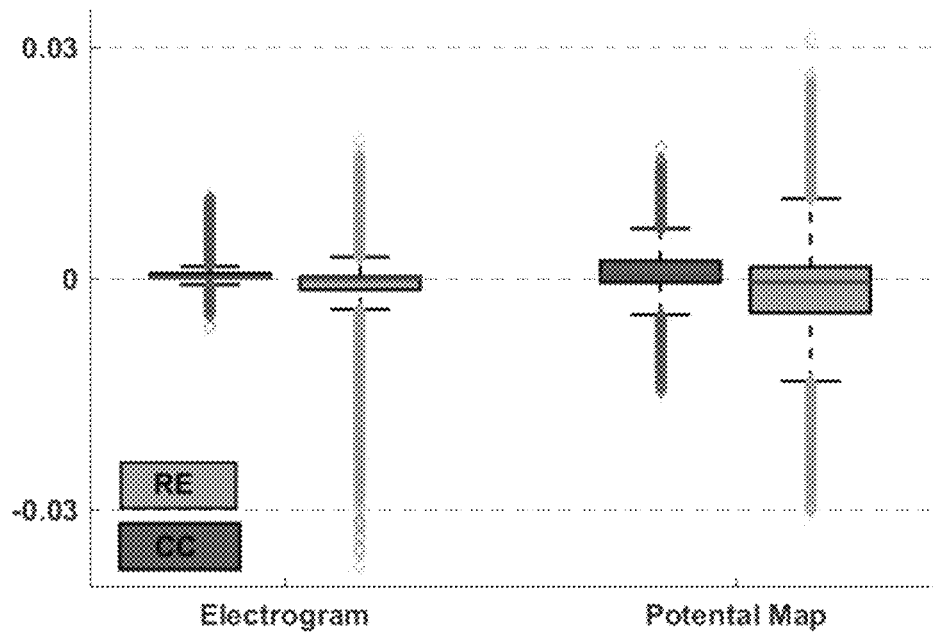
FIG. 21D is a graph showing the test errors of EMMI reconstruction, which are the differences between the CC (blue) and RE (orange) in comparing the reconstructions using optimal parameter a and using linear-modeled parameters r and a. Errors are shown in box-plots showing median (red line), 1st and 3rd quartiles (boxes), whiskers (top and bottom bar are approximately ±2.7 of standard deviation), and outliers (diamonds).

The linear model was applied to the other 10% of the data set, and area ratios r and a were calculated for each data set. We evaluated the errors of parameters a and r by comparing with $a_{opt}$ and $r_{opt}$, reconstructed the related test data sets with linear-modeled a and r, and compared the reconstruction accuracy in terms of CC and RE with the results reconstructed with the best $a_{opt}$ and $r_{opt}$. The errors of the test data set are listed in FIGS. 21C and 21D. There was only a minor error in terms of parameters a and r and in the reconstructed electrograms and potential maps.

E) Data Analysis

We applied the CRESO, L-Curve, and SP method, to simulated BSPMs to reconstruct USPMs. For the SP method, we used power threshold function $p'=a(2.2-\ell)$ (derived above) and linear-modeled parameter r=q[e, SN R, 1]$^T$ (derived above). We then used CC and RE) to compare the reconstruction accuracies of the three methods. Significance of differences was tested with one-sided wilcoxon rank sum tests.

Results

E. Spatial Dependence of Optimal Regularization Parameter

Figure 22A:
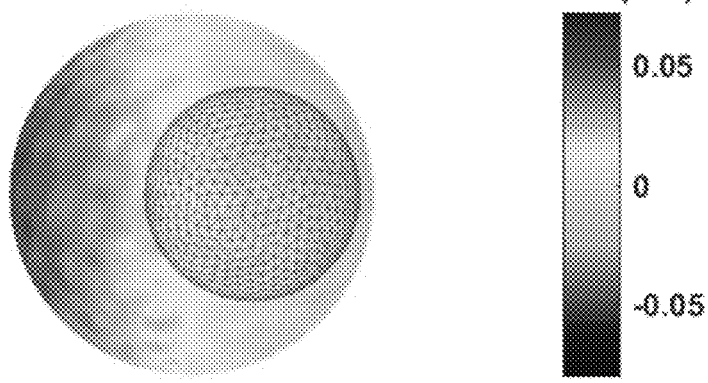
FIG. 22A is a right lateral view of a body surface potential map, where red indicates positive potential and blue indicates negative potential. Black mesh inside the color map is the uterine surface geometry.
Figure 22B:
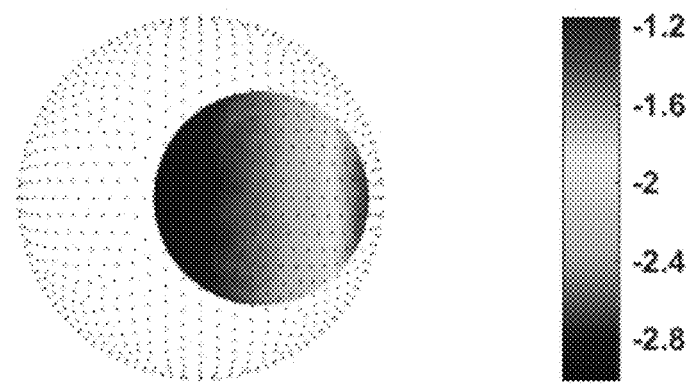
FIG. 22B is a right lateral view of a distribution map of the optimal site-specific k. Blue dots are discrete points on the body surface.
Figure 22C:
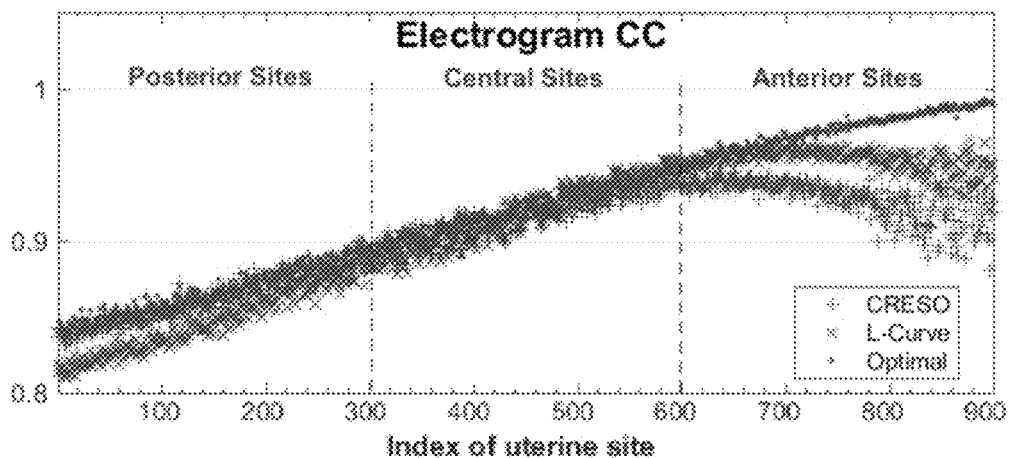
FIG. 22C is a graph showing a reconstructed electrogram CC. Uterine sites with index of 1~300 are at the posterior, and sites with index 601~900 are at the anterior. Potential maps with index 1~900 are correlated with posterior current dipole source, and index 1801~2700 are correlated with anterior current dipole source.
Figure 22D:
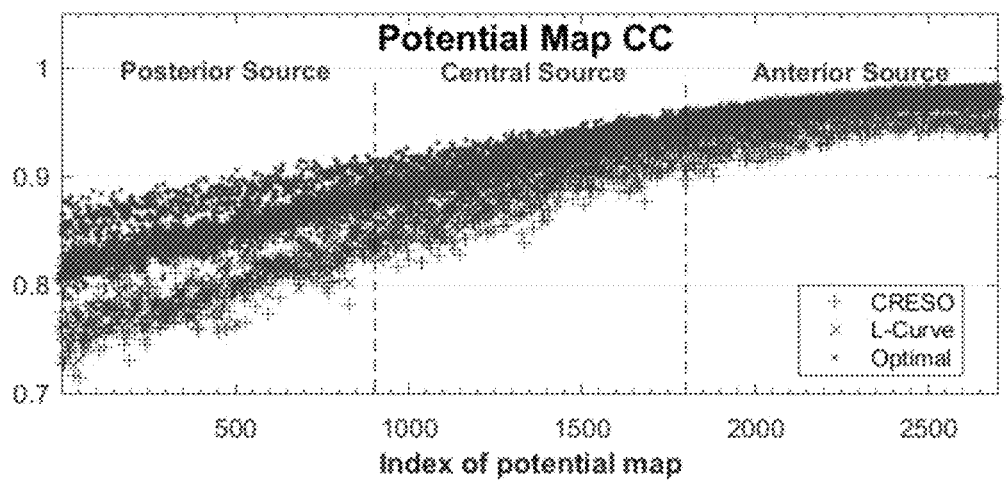
FIG. 22D is a graph showing a potential map CC; red, optimal λ, blue, mean CRESO λ, and green, L-Curve λ. Uterine sites with index of 1~300 are at the posterior, and sites with index 601~900 are at the anterior. Potential maps with index 1~900 are correlated with posterior current dipole source, and index 1801~2700 are correlated with anterior current dipole source.
Figure 22E:
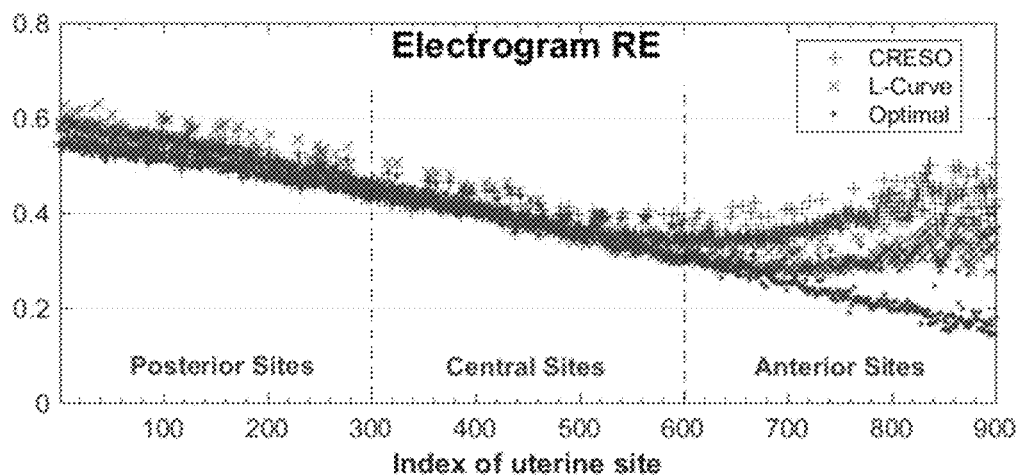
FIG. 22E is a graph showing a reconstructed electrogram EF; red, optimal λ, blue, mean CRESO λ, and green, L-Curve λ. Uterine sites with index of 1~300 are at the posterior, and sites with index 601~900 are at the anterior. Potential maps with index 1~900 are correlated with posterior current dipole source, and index 1801~2700 are correlated with anterior current dipole source.
Figure 22F:
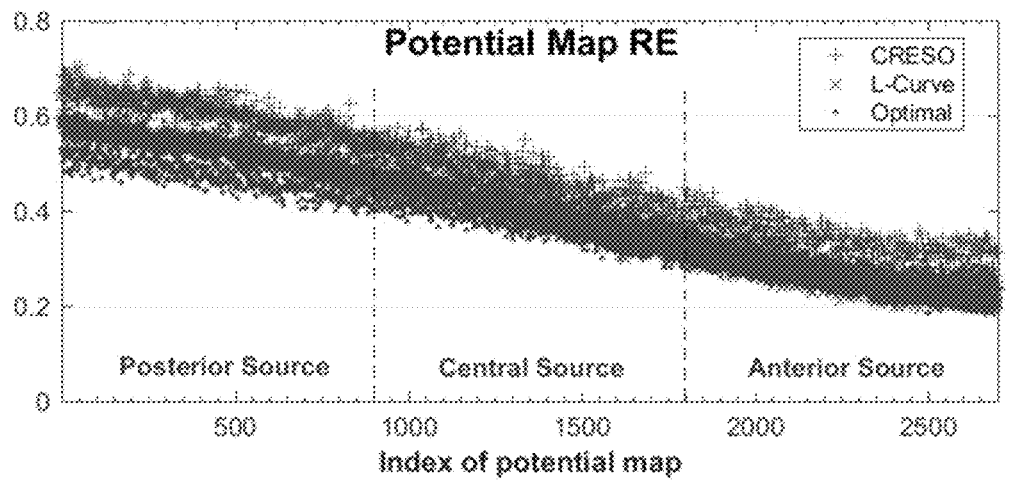
FIG. 22F is a graph showing a potential map EF; red, optimal λ, blue, mean CRESO λ, and green, L-Curve λ. Uterine sites with index of 1~300 are at the posterior, and sites with index 601~900 are at the anterior. Potential maps with index 1~900 are correlated with posterior current dipole source, and index 1801~2700 are correlated with anterior current dipole source.

We first used the CRESO, L-Curve, and optimal λ to reconstruct USPMs on a three-layer spherical geometry in the presence of white Gaussian noise with 44 microvolt average peak-to-peak magnitude (15% of the signal). FIG. 22B shows a distribution of the optimal λ and accuracy comparisons (CC and RE) among solutions derived from optimal, mean CRESO and L-Curve λ. FIG. 22A shows one representative body surface potential map. Optimal λ is large at anterior uterine sites and small at posterior uterine sites (FIG. 22B). As shown by CC and RE values (FIGS. 22C, 22D, 22E, and 22F), optimal λ produced significantly more accurate electrograms and potential maps than the other methods ($P<10^{-5}$). Especially, the superiority of SP method over the other two methods is evident for electrograms at anterior uterine sites and potential maps associated with posterior sources.

F. Comparison of Reconstruction Accuracy in Spherical Geometry

We next used the SP, mean CRESO, and L-Curve methods to reconstruct the test data and calculated the reconstruction accuracy (CC and RE) by comparing re-constructed electrograms and potential maps with simulated electrograms and potential maps, respectively. The difference of reconstruction accuracies between mean CRESO and SP (FIGS. 23A, 23B, 23C, and 23D), and between L-Curve and SP method (FIGS. 23E, 23F, 23G, and 23H) at each test data were rendered to a surface plot. In SP calculations, we used the SP derived from linear-modeled parameters r and a. The test data were sorted first by geometry eccentricity and then by noise level and assigned an index such that a larger index means larger eccentricity and higher noise level (See data file S1). The surfaces turn upwards in FIGS. 23A and 23E and turn downwards in FIGS. 23C and 23G at higher test data index, which means the SP method was superior to the mean CRESO and L-Curve methods for deriving electrogram, especially at the largest eccentricity and highest noise level. The accuracy of reconstructed potential maps using SP method are slightly more accurate than the other two methods.

G. Comparison of Reconstruction Accuracy in RPI Geometry

Figure 24A:
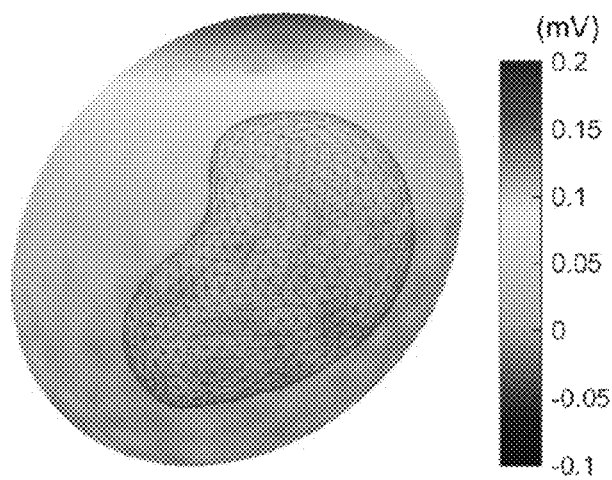
FIG. 24A is a body surface potential map with RPI geometry that includes a single current dipole; black mesh represents the uterine surface.
Figure 24B:
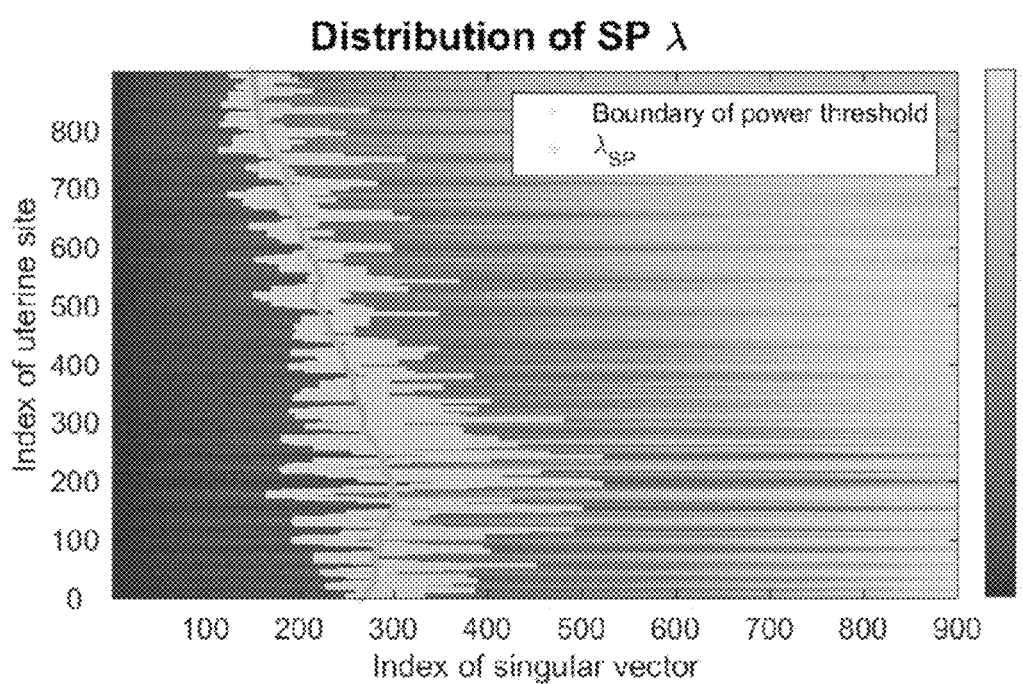
FIG. 24B is a graph showing a distribution of $\lambda_{SP}$, blue line; colormap is row cumulative of absolute X; yellow line denotes the boundary where cumulative of absolute X equals power thresholds.
Figure 24C:
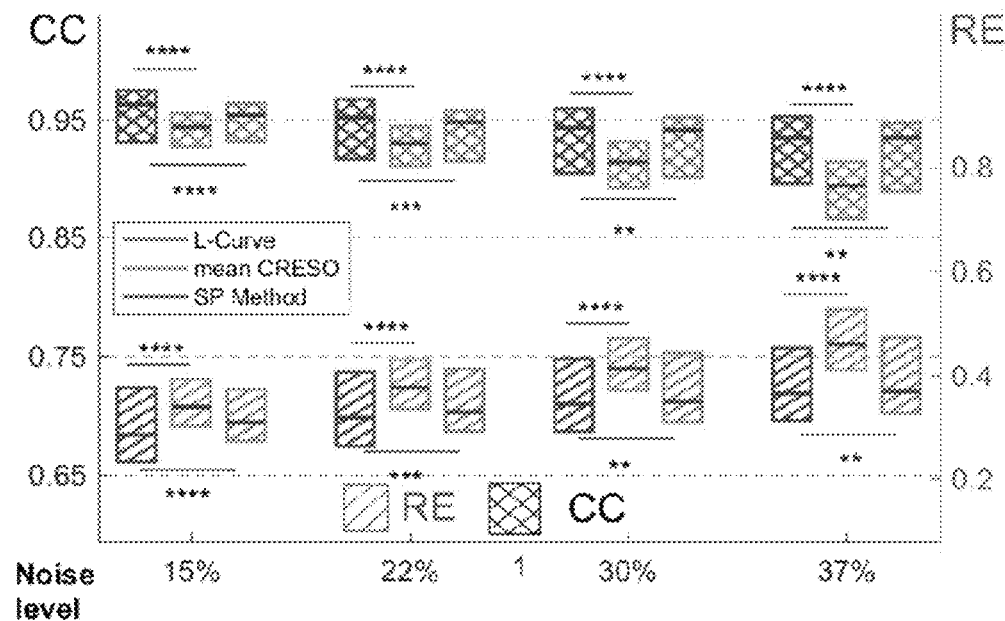
FIG. 24C is a graph showing the reconstructed electrogram accuracy of spatial dependent, mean CRESO, and L-Curve λ; cross-hatched boxes, CC values; striped boxes, RE values; blue, orange, and pink represent SP, mean CRESO, and L-Curve methods, respectively.
Figure 24D:
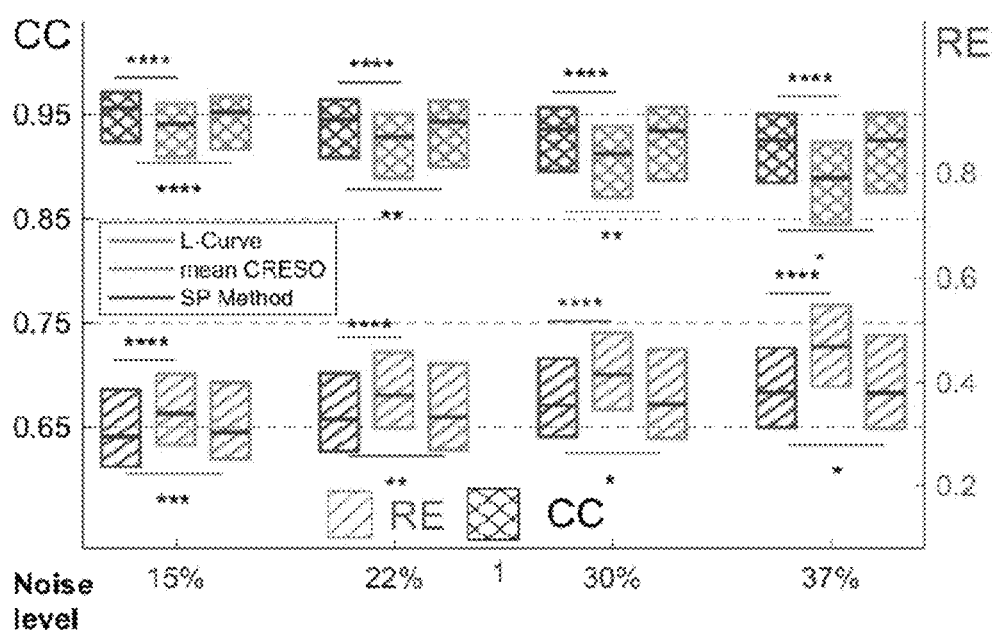
FIG. 24D is a graph showing the reconstructed potential map accuracy of spatial dependent, mean CRESO, and L-Curve λ; cross-hatched boxes, CC values; striped boxes, RE values; blue, orange, and pink represent SP, mean CRESO, and L-Curve methods, respectively.

Single current dipole: We simulated BSPMs with the three-layer RPI geometry (FIG. 19B) and single current dipoles. Four levels of white Gaussian noise were added to BSPMs, with average peak-to-peak magnitudes 15%, 22%, 30%, and 37% of the signal. FIG. 24A shows one representative BSPM after noise contamination. We calculated λSP values (FIG. 24B), used them to reconstruct uterine potentials, and compared the accuracy of the SP method to that of the mean CRESO and L-Curve methods (FIGS. 24C and 24D). Both electrograms and potential maps were reconstructed significantly more accurately with λSP than with the mean CRESO parameter, especially at higher noise levels ($P<10^{-10}$). Moreover, at 15% and 37% noise, the median electrogram CCs of SP reconstructions were 2% and 4.5%, respectively, higher than those of CRESO reconstructions, the median electrogram REs of SP reconstructions were 15.7% and 20.8%, respectively, lower than those of CRESO reconstructions, the median potential map CCs of SP reconstructions were 1.5% and 4.1% higher, respectively, than those of CRESO reconstructions, and the median potential map REs of SP reconstructions were 13% and 18.9%, respectively, lower than those of CRESO reconstructions. Electrograms generated with the SP method were significantly more accurate than those of generated with the L-curve method ($P<10^{-2}$). The accuracy of reconstructed potential maps of the SP method is significantly more higher than the L-Curve method when noise level is less than 30% ($P<10^{-2}$).

Figure 25A:
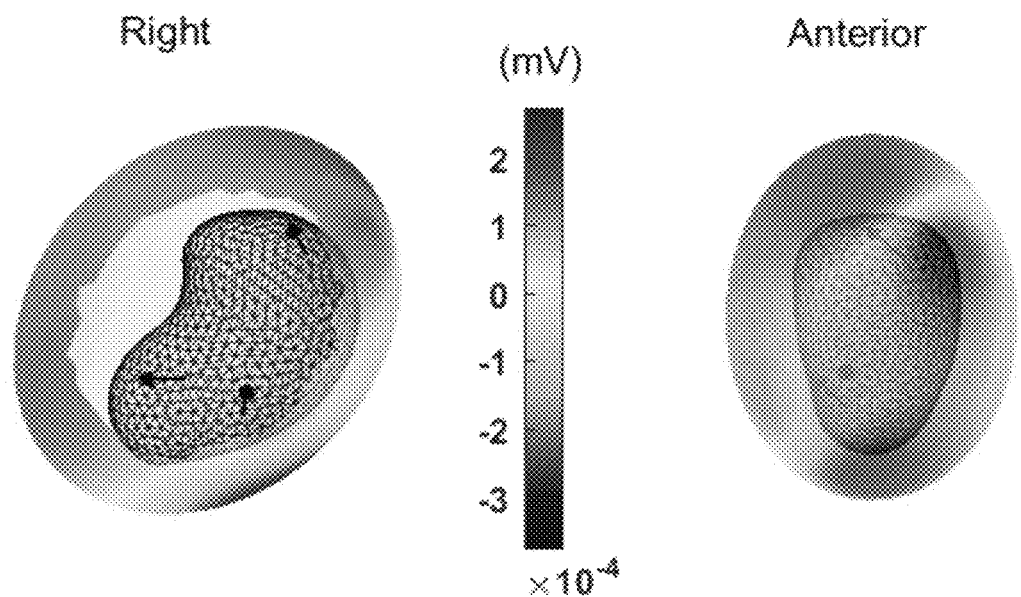
FIG. 25A is a body surface potential map with RPI geometry that includes multiple current dipoles, shown in the right and anterior views; black mesh, RPI uterine surface; black arrows, dipole locations and directions.
Figure 25B:
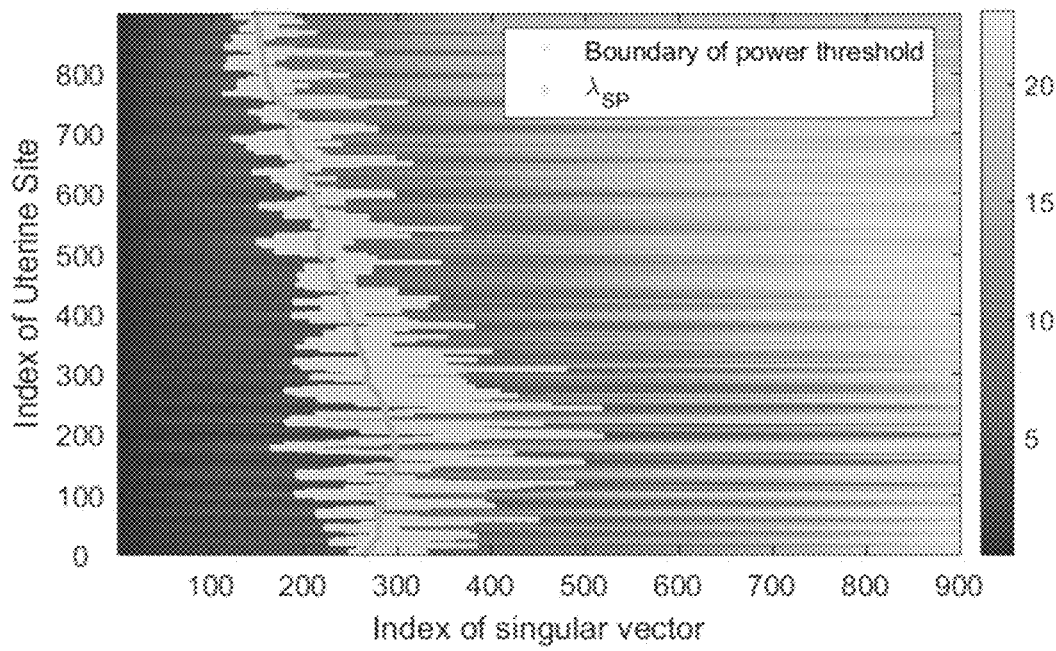
FIG. 25B is a graph showing a distribution of $\lambda_{SP}$, blue line; colormap is row cumulative of absolute X; yellow line denotes the boundary where cumulative of absolute X equals power thresholds.
Figure 25C:
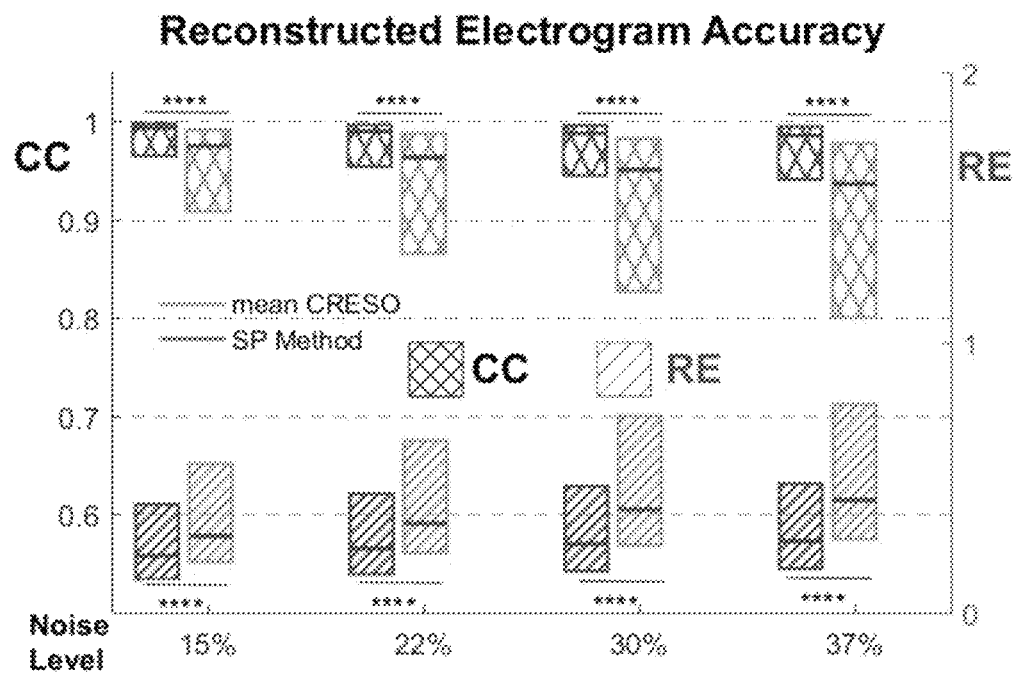
FIG. 25C is a graph showing the reconstructed electrogram accuracy of spatial dependent, mean CRESO, and L-Curve λ; cross-hatched boxes, CC values; striped boxes, RE values; blue, orange, and pink represent SP, mean CRESO, and L-Curve methods, respectively.
Figure 25D:
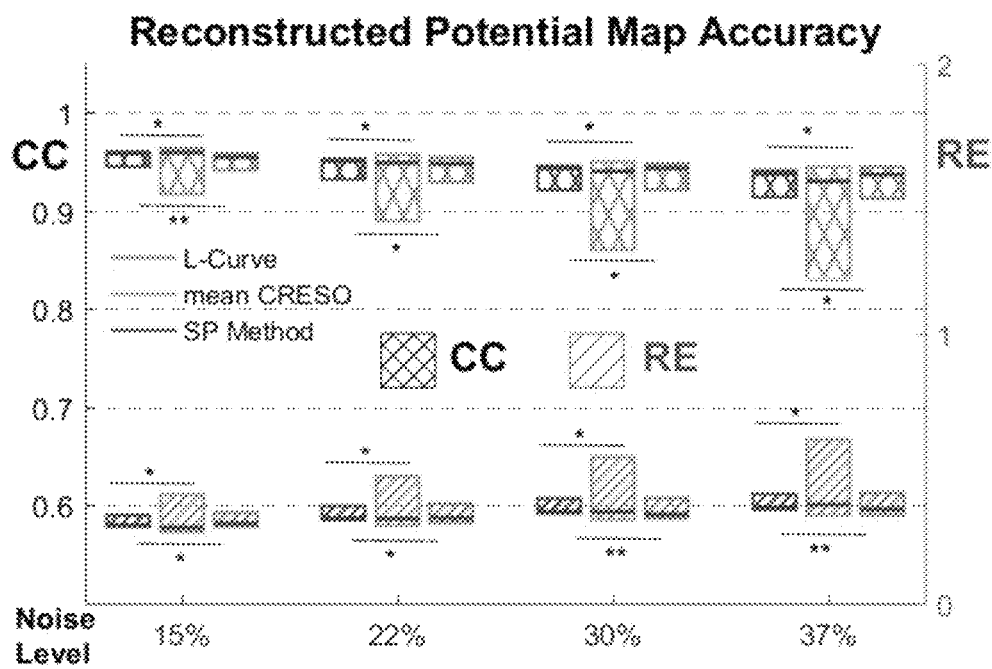
FIG. 25D is a graph showing the reconstructed potential map accuracy of spatial dependent, mean CRESO, and L-Curve λ; cross-hatched boxes, CC values; striped boxes, RE values; blue, orange, and pink represent SP, mean CRESO, and L-Curve methods, respectively.

Multiple current dipoles: Finally, we simulated BSPMs with the three-layer RPI geometry and three current dipoles (Table II). Four levels of white Gaussian noise were added to the simulated BSPMs, with average peak-to-peak magnitudes 15%, 22%, 30%, and 37% of the signal. A representative BSPM was rendered in a color map (FIG. 25A). We calculated λSP values (FIG. 25B), used them to reconstruct uterine potentials, and compared the reconstruction accuracy of the SP method to that of the mean CRESO and L-Curve methods (FIGS. 25C and 25D). The reconstruction of electrograms with the L-Curve method failed because the maximum CC was less than 0.5 and the minimum RE was larger than 2.2, even at the lowest noise level. Electrograms reconstructed with SP were significantly more accurate than those reconstructed with mean CRESO, especially at higher noise levels ($P<10^{-10}$). For example, at 15% and 37% noise, the median electrogram CCs of SP reconstructions were 1.8% and 5.3%, respectively, higher than those of CRESO reconstructions, and the median electrogram REs were 25.7% and 36.5%, respectively, lower than those of CRESO reconstructions. The median potential map CC of the SP reconstructions was similar (less than 1%) to that of the CRESO reconstructions, and the median potential RE of SP reconstructions was less than 4% higher than that of CRESO reconstructions.

Figure 25E:
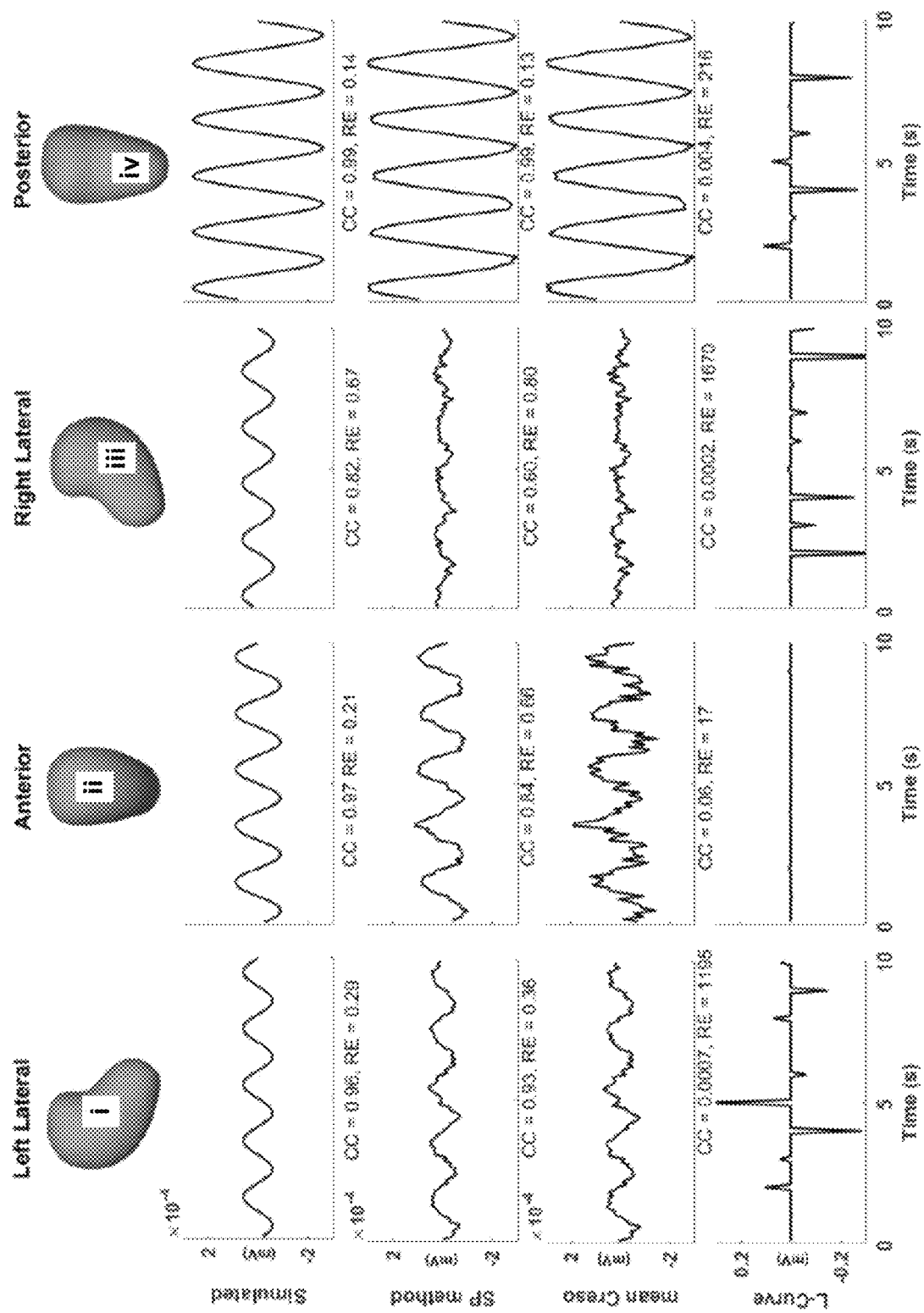
FIG. 25E is a graph comparing simulated and EMMI-reconstructed electrograms (0-10 seconds) from the indicated sites I, ii, iii, and iv of BSPMs with 15% noise; * not significant,  $P<10^{-2}$, * $P<10^{-5}$, **** $P<10^{-10}$, compared to SP method.

FIG. 25E shows simulated electrograms and electrograms reconstructed with the three regularization methods at four uterine locations. The L-Curve method failed to reconstruct accurate uterine electrograms at any of the sites (CC<0.1, RE>10). At anterior, left lateral, and right lateral sites, the SP-reconstructed electrograms were more accurate than those reconstructed with the mean CRESO method.

Discussion

In this study, we tested the SP method in both simple uterine surface potential patterns (single dipole) and more complicated potential patterns (three dipoles). In both cases, the SP method reconstructed electrograms and potential maps that were more accurate (higher CC and lower RE values) than those reconstructed with the L-curve and CRESO methods. In cardiology field, simulation models with one or two current dipoles are widely used to represent the myocardium contraction, however, different to myocardium, there is no pacemaker to synchronously activate myometrium, which would lead to a more complicated potential patterns. A complicated potential pattern was observed in a sheep study. The superiority of the SP method over the L-curve and CRESO methods was especially evident at high levels of noise. This would be important clinically, as noise in a hospital room will likely not only come from the maternal breathing and movement, etc. but also come from environmental noise and monitors. Finally, the superiority of the SP method was especially evident in more eccentric body-uterus geometries. This would be important clinically, as patient-specific body-uterus geometry is various which leads to a range of body-uterus eccentricities.

Although we developed the SP method for EMMI, it can be readily applied to improve the accuracy of other electrical imaging modalities such as ECGI. For example, Oster and Rudy showed that accurate ECG imaging of cardiac arrhythmia requires a spatial-dependent regularization parameter. Here, we used boundary element method (BEM) to discretize the Laplacian equation underlying EMMI. Our results demonstrated that the SP method can significantly improve the inversion accuracy of a BEM-derived transfer matrix. Because the optimal regularization parameters were only determined by the eccentricity of the body-uterus geometry, the normalized uterine surface to body surface distance, and the signal-to-noise ratio of the BSPM, the SP method should also be effective with other popular numerical methods such as the finite element method, and the method of fundamental solution.

Conclusions

Electromyometrial imaging (EMMI) is the first imaging modality enabling noninvasive, high-resolution mapping of uterine activation in three dimensions. Clinically, EMMI may prove useful for managing patients with preterm contractions. Here, we demonstrated that the solution of the inverse problem underlying EMMI can be significantly improved by optimizing the regularization parameter (lambda) for each uterine site using spatial-dependent (SP) method. We employed two simulation models to show that the SP method is superior to other available regularization methods in reconstructing both electrograms and potential maps. This was especially true at high noise levels and in severe eccentric body-uterus geometries. The SP method can be readily integrated into the EMMI inverse computation and significantly improve EMMI reconstruction including electrogram and potential maps. The SP method holds great promise in facilitating EMMI's successful clinical translation.

Example 4: Spatial-Dependent Regularization to Solve the Inverse Problem in Electromyometrial Imaging This example describes the development of a spatial-dependent (SP) regularization method that considers both body-uterus eccentricity and EMG noise. Electrical signals were simulated with spherical and realistic geometry models to compare the reconstruction accuracy of the SP method to those of existing CRESO and the L-Curve methods. The SP method reconstructed electrograms and potential maps more accurately than the other methods, especially in cases of high eccentricity and noise contamination.

Proper timing and force of uterine contractions, which are driven by the contraction of the uterine smooth muscle, are necessary for successful term delivery of an infant. Several methods have been developed to clinically monitor uterine contractions, such as tocodynamometers, which measure body surface contour displacements caused by uterine contractions, and intrauterine pressure catheters. However, the latter method is invasive and poses maternal and neonatal risks, and neither method can assess uterine contractility at high spatial and temporal resolution. In a non-clinical method, electromyography (EMG), 4 to 64 electrodes are placed on a small region (around 4 cm by 4 cm) of the body surface and used to monitor myometrial electrical activity EMG signals are the spatial integral of action potentials from all of the myometrial cells. Although EMG-measured electrical signals can distinguish between term and preterm labor. EMG cannot provide sufficient spatial resolution and coverage to reflect the detailed uterine electrophysiological patterns during contractions. Thus, we cannot answer basic questions such as where uterine contractions initiate, whether they always propagate in the same manner and speed, how contractions in different uterine regions correlate with one another, and what differentiates productive (leading to labor and delivery) contractions from non-productive preterm contractions.

To address the limited spatial resolution and coverage of EMG, we recently developed electromyometrial imaging (EMMI). In EMMI, a subject wearing magnetic resonance imaging (MRI) markers first undergoes MRI to derive a body-uterus geometry (FIG. 18). Then, when the subject is in labor, up to 256 electrodes are placed on the body surface in the same positions as the MRI markers and used to measure EMG and generate body surface potential maps. Next, EMMI software solves an inverse problem (the Cauchy problem, see section 2.1 for details) to combine the subject-specific body-uterus geometry with the measured body surface EMG signals and thus reconstruct uterine surface electrical potentials. EMMI is based on a similar method used to monitor heart activities, electrocardiographic imaging (ECGI).

Because the inverse reconstruction procedure underlying both EMMI and ECGI is ill-posed, a small amount of noise in the measured body surface electrical signals could cause large errors in the reconstructed electrical signals on the uterine or heart surface. To stabilize the in-verse computation underlying ECGI, several regularization methods have been proposed. The most widely used is the zero-order Tikhonov (ZOT) regularization method, with composite residual and smoothing operator (CRESO) determining a global regularization parameter, $\lambda$, which is applied to all sites on the heart. This method is also used in EMMI. However, because the same $\lambda$ is applied to all heart/uterine sites, under-regularization could occur for some sites, and over-regularization could occur for other sites, impairing reconstruction accuracy. For example, Oster et al. used a spherical geometry model to show that, in ECGI, optimal $\lambda$ will differ depending on the distance between a site on the heart surface and the nearest body surface site. This under- and over-regularization is likely a more severe problem for EMMI than for ECGI because the uterus is farther from the center of the body along the anterior-posterior axis than is the heart.

One approach to solving this problem is to use $\lambda$ optimized for each uterine site. However, no methods have been developed to compute site-dependent $\lambda$. Here, we developed and tested a spatial-dependent (SP) method to compute site-specific $\lambda_{SP}$ for EMMI, though this method could also be used for ECGI. We first developed the SP method by using COMSOL Multiphysics to build a detailed numerical simulation of the body-uterus geometry and electrical activities. Next, we compared the reconstruction accuracy of the SP, mean CRESO, and L-Curve regularization methods on both spherical and realistic body-uterus geometries. We show that the SP method produces more accurate EMMI reconstructions than the CRESO or L-Curve methods.

Materials and Methods

EMMI reconstructs uterine surface potential maps (US-PMs) during uterine contractions by combining the body surface potential maps (BSPMs) and subject-specific body-uterus geometry segmented from MRI images. The methods and equations used to formulate and solve the inverse problem used to reconstruction uterine surface potential distributions based on surface electrode readings are described in Example 3 above.

The overall process of determining the spatially-dependent regularization ($\Delta_{sp}$ as defined in Equation 12 of Example 3) may be represented by the relation:

$$\lambda_{sp}=f(G,\phi_B)$$

where G represents the body-uterus geometry, which is denoted by XYZ coordinates and the triangular connectivity of each coordinate; $\phi_B$ represents the body surface potential map.

The function $f$ represents the computation process as described in FIG. 19. After we acquired the body-uterus geometry and body surface potentials, there are three steps to generate $\lambda_{SP}$. Step 1 is to calculate the transfer matrix A equation (4) and its singular value decompositions (U, X, Σ, equation (6)) from body-uterus geometry G. Step 2 is to calculate eccentricity and signal-to-noise ratio required for $\lambda_{SP}$ calculation. l represents the distances from uterine sites to their nearest body surface sites. $l_{norm}$ represents the normalized vector, and $\bar{l}$ represents the average of l vector. e represents the eccentricity of body-uterus geometry, which is defined by the standard deviation of l vector. The signal-to-noise-ratio (SNR) for each $\phi_B$ is defined by the ratio between the mean absolute value of the first 10% and the last 30% of d, based on the discrete picard condition for the inverse problem. Step 3 is to calculate $\lambda_{SP}$ by using e, SNR, $l_{norm}$, X, and Σ derived from the first two steps. The level threshold function p(a) is a function of variable a and the normalized nearest distance vector $l_{norm}$. For each a, the $j_k(a)$ is defined as the maximum index of singular basis satisfying $$\sum_{v=1}^{j} X_{kv} \geq p_k$$

in equation (b). Then in equation (c), g(a) is computed by smoothing j using a moving average filter with window size equal to 5% of the uterine sites. g(a) is the optimized index of singular vector basis for $\lambda_{SP}$. The under-curve ratio r(a) is defined as the ratio between the area under the curve of g(a) over the total area (=NZ) of cumulative X. r is determined by e and SNR with the estimation model r=q[e, SNR, 1]. The optimized a can be computed by minimizing the difference between r(a) and r, and then the optimized p, g are derived. Finally, the $\lambda_{SP}$ for each uterine site is computed. After $\lambda_{SP}$ is derived, the inverse solution can be calculated according to equation 11 from Example 3 above. The derivation of the level threshold function p(a) and estimation model r are described below.

Definition of Level Threshold Function p(a)

Figure 30A:
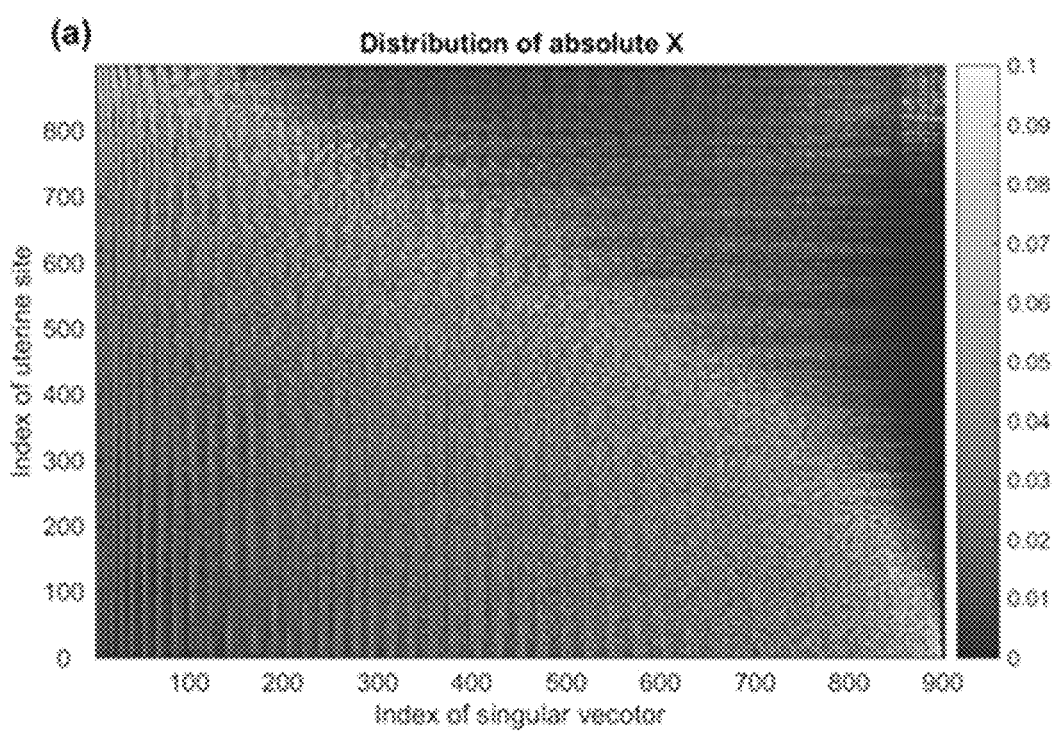
FIG. 30A is a graph showing a distribution of absolute values of X. Columns of X are the singular vectors, and rows correlate with uterine sites. Yellow color and blue color represent large and small values, respectively.
Figure 30B:
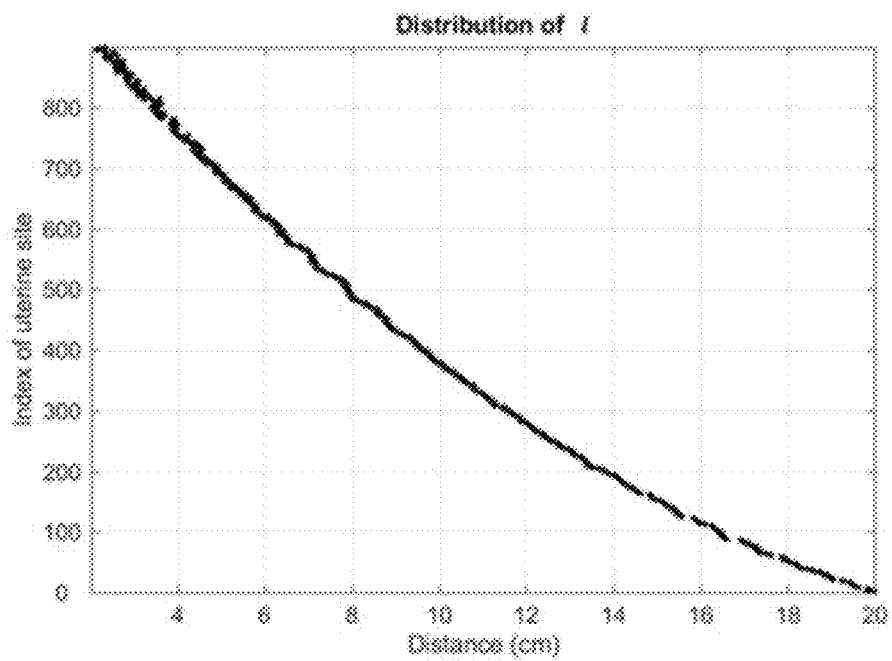
FIG. 30B is a graph showing a distribution of distances from uterine sites to nearest body surface sites (l) in the three-layer spherical geometry of FIG. 29A.

Based on the ZOT regularization solution of the inverse problem, the regularization parameter in equation (9) of Example 3 above controls the contribution of $i_{th}$ singular basis vector X.,i to the solution $\phi_U$. With the regularization parameter λ, at very small σ the weight would decay to around 0 otherwise would blow up and lead to an unreasonable solution. The traditional regularization method implements a global λ for all the uterine sites. However, the distribution of X values is different at each row, which is associated with potentials at each uterine site. FIG. 30A shows the distribution of absolute X for a spherical geometry (FIG. 26A). We noted that the larger absolute X values of anterior sites (row index 600~900) are distributed within lower indexed singular basis vectors, and larger absolute X values of posterior sites (row index 1~300) are located within higher indexed singular vectors. Therefore, the weight of X would be related to the uterine site locations. To represent the spatial differences of each uterine site, we correlated the regularization parameters with that the distribution of the nearest distance from uterine sites to body surface (vector l, FIG. 30B) and proved that the optimal cumulative |X| is linear to $l_{norm}$, shown as equation (s1).

$$p = a \times (b - l_{norm}) = [p_1, p_2, \ldots, p_k, \ldots, p_N]^T \quad (s1)$$

where a and b are variables, $l_{norm}$ represents l normalized to the length of one, $p_k$ denotes the level threshold value of the $k_{th}$ the uterine site, and N is the number of uterine sites.

Derivation of optimal λ and optima p for each uterine site. We used the ZOT method to consider all singular values ($\sigma_i$, i=1, 2, . . . , Z) of transfer matrix A as candidate regularization parameters to reconstruct a series of uterine potentials from BSPMs. The optimal uterine surface site-specific $\lambda_k$ was defined as the singular value $\sigma_i(k)$ that maximized the CC value between the reconstructed and simulated electrograms at the $k_{th}$ uterine site, where i(k) denotes the index of the correlated singular value $\sigma_i(k)$. Then the optimal energy level at each uterine site is defined as equation (s2).

$$p_k = \sum_{i=1}^{i(k)} X_{k,i} \quad (s2)$$

where $p_k$ denotes the power threshold value of the $k_{th}$ uterine site and N is the number of uterine sites.

Proof of the linear relation between p and l. We simulated body surface potentials with 100 levels of white Gaussian noise, with average peak-to-peak magnitude from 8% to 32% of the simulated body surface potentials and the spherical geometry (FIG. 19A). We calculated the optimal p for each set of BSPMs and then computed the CCs between the optimal p and the l. We found that optimal p was negatively linearly related with l with mean CC value lower than −0.8.

Figure 30C:
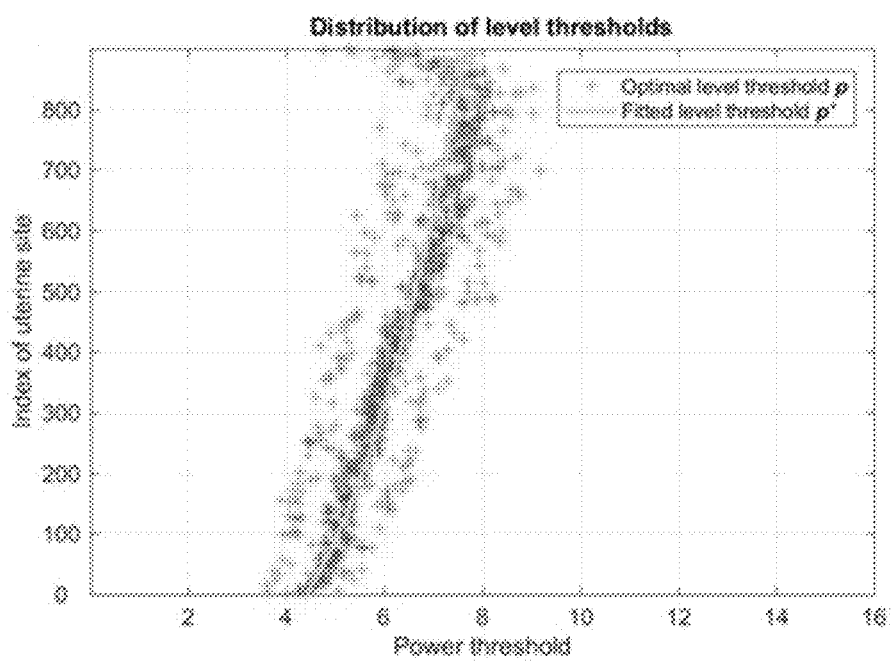
FIG. 30C is a graph showing a distribution of optimal power threshold values and least-square fitted threshold values.
Figure 30D:
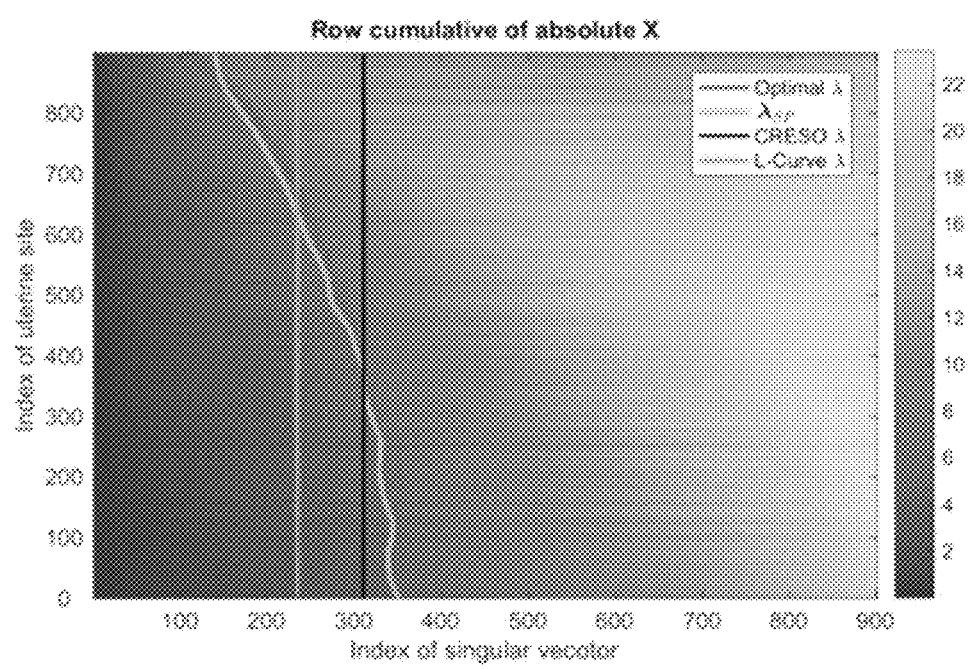
FIG. 30D is a graph showing a row cumulative of absolute X, optimal λ (magenta), $\lambda_{SP}$ (blue), CRESO A (black) and L-Curve λ (green). BSPM used for this power threshold function was generated by adding noise with average peak-to-peak magnitude 15% of the signal.

Then we used equation (s1) to fit the optimal p at each noise level by minimizing the squared residual between optimal p and fitted p. The optimal parameters of the 100 sets of BSPMS are a=3.46±0.78, b=2.2±0.14, and fitting accuracy (equation s3) $R^2$=67%±6.5%. Based on the standard deviation of a and b, b changes slightly. Then we set b as its mean value (2.2) and used the same least square method to find optimal a. The fitting accuracy $R^2$ of b as a variable and as a constant were compared, and the difference of $R^2$ is −0.4%±0.37%, which only slightly decreases when b was set as the mean value. Therefore, b was set as a constant with the value of mean b=2.2 and a is set as a variable, where a is a variable, which is related to the body-uterus geometry and measured signal quality.

$$R^2 = 1 - \frac{\sum_k (p'_k - p_k)^2}{\sum_k (p_k - \bar{p})^2} \quad (s3)$$

where k=1, 2, . . . , N denotes the index of the uterine site, p and p' represents optimal and fitted level thresholds, and $\bar{p}$ represents the mean value of optimal p values. The $R^2$=1 means no fitting error. FIG. 30C shows distribution of optimal p and fitted p of the BSPMs contaminated by noise with average peak-to-peak magnitudes equal to 15% of the signal ($R^2=72\%$, a=3.67). The $\lambda_{SP}$ of these BSPMs was computed based on the flowchart in FIG. 2. FIG. 3d shows the cumulative absolute X values along each row, optimal $\lambda$, $\lambda_{SP}$, CRESO $\lambda$ and L-Curve $\lambda$ in the index of singular basis vector.

Derivation of Estimation Model of r

Define e and SNR. We developed a linear regression model to find a for a general geometry and signal. Because pregnant women differ in size and body mass index, the eccentricity of the body-uterus geometry differs for each woman. We defined e, the eccentricity of body-uterus geometry (equation s4 below). Based on the discrete picard condition for the inverse problem, we used the decomposed BSPM (d defined in equation (8) of Example 3 above) to calculate the define SNR. d is a list of decompositions $d_i$ (different colored lines in FIG. 21A). SNR is defined as the ratio between the mean power of the last 30% of d and the mean power of the first 10% of d. The true SNRs of 100 different levels of BSPMs were calculated with equation (s5 below). The correlation between the defined SNR and true SNR for each BSPMs was calculated and shown in FIG. 21B, which are 98% linearly correlated.

$$e = \sqrt{\frac{\sum_{k=1}^{N}(l_k - \bar{l})^2}{N-1}} \quad (s4)$$

$$SNR = 10\log_{10}\frac{P_{signal}}{P_{noise}} \quad (s5)$$

where $l_k$ represents the distance from $k_{th}$ uterine sites to its nearest body surface sites. P represents the power of the signal or the noise.

Simulation of BSPMs in different geometries and noise contamination. Here, 20 spherical geometries were developed with displacement $dis(O_U, O_B)$ from 0 cm to 9 cm, and the other simulation settings in Table 1 and Table 2 of Example 3 above were unchanged. The eccentricity of the geometries varies from 0 to 48 mm. We then used COMSOL Multiphysics software and a single current dipole to derive paired body and uterine surface potentials under these 20 geometry settings. We also added twenty different levels of white Gaussian noise, with average peak-to-peak magnitude from 25 microvolts to 100 microvolts (8% to 42% of signal) to the body surface potentials. Thus, we generated a total of 400 data sets, each with a pair of body and uterine surface potentials.

Definition of linear model r. We acquired the optimal a ($a_{opt}$) for each data set by using the least-square method to minimize the mean-square error of CC values between the reconstructed and true electrograms and potential maps. We calculated the CCs between $a_{opt}$ and e, and between $a_{opt}$ and SNR, respectively. We found that $a_{opt}$ is linearly related with SNR (CC 0.94), but is not linearly related with e (CC 0.12). To find a linear model, we defined a new parameter r, the ratio between the area under the curve of $\lambda_{SP}$ over the total cumulative X area, which is uniquely determined as a nonlinear function of a (see flowchart in FIG. 26). We calculated $r_{opt}$ and computed the CC value between $r_{opt}$ and e, and between $r_{opt}$ and SNR, respectively, which are 0.7 and 0.9. Then we used 90% of the data set with pairs of r-e-SNR as the linear regression training set and generated the linear regression model as equation (s6) to represent r.

$$r = q[,SNR,1] \quad (s6)$$

in which, r represents the area ratio, e represents eccentricity, and $q=[0.0015, 0.0113, -0.0254]^T$, with $R^2=0.96$.

Validation of the linear model of r. The linear model was applied to the other 10% of the data set, and area ratio r and coefficient a were calculated for each data set. We evaluated the errors of parameters a and r by comparing with $a_{opt}$ and $r_{opt}$ with linear-modeled r and a, and compared the reconstruction accuracy in terms of CC and RE with the results reconstructed with the $a_{opt}$ and $r_{opt}$. The errors of the test data set are listed in FIGS. 21C and 21D. There was only a minor error in terms of parameters a and r and in the reconstructed electrograms and potential maps.

Bio-Electricity Simulation

Using the corresponding equations and methods described in Example 3 above, the CRESO, L-Curve, and SP methods were used to reconstruct USPMs from the simulated BSPMs with spherical and RPI geometries. CC and RE, also defined above, were used to compare the reconstruction accuracies of the three methods. Statistical significance of differences (P-value) was determined with one-tailed Wilcoxon rank-sum tests in R studio.

Results

Spatial Dependence of Optimal Regularization Parameter

Figure 27A:
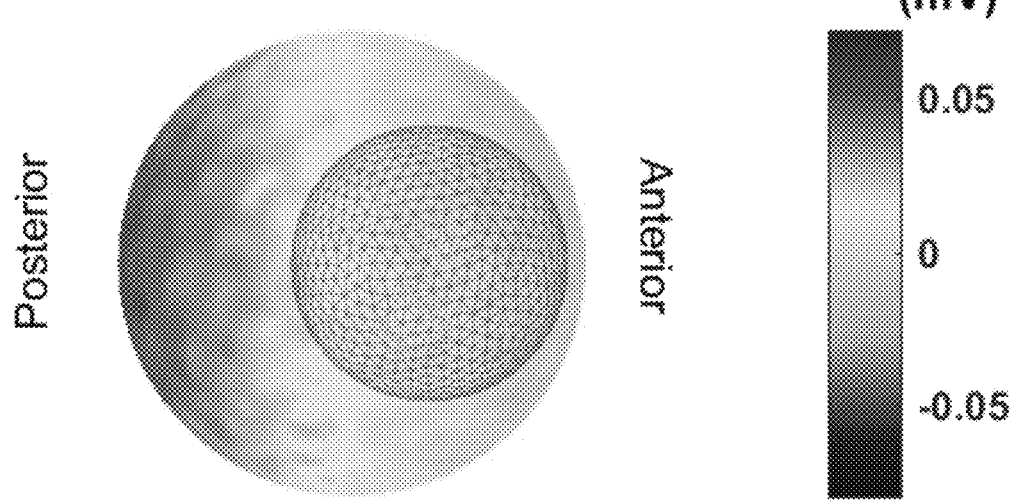
FIG. 27A is a representative right lateral view of a body surface potential map, where warm color indicates positive potential and cool color indicates negative potential; black mesh inside the color map is the uterine surface geometry.
Figure 27B:
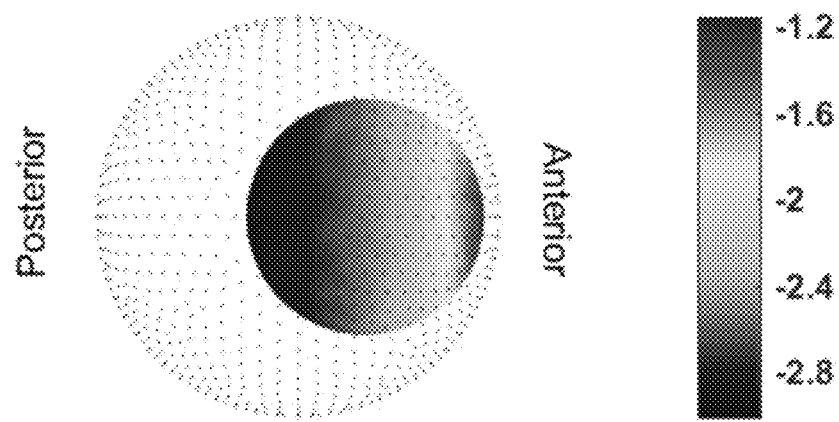
FIG. 27B is a right lateral view of a distribution map of the optimal site-specific A; blue dots are discrete points on body surface.
Figure 27C:
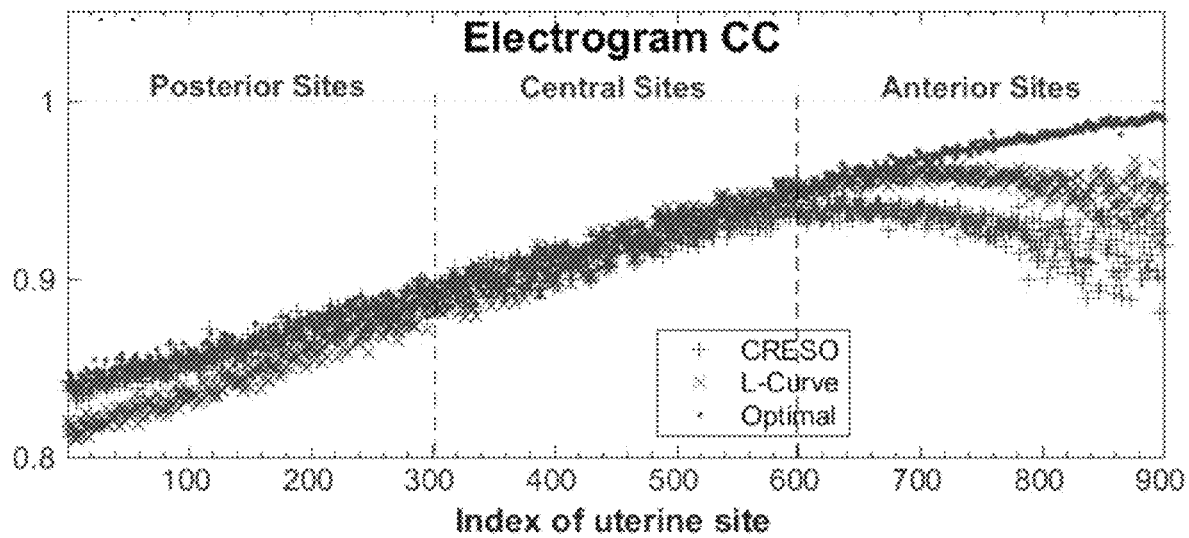
FIG. 27C is a graph showing reconstructed electrogram correlation coefficient (CC); red dot indicates optimal λ, blue+indicates mean CRESO λ, and green × indicates L-Curve λ. Uterine sites with index of 1~300 are located at the posterior, and sites with index of 601~900 are located at the anterior. Potential maps with index of 1~900 are correlated with posterior current dipole source, and index 1801~2700 are correlated with anterior current dipole source.
Figure 27D:
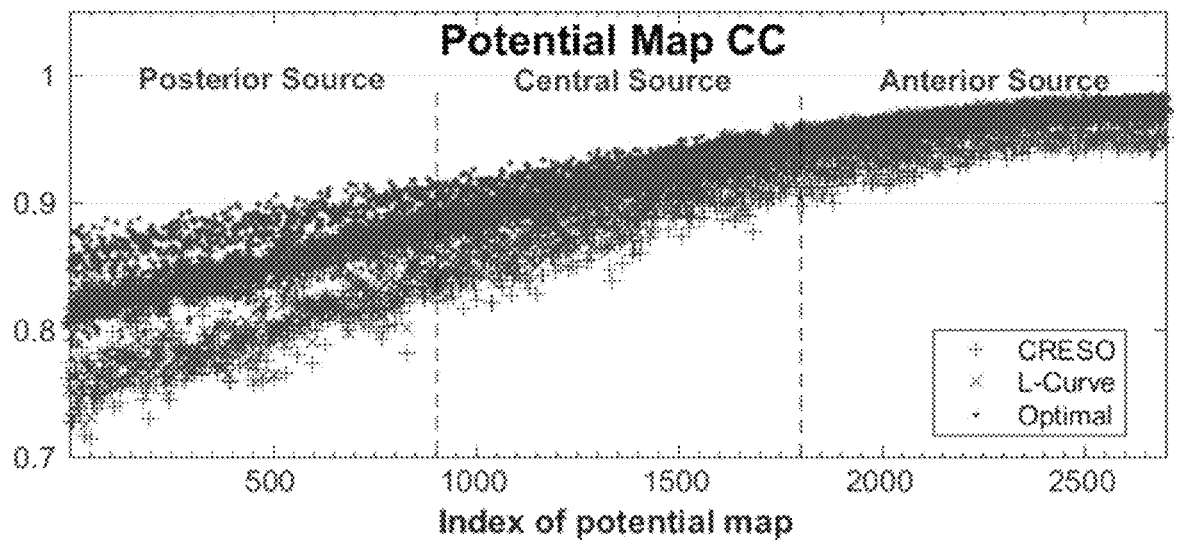
FIG. 27D is a graph showing reconstructed potential map electrogram correlation coefficient (CC); red dot indicates optimal λ, blue + indicates mean CRESO λ, and green × indicates L-Curve λ. Uterine sites with index of 1~300 are located at the posterior, and sites with index of 601~900 are located at the anterior. Potential maps with index of 1~900 are correlated with posterior current dipole source, and index 1801~2700 are correlated with anterior current dipole source.
Figure 27E:
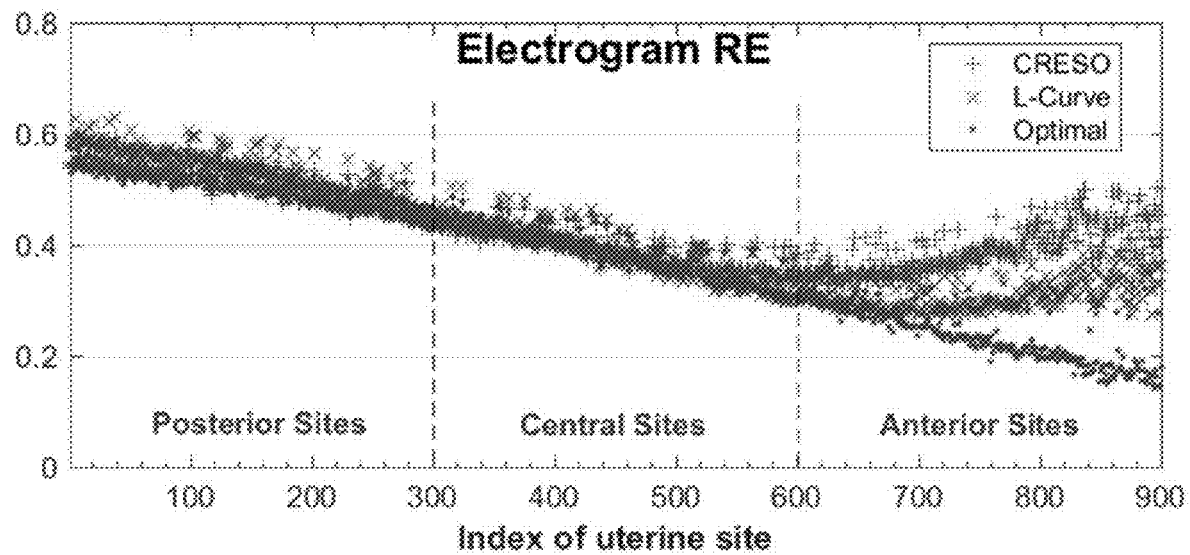
FIG. 27E is a graph showing a reconstructed electrogram relative error (RE); red dot indicates optimal λ, blue+ indicates mean CRESO λ, and green× indicates L-Curve λ. Uterine sites with index of 1~300 are located at the posterior, and sites with index of 601~900 are located at the anterior. Potential maps with index of 1~900 are correlated with posterior current dipole source, and index 1801~2700 are correlated with anterior current dipole source.
Figure 27F:
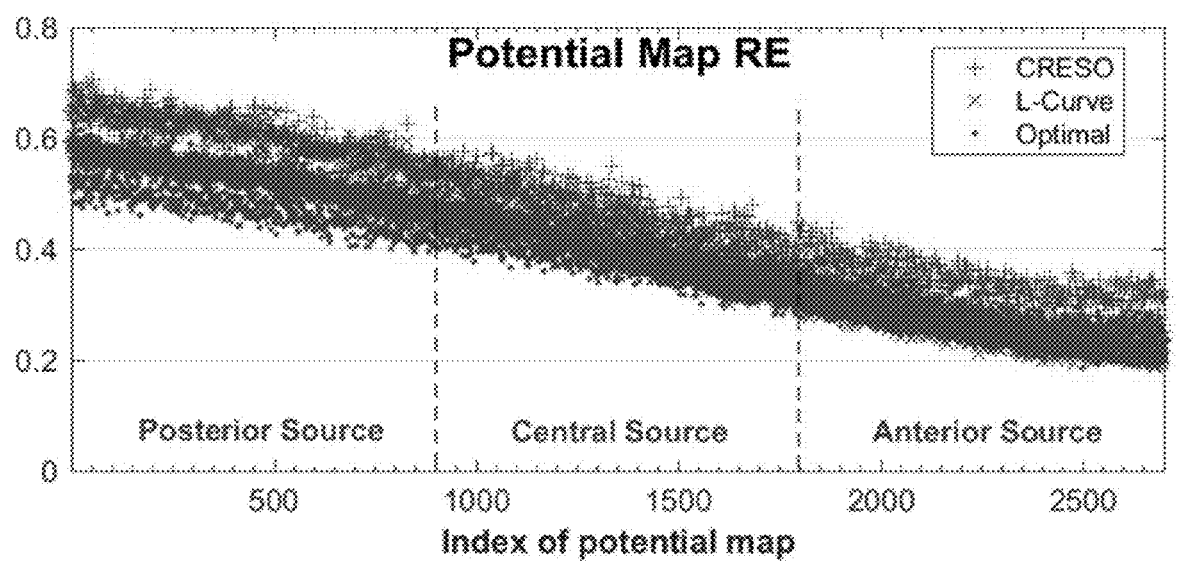
FIG. 27F is a graph showing reconstructed potential map relative error (RE); red dot indicates optimal λ, blue+ indicates mean CRESO λ, and green× indicates L-Curve λ. Uterine sites with index of 1~300 are located at the posterior, and sites with index of 601~900 are located at the anterior. Potential maps with index of 1~900 are correlated with posterior current dipole source, and index 1801~2700 are correlated with anterior current dipole source.

To confirm that the optimal regularization parameter is spatially dependent, we used BSPM-USPM pairs simulated from a three-layer spherical geometry and a single current dipole. The BSPMs were contaminated with white Gaussian noise of 44 microvolts average peak-to-peak magnitude (15% of the signal). FIG. 27A shows one representative BSPM, represented as a heat map in which warm colors denote positive potentials and cool colors denote negative potentials. We then used the CRESO and L-Curve methods to reconstruct USPMs from the noise-contaminated BSPMs. Optimal λ values were large at anterior uterine sites and small at posterior uterine sites (FIG. 27B). FIGS. 27C-27F show the electrogram CC and RE of each uterine electrogram (sample size=900), and the potential map CC and RE of each USPM (sample size=2700) reconstructed with the three regularization parameters. The morphology accuracy (CC) of optimally reconstructed uterine electrograms was higher, and the magnitude error (RE) of optimally reconstructed electrograms was lower, than the other two methods. This was especially true for the electrograms at the anterior uterine surface (uterine sites with index>600). To quantitively evaluate the superiority of the optimal λ, a one-tail Wilcoxon rank-sum test was conducted with the null hypothesis that the electrogram accuracy (CC or RE) calculated with the CRESO or L-Curve methods were equal to that calculated with optimal λ. The null hypothesis was rejected ($P<10^{-5}$) for all four comparisons (electrogram CC, optimal vs. CRESO; electrogram RE, optimal vs. CRESO; electrogram CC, optimal vs. L-Curve; electrogram RE, optimal vs. L-Curve). The reconstructed potentials maps were also more accurate with optimal λ than with the CRESO or L-Curve methods, especially the potential maps associated with posterior sources (potential maps with index<900) (FIGS. 27D and 27F). As with the electrograms, one-tail Wilcoxon rank-sum tests confirmed that the CC and RE values of potential maps were all significantly different ($P<10^{-5}$) between optimal λ and the CRESO and L-Curve methods.

Figure 26:
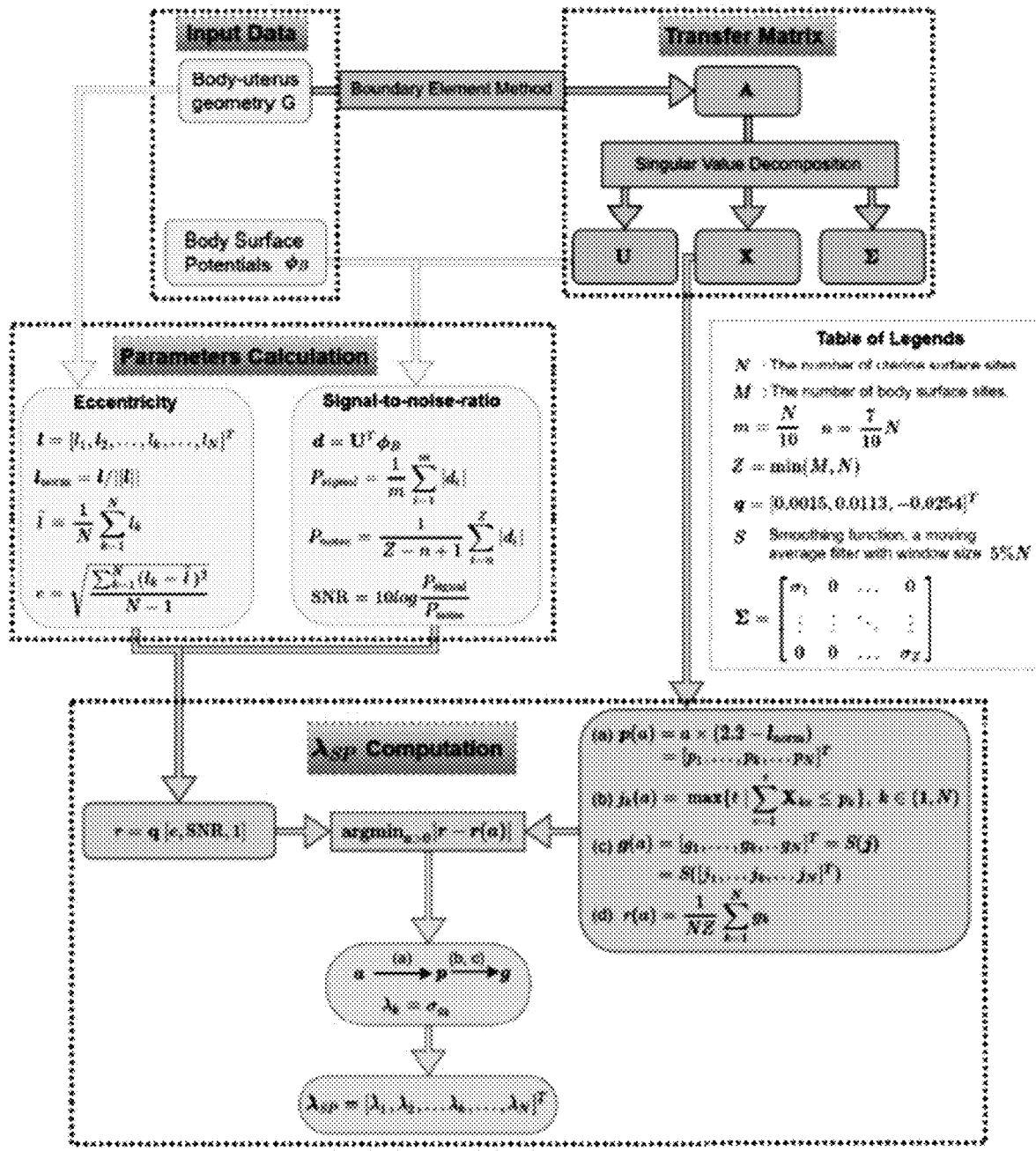
FIG. 26 is a flowchart showing a method of deriving Asp.

Comparison of Reconstruction Accuracies in Multiple Spherical Geometries and Various Noise Contaminations We calculated $\lambda_{SP}$ values according to the procedures shown in FIG. 26 and evaluated the performance of the SP, mean CRESO, and L-Curve methods on reconstructing electrograms and potential maps with simulated BSPMs from spherical geometries. Forty eccentricity (0.29 mm to 48.73 mm) and noise contamination settings (SNR 21 dB to 9 dB) were considered.

Figure 23A:
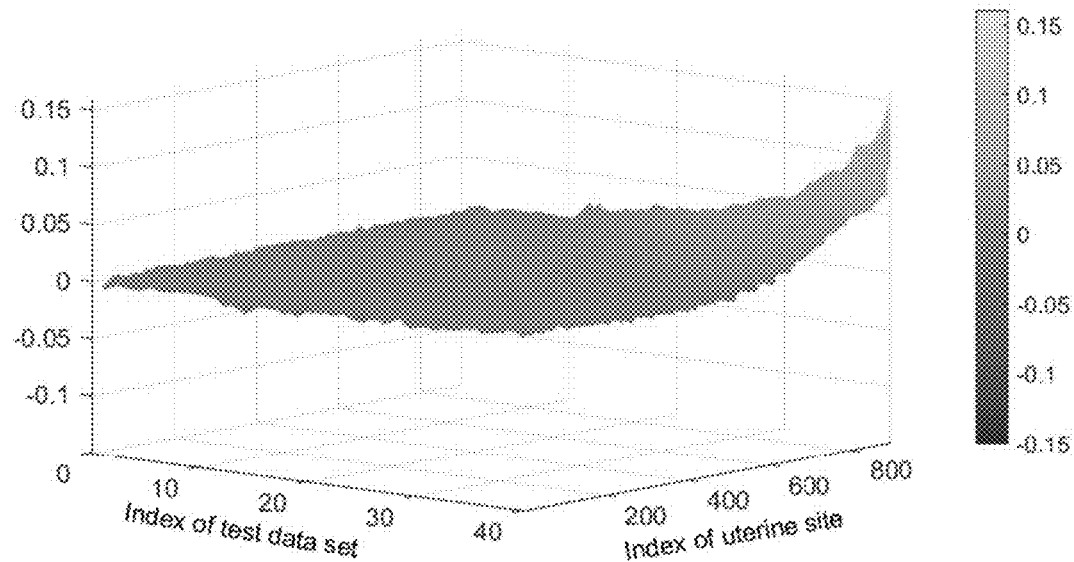
FIG. 23A is a graph showing CC values of electrograms generated by the mean CRESO method subtracted from the CC values of electrograms generated by the SP method; warm colors represent positive differences and cold colors represent negative differences; X-axis, index of test data set; Y-axis, index of the uterine site or potential map; Z-axis, the difference in values.
Figure 23B:
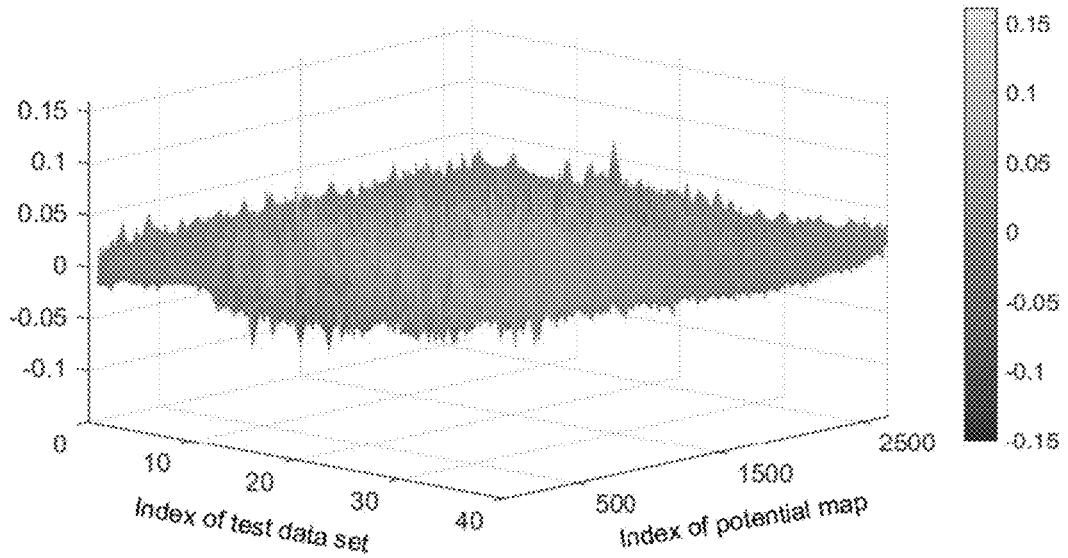
FIG. 23B is a graph showing CC values of potential maps generated by the mean CRESO method subtracted from the CC values of potential maps generated by the SP method; warm colors represent positive differences and cold colors represent negative differences; X-axis, index of test data set; Y-axis, index of the uterine site or potential map; Z-axis, the difference in values.
Figure 23C:
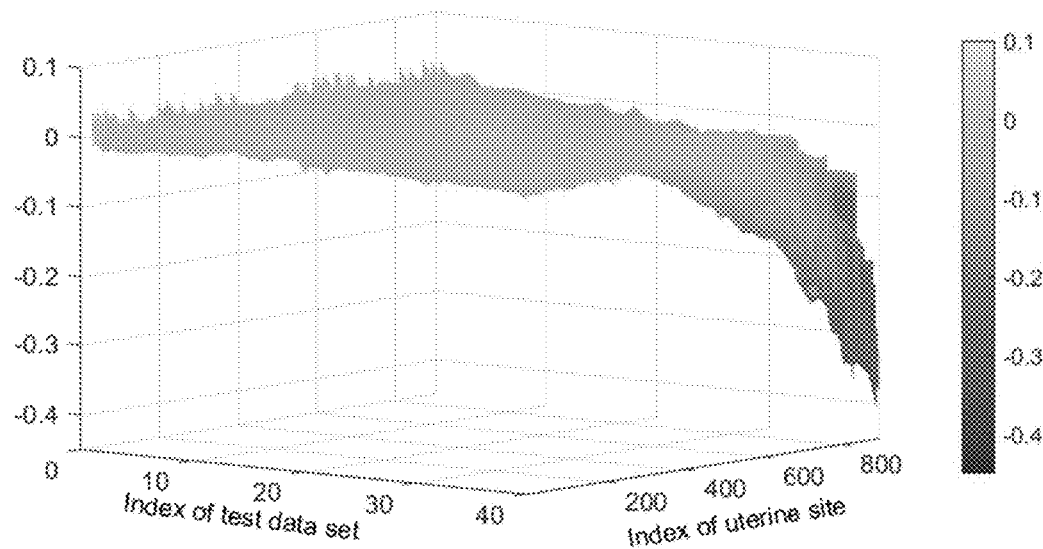
FIG. 23C is a graph showing RE values of electrograms generated by the mean CRESO method subtracted from the RE values of electrograms generated by the SP method; warm colors represent positive differences and cold colors represent negative differences; X-axis, index of test data set; Y-axis, index of the uterine site or potential map; Z-axis, the difference in values.
Figure 23D:
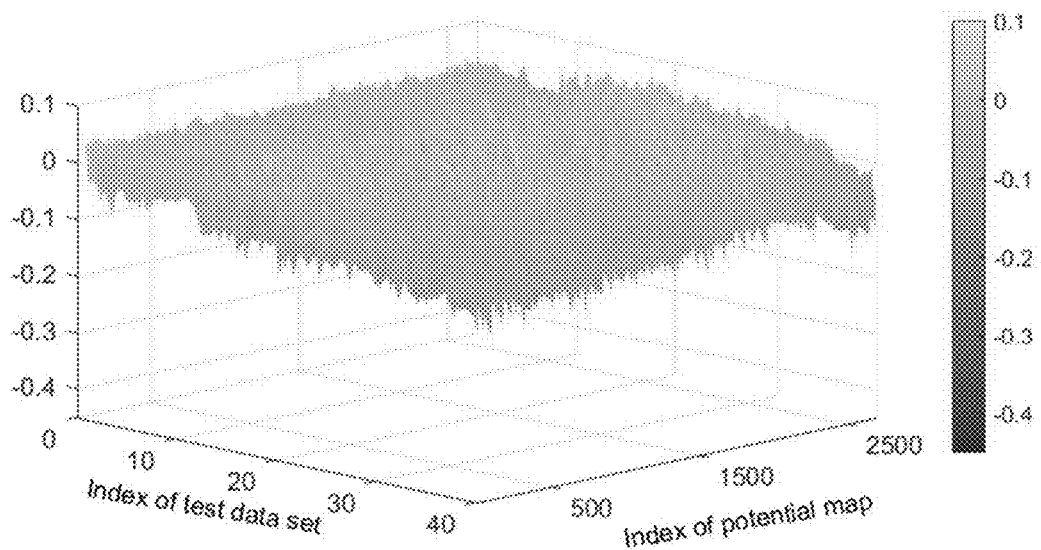
FIG. 23D is a graph showing RE values of potential maps generated by the mean CRESO method subtracted from the RE values of potential maps generated by the SP method; warm colors represent positive differences and cold colors represent negative differences; X-axis, index of test data set; Y-axis, index of the uterine site or potential map; Z-axis, the difference in values
Figure 23E:
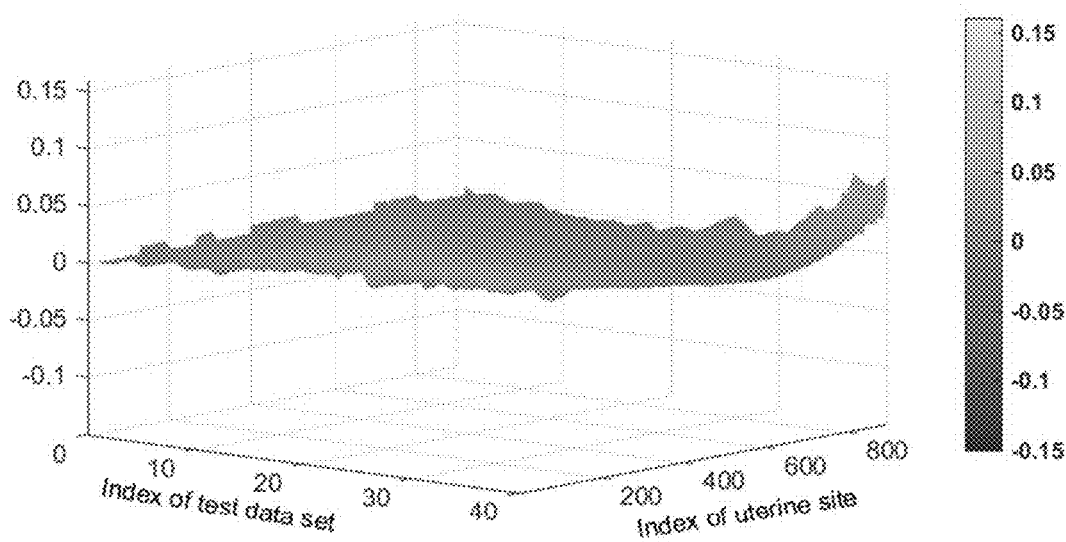
FIG. 23E is a graph showing CC values of electrograms generated by the L-curve method subtracted from the CC values of electrograms generated by the SP method; warm colors represent positive differences and cold colors represent negative differences; X-axis, index of test data set; Y-axis, index of the uterine site or potential map; Z-axis, the difference in values.
Figure 23F:
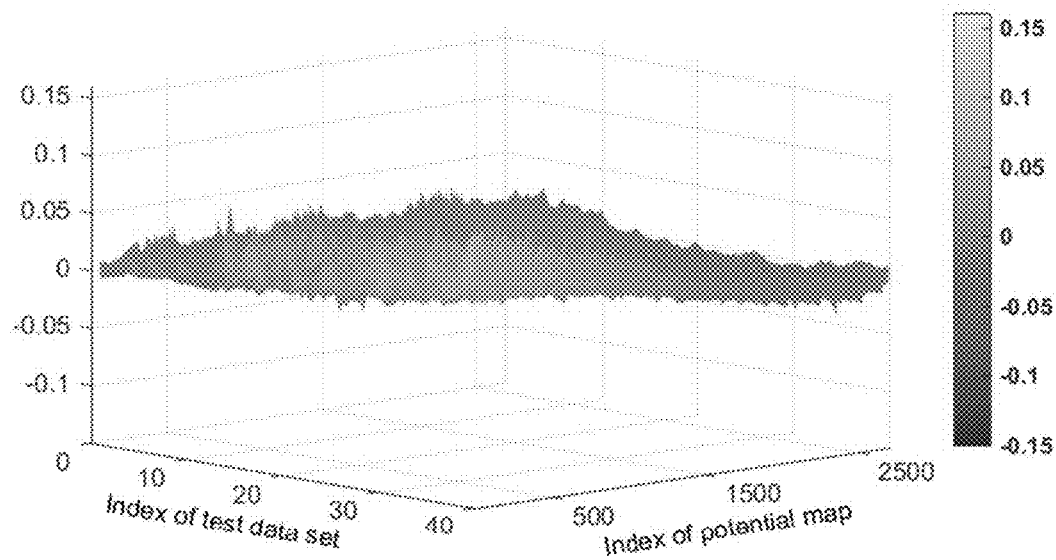
FIG. 23F is a graph showing CC of potential maps generated by the L-curve method subtracted from the CC values of potential maps generated by the SP method; warm colors represent positive differences and cold colors represent negative differences; X-axis, index of test data set; Y-axis, index of the uterine site or potential map; Z-axis, the difference in values.
Figure 23G:
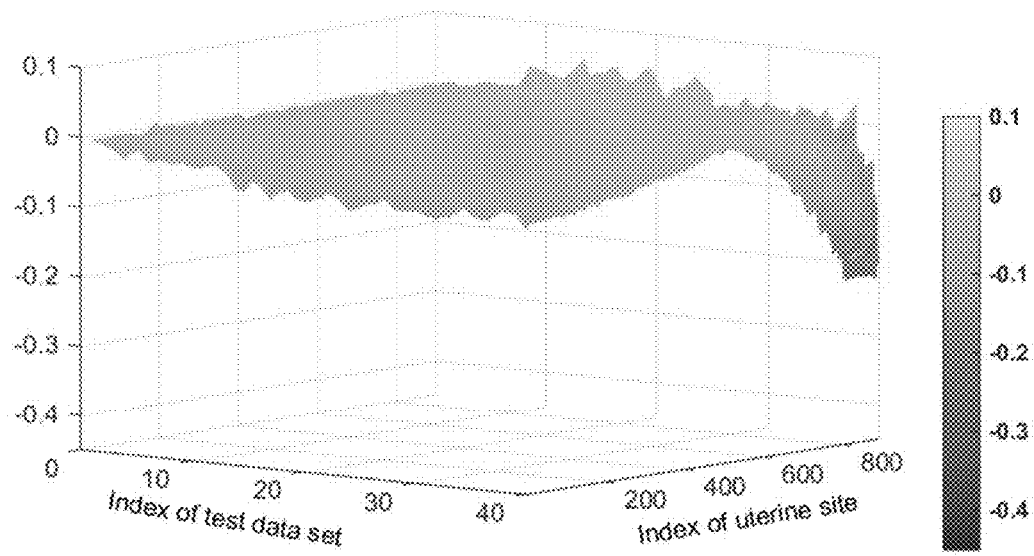
FIG. 23G is a graph showing RE values of electrograms generated by the L-curve method subtracted from the RE values of electrograms generated by the SP method; warm colors represent positive differences and cold colors represent negative differences; X-axis, index of test data set; Y-axis, index of the uterine site or potential map; Z-axis, the difference in values.
Figure 23H:
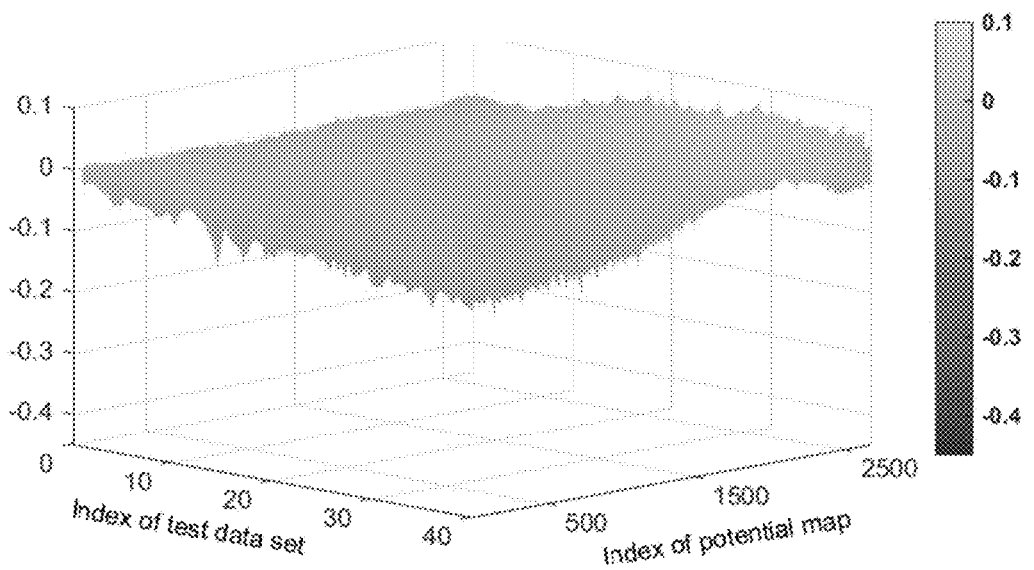
FIG. 23H is a graph showing RE values of potential maps generated by the L-curve method subtracted from the RE values of potential maps generated by the SP method; warm colors represent positive differences and cold colors represent negative differences; X-axis, index of test data set; Y-axis, index of the uterine site or potential map; Z-axis, the difference in values.

To compare the performance of the three methods, we first calculated the CC and RE values between the reconstructed electrograms and potential maps and the simulated electrograms and potential maps. Then, we calculated the difference of reconstruction accuracies between mean CRESO and SP methods (FIGS. 23A-23D), and between the L-Curve and SP methods (FIGS. 23E-23H) for each dataset. These differences were rendered to a surface plot in FIGS. 23A-23H). The datasets were sorted by geometry eccentricity and noise level, and a larger index corresponded to large eccentricity and higher noise level. The reconstructed electrogram accuracies of the three methods were similar at low eccentricity and low noise level. However, at larger eccentricity and higher noise levels, the SP method was superior to the mean CRESO and L-Curve methods, especially at the anterior uterine sites. The largest differences of electrogram CC and RE between the SP and mean CRESO methods were 0.15 and 0.4, respectively (FIGS. 23A and 23C). The largest differences of electrogram CC and RE between the SP and L-Curve methods were 0.07 and 0.2, respectively (FIGS. 23E and 23H). The potential maps were reconstructed with the SP method were slightly more accurate than those generated with the other two methods (FIGS. 23B, 23D, 23F, and 23H).

Comparison of Reconstruction Accuracy in RPI Geometry

Single Current Dipole

Figures 28A, 28B:
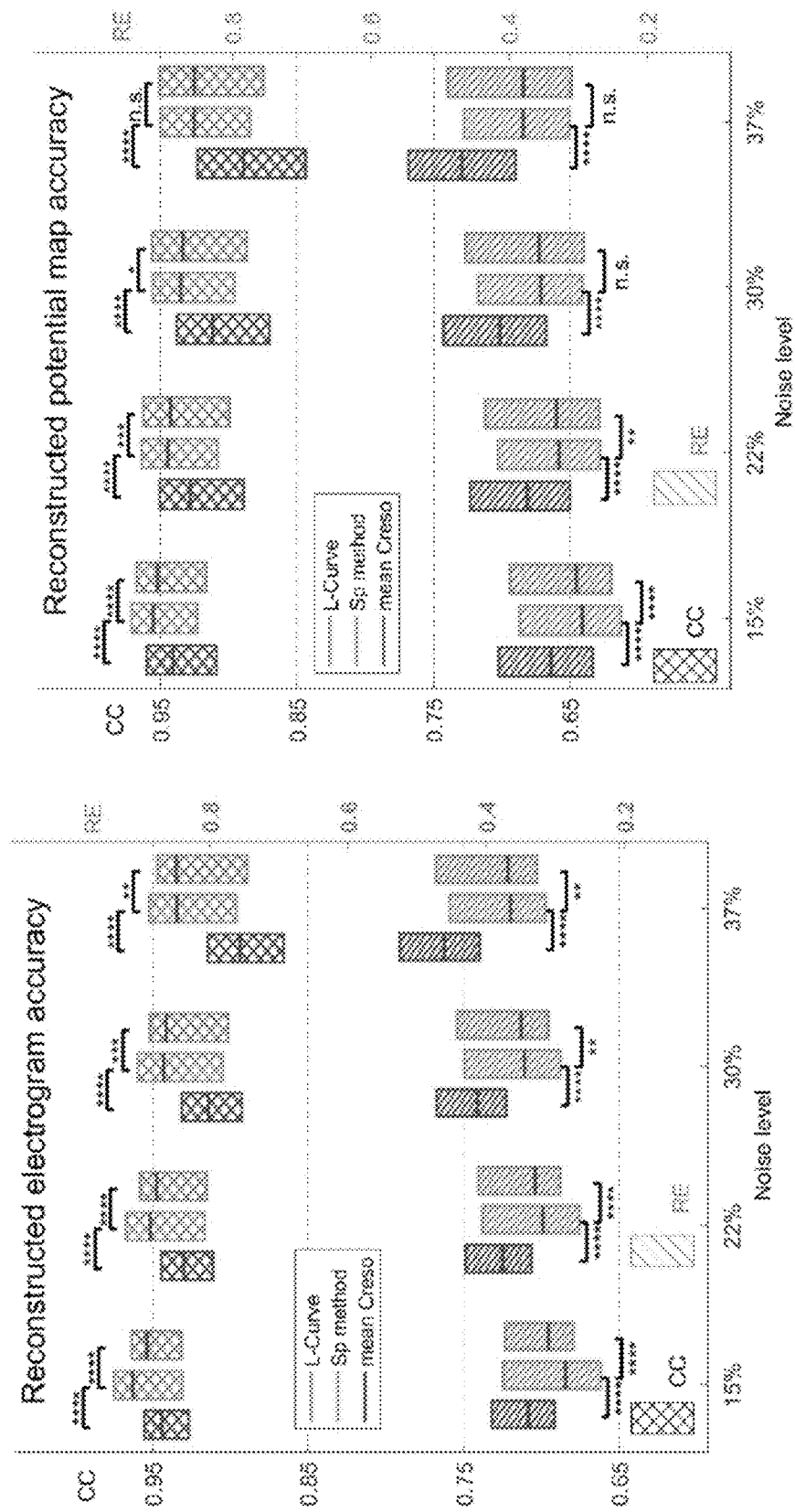
FIG. 28A is a graph comparing reconstructed electrogram accuracy of $\lambda_{SP}$, mean CRESO λ, and L-Curve λ; cross box indicates CC values and striped box indicates RE values; blue, orange, and pink represent mean CRESO method, SP method, and L-Curve method, respectively; n.s., not significant, * $P<0.05$,  $P<10^{-2}$, * $P<10^{-3}$, **** $P<10^{-4}$, compared to SP method.
FIG. 28B is a graph comparing reconstructed potential map accuracy of Asp, mean CRESO λ, and L-Curve λ; cross box indicates CC values and striped box indicates RE values; blue, orange, and pink represent mean CRESO method, SP method, and L-Curve method, respectively; n.s., not significant, * $P<0.05$,  $P<10^{-2}$, * $P<10^{-3}$, **** $P<10^{-4}$, compared to SP method.

We simulated BSPMs with the three-layer RPI geometry (FIG. 19B) and single current dipoles. Four levels of white Gaussian noise were added to BSPMs, with average peak-to-peak magnitudes 15%, 22%, 30%, and 37% of the signal. We calculated $\lambda_{SP}$ values according to the procedures shown in FIG. 26, used them to reconstruct uterine potentials, and compared the accuracy of the SP method to that of the mean CRESO and L-Curve methods. The median, first quartile, and third quartile of CC and RE values of reconstructions with the three methods under different levels of noise contamination are shown in FIGS. 28A and 28B. To assess the performance of the three methods, a one-tail Wilcoxon rank-sum test was applied between SP and mean CRESO methods, and between SP and L-Curve methods. The electrograms and potential maps were reconstructed significantly more accurately ($P<10^{-4}$) with $\lambda_{SP}$ than with the mean CRESO method at all four noise levels. Moreover, at 15% and 37% noise, the median electrogram CCs of SP reconstructions were 2% and 4.5%, respectively, higher than those of CRESO reconstructions; the median electrogram REs of SP reconstructions were 15.7% and 20.8%, respectively, lower than those of CRESO reconstructions; the median potential map CCs of SP reconstructions were 1.5% and 4.1% higher, respectively, than those of CRESO reconstructions; the median potential map REs of SP reconstructions were 13% and 18.9%, respectively, lower than those of CRESO reconstructions. Electrograms generated with the SP method were significantly ($P<10^{-2}$) more accurate than those generated with the L-Curve method. The accuracy of potential maps reconstructed with the SP method were significantly higher ($P<10^{-2}$) than those reconstructed with the L-Curve method when the noise level was less than 30%. The exact P-values are listed in Table 3 below.

TABLE 3

P-values of one- tail Wilcoxon rank-sum test

| FIGS. | PARAMETER | METHOD | NOISE LEVEL | | | |
|---|---|---|---|---|---|---|
| | | | 15% | 22% | 30% | 37% |
| 28A, B | Electrogram CC | SP - CRESO | $1.2 * 10^{-34}$ | $6.7 * 10^{-35}$ | $2.7 * 10^{-44}$ | $2.3 * 10^{-65}$ |
| | | SP - L-Curve | $1.4 * 10^{-13}$ | $4.5 * 10^{-7}$ | $3.3 * 10^{-4}$ | 0.0052 |
| | Electrogram RE | SP - CRESO | $6.6 * 10^{-32}$ | $1.4 * 10^{-33}$ | $2.5 * 10^{-44}$ | $5.4 * 10^{-69}$ |
| | | SP - L-Curve | $5.1 * 10^{-11}$ | $7.6 * 10^{-6}$ | 0.0012 | 0.0078 |
| | Potential map CC | SP - CRESO | $2.0 * 10^{-58}$ | $4.1 * 10^{-58}$ | $1.5 * 10^{-81}$ | $1.3 * 10^{-140}$ |
| | | SP - L-Curve | $1.7 * 10^{-12}$ | $6.8 * 10^{-5}$ | 0.0122 | 0.051 |
| | Potential map RE | SP - CRESO | $6.7 * 10^{-60}$ | $9.7 * 10^{-60}$ | $2.5 * 10^{-88}$ | $3.9 * 10^{-165}$ |
| | | SP - L-Curve | $1.1 * 10^{-10}$ | 0.0014 | 0.069 | 0.147 |
| 29B, C | Electrogram CC | SP - CRESO | $4.9 * 10^{-35}$ | $6.4 * 10^{-38}$ | $9.1 * 10^{-47}$ | $2.1 * 10^{-56}$ |
| | Electrogram RE | SP - CRESO | $6.4 * 10^{-18}$ | $2.9 * 10^{-21}$ | $1.2 * 27$ | $9.3 * 10^{-35}$ |
| | Potential map CC | SP - CRESO | 0.97 | 0.87 | 0.57 | 0.47 |
| | | SP - L-Curve | 0.0048 | 0.35 | 0.8 | 0.9 |
| | Potential map RE | SP - CRESO | 0.99 | 0.97 | 0.92 | 0.86 |
| | | SP - L-Curve | 0.46 | 0.17 | 0.008 | 0.003 |

Multiple Current Dipoles

Finally, we simulated BSPMs with the three-layer RPI geometry and three current dipoles (Table 2). Four levels of white Gaussian noise were added to the simulated BSPMs, with average peak-to-peak magnitudes 15%, 22%, 30%, and 37% of the signal. We calculated $\lambda_{SP}$ values, used them to reconstruct uterine potentials, and compared the reconstruction accuracy of the SP method to that of the mean CRESO and L-Curve methods. FIG. 25E shows representative simulated electrograms and electrograms reconstructed with the three regularization methods. The L-Curve method failed to reconstruct accurate uterine electrograms at any of the sites (CC<0.1, RE>10). At left lateral, anterior, and right lateral sites (i, ii, and iii), the SP-reconstructed electrograms were more accurate than those reconstructed with the mean CRESO method, both qualitatively and quantitatively (CC and RE).

Figure 29A:
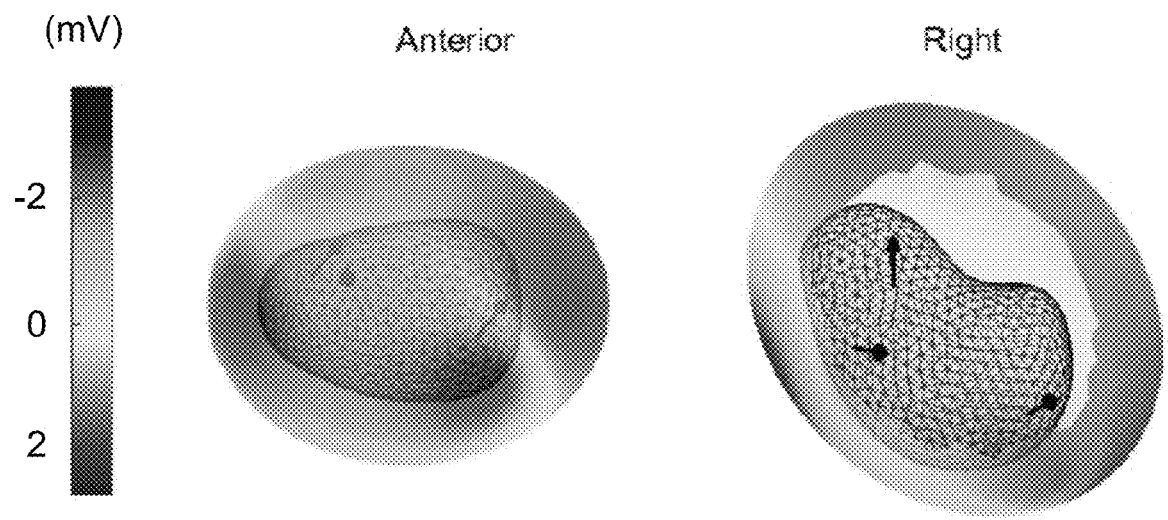
FIG. 29A is a body surface potential map with RPI geometry setting shown in right and anterior views. Black mesh represents RPI uterine surface. Black arrows represent dipole locations and directions; black mesh inside the color map is the uterine surface geometry.
Figure 29B:
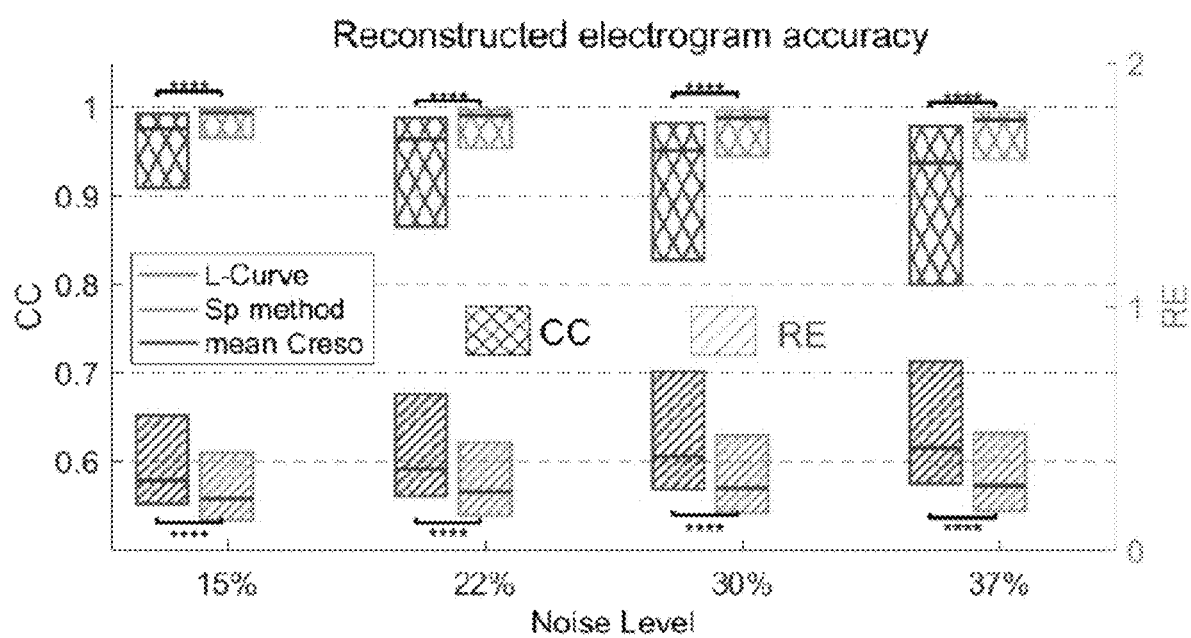
FIG. 29B is a graph comparing reconstructed electrogram accuracies of $\lambda_{SP}$ as well as mean CRESO and L-Curve λ. The electrogram accuracy of L-Curve was too small to be shown in the figure. Cross-hatched box indicates CC values, and striped box indicates RE values. Blue, orange, and pink represent mean CRESO method, SP method, and L-Curve method, respectively. n.s., not significant, * $P<0.05$,  $P<10^{-2}$, * $P<10^{-3}$, **** $P<10^{-4}$, compared to SP method.
Figure 29C:
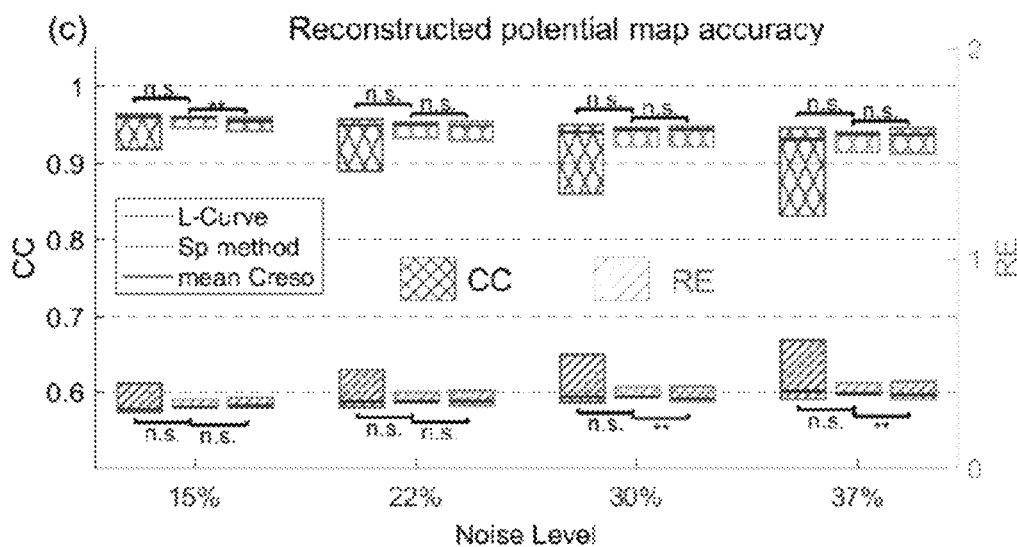
FIG. 29C is a graph comparing reconstructed potential map accuracies of $\lambda_{SP}$ as well as mean CRESO and L-Curve λ. Cross-hatched box indicates CC values, and striped box indicates RE values. Blue, orange, and pink represent mean CRESO method, SP method, and L-Curve method, respectively. n.s., not significant, * $P<0.05$,  $P<10^{-2}$, * $P<10^{-3}$, **** $P<10^{-4}$, compared to SP method.

A representative BSPM was rendered in a heat map (FIG. 29A) in which warm colors represent positive potentials and cool colors represent negative potentials. We then evaluated the reconstruction accuracy of all 900 electrograms and 2700 potential maps. FIGS. 29B and 29C show median, first quartile, and third quartile reconstruction accuracies of the three regularization methods under the four levels of noise contamination. The boxplots of CC and RE values of electrograms reconstructed with L-Curve are not shown because the maximum CC was less than 0.5 and the minimum RE was larger than 2.2, even at the lowest level of noise. Electrograms reconstructed with $\lambda_{SP}$ were significantly more accurate ($P<10^{-10}$ by one-tail Wilcoxon rank-sum test) than those reconstructed with mean CRESO, especially at higher noise levels. Moreover, at 15% and 37% noise, the median electrogram CCs of SP reconstructions were 1.8% and 5.3%, respectively, higher than those of CRESO reconstructions, and the median electrogram REs were 25.7% and 36.5%, respectively, lower than those of CRESO reconstructions. The potential map CC and RE of the SP reconstructions were not significantly differ from those of the mean CRESO and L-Curve reconstructions. The exact P-values are listed in Table 3 above.

Discussion

This study demonstrates that the optimal regularization parameter for EMMI is spatially dependent. Moreover, in simulations with spherical geometries with different eccentricities and various levels of noise contamination, the SP method resulted in more accurate reconstructions than the conventional L-Curve and CRESO methods, especially for highly eccentric body-uterus geometries and severe noise contamination. We also tested the SP method on a realistic geometry and current dipole models and found that the SP-reconstructed electrograms were more accurate (higher CC and lower RE values) than those reconstructed with the L-Curve or CRESO methods. The SP method captures the unique spatial information of each uterine site, converts it into optimal regularization parameters, and significantly improves the accuracy for reconstructing uterine electrograms. The SP method would be advantageous in clinical applications, as a hospital environment contains multiple electrical noise sources, and body-uterus geometry is severely eccentric in pregnant women. Moreover, because uterine electrograms are the foundation of constructing activation sequences, the SP method can potentially enhance the clinical application of EMMI.

This example demonstrated that the SP method is a better regularization technique for the EMMI inverse computation, which may facilitate clinical use of EMMI. Moreover, the SP method may be used to improve the accuracy of other electrical imaging modalities, such as electrocardiographic Imaging.

Example 5: Atlas-Based EMMI

Figure 31:
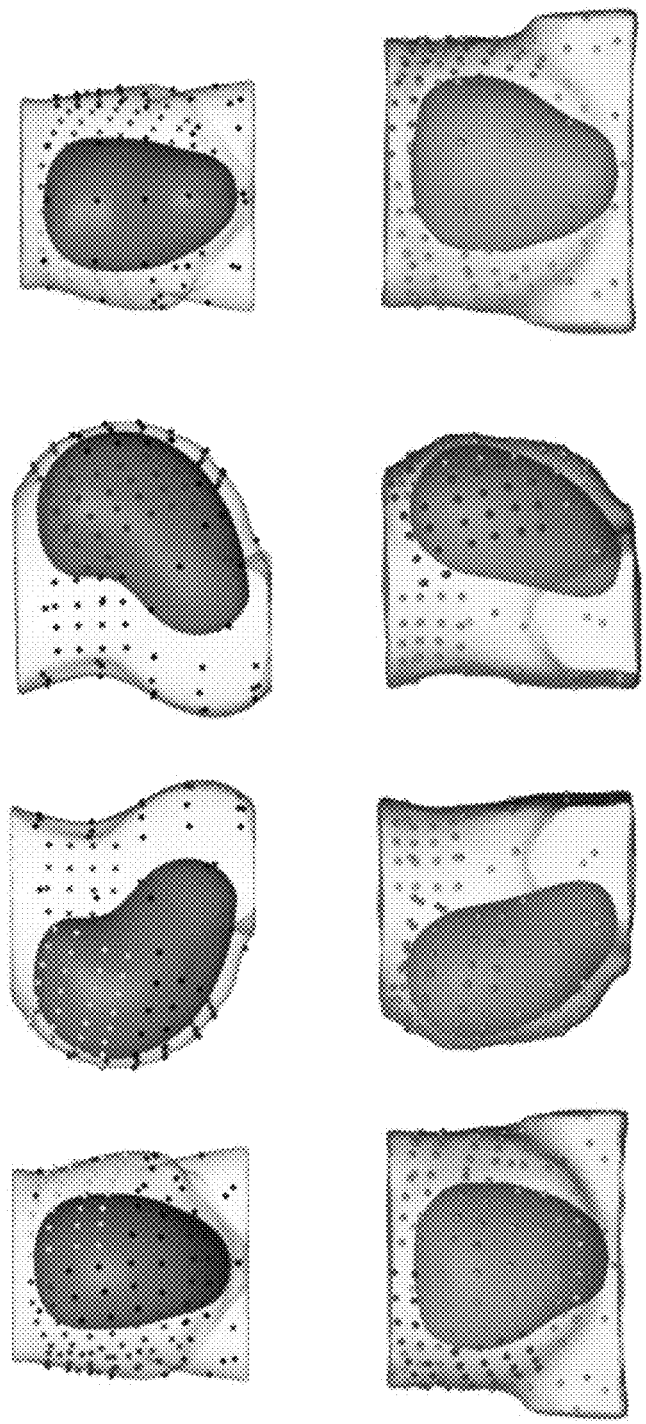
FIG. 31 is a series of diagrams comparing body-uterus geometries obtained using atlas-based and EMMI patient-specific methods.
Figure 32A:
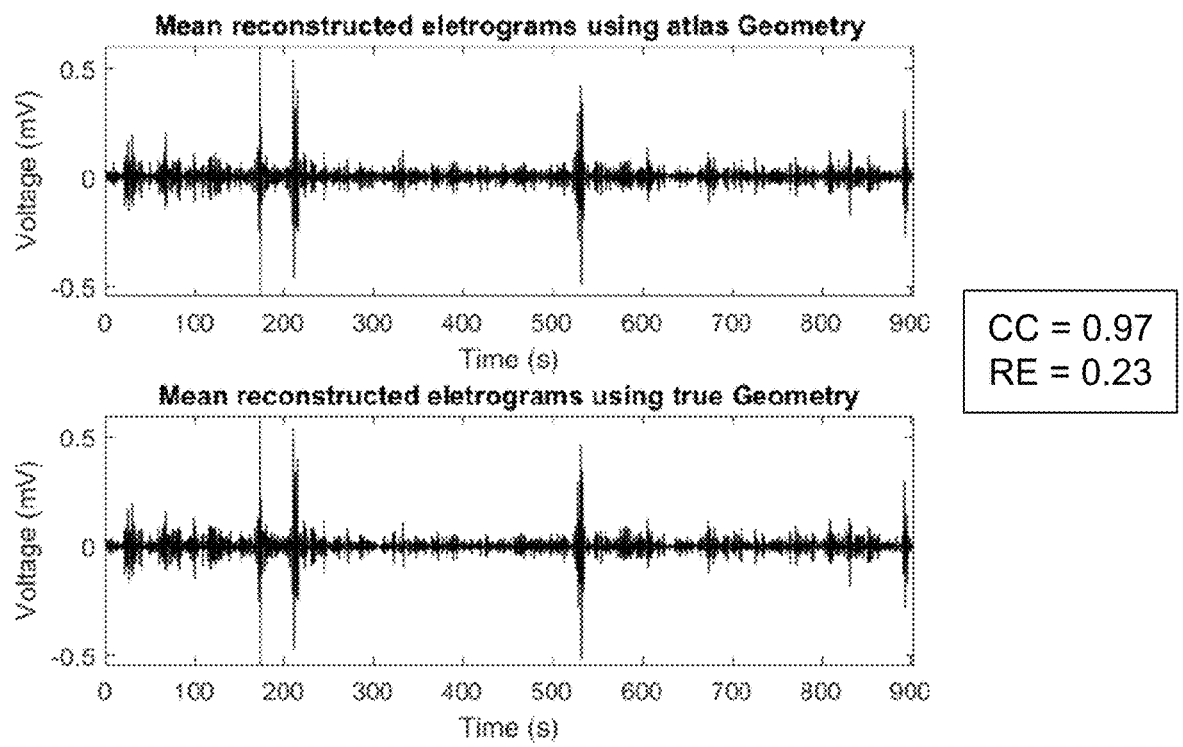
FIG. 32A contains graphs comparing mean reconstructed electrograms obtained from a first EMMI recording based on atlas-based (upper graph) and individually-measured (lower graph) body-uterus geometries. Correlation coefficient (CC) quantifies the morphology similarity ([0,1]); CC=1 means the morphologies of two signals are exactly the same. Relative error (RE) quantifies the magnitude difference (≥0); RE=0 means zero magnitude difference.
Figure 32B:
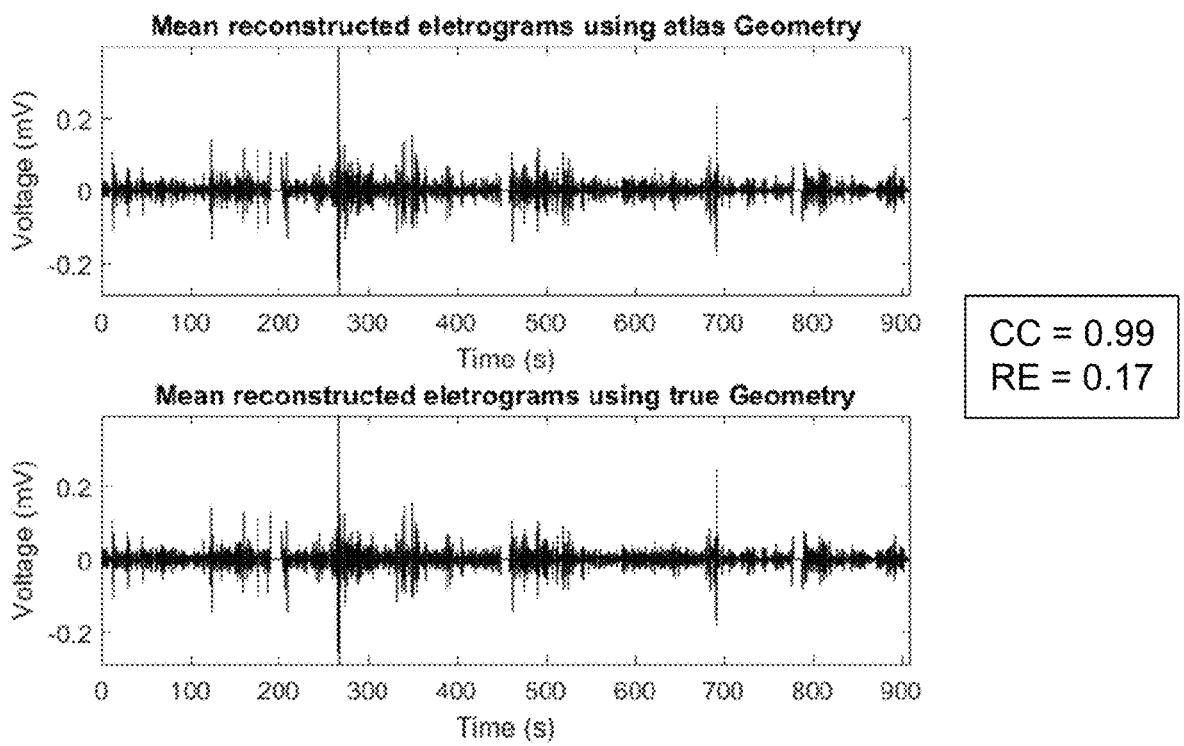
FIG. 32B contains graphs comparing mean reconstructed electrograms obtained from a second EMMI recording based on atlas-based (upper graph) and individually-measured (lower graph) body-uterus geometries. Correlation coefficient (CC) quantifies the morphology similarity ([0,1]); CC=1 means the morphologies of two signals are exactly the same. Relative error (RE) quantifies the magnitude difference (≥0); RE=0 means zero magnitude difference.
Figure 32C:
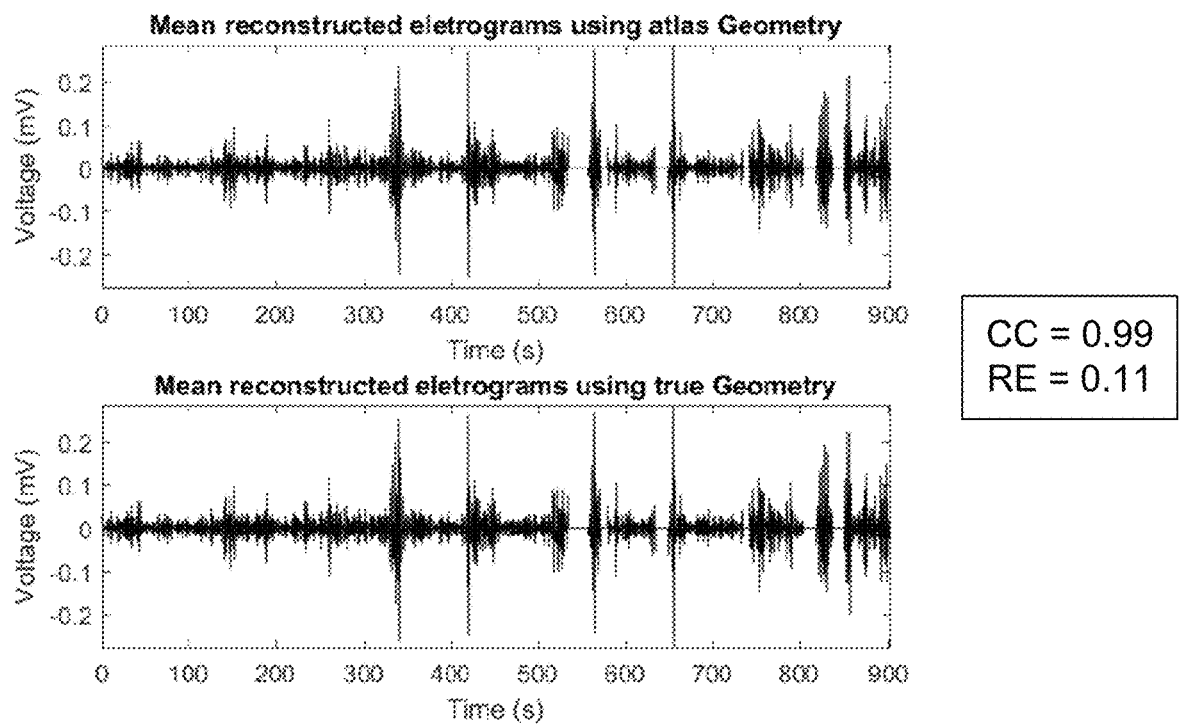
FIG. 32C contains graphs comparing mean reconstructed electrograms obtained from a third EMMI recording based on atlas-based (upper graph) and individually-measured (lower graph) body-uterus geometries. Correlation coefficient (CC) quantifies the morphology similarity ([0,1]); CC=1 means the morphologies of two signals are exactly the same. Relative error (RE) quantifies the magnitude difference (≥0); RE=0 means zero magnitude difference.
Figure 32D:
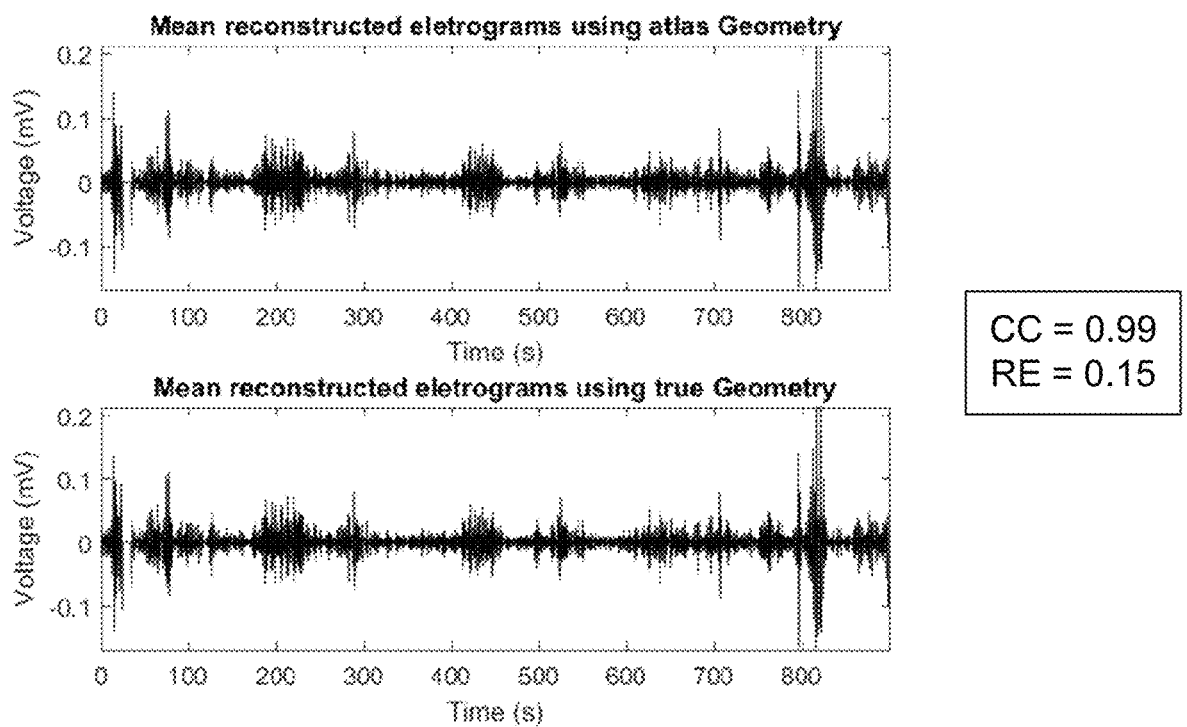
FIG. 32D contains graphs comparing mean reconstructed electrograms obtained from a fourth EMMI recording based on atlas-based (upper graph) and individually-measured (lower graph) body-uterus geometries. Correlation coefficient (CC) quantifies the morphology similarity ([0,1]); CC=1 means the morphologies of two signals are exactly the same. Relative error (RE) quantifies the magnitude difference (≥0); RE=0 means zero magnitude difference.
Figure 33:
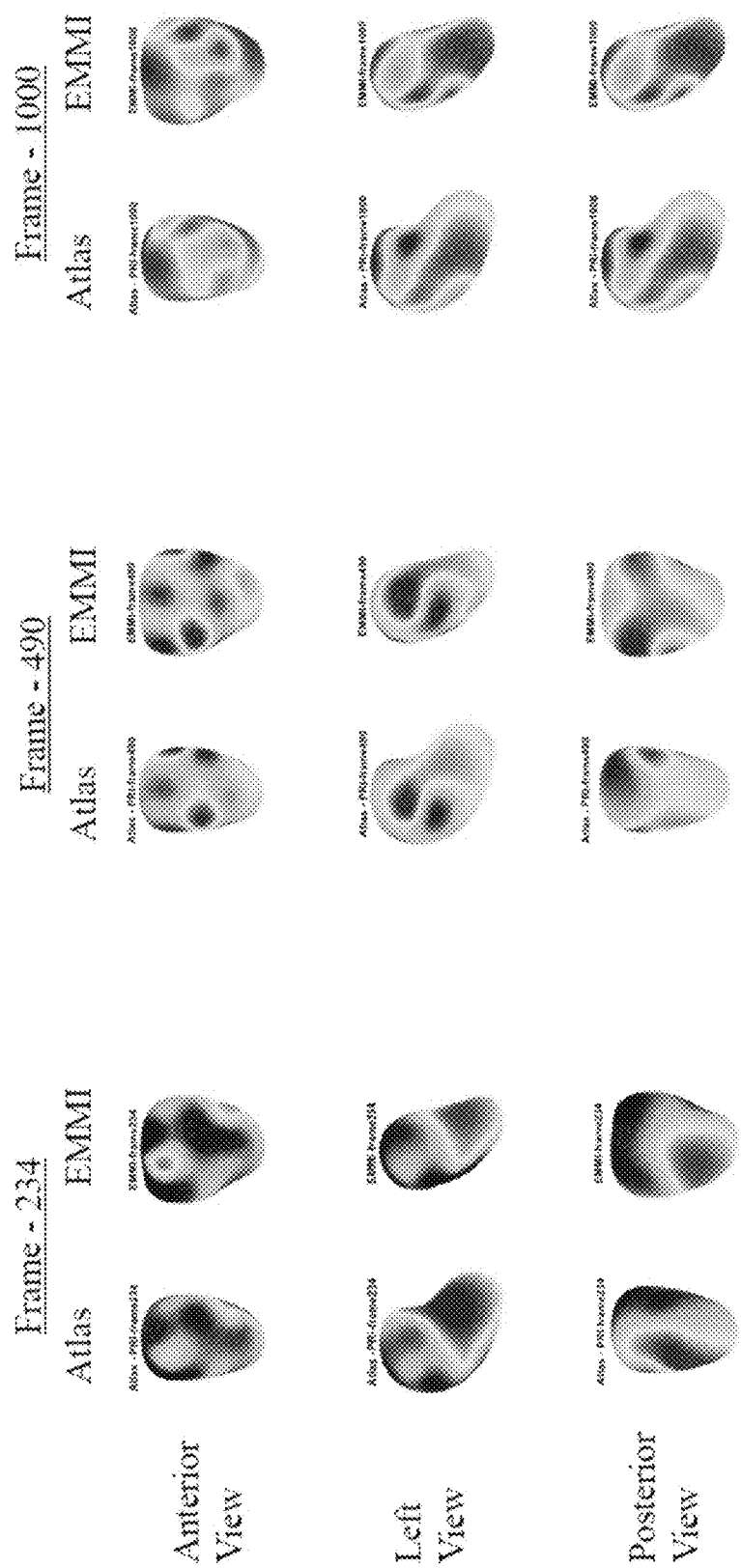
FIG. 33 contains a series of potential maps derived from three different frames of the EMMI recording of FIG. 32D, obtained based on atlas-based versus individually-measured body-uterus geometries. All potential maps share the same color scale (not shown).
Figure 34A:
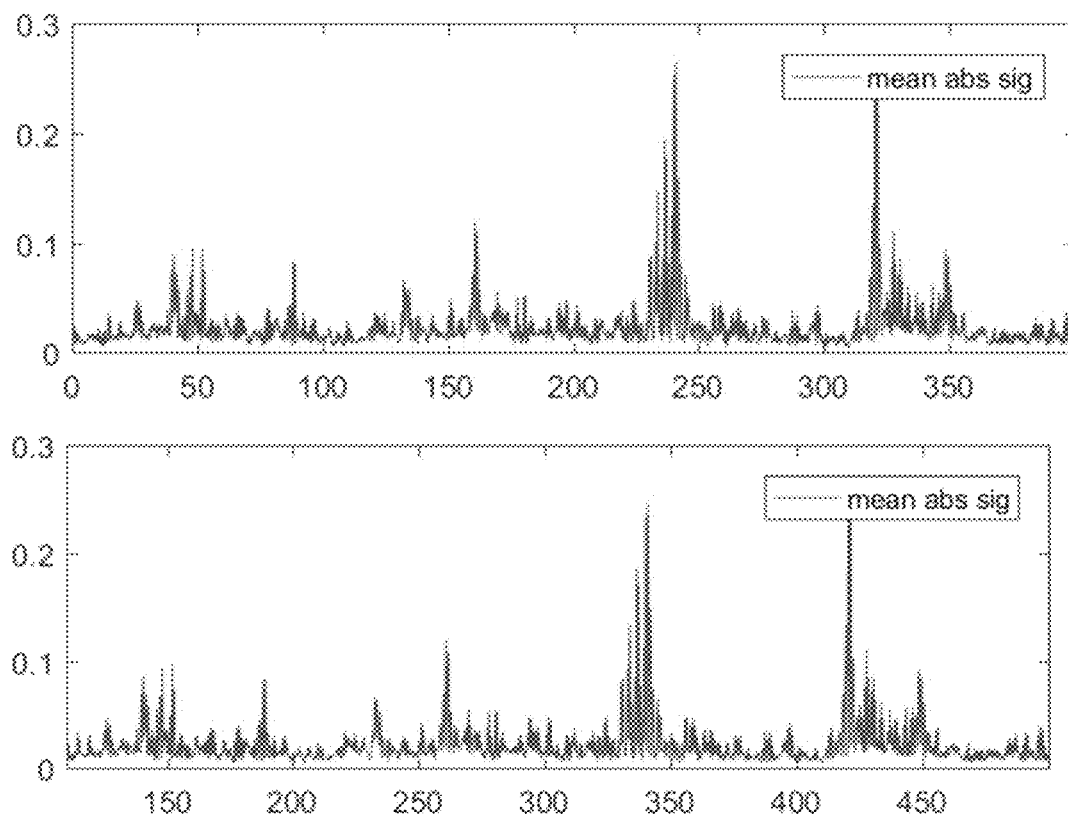
FIG. 34A is a comparison of mean absolute signals based on atlas-based (upper) versus individually-measured (lower) body-uterus geometries.
Figure 34B:
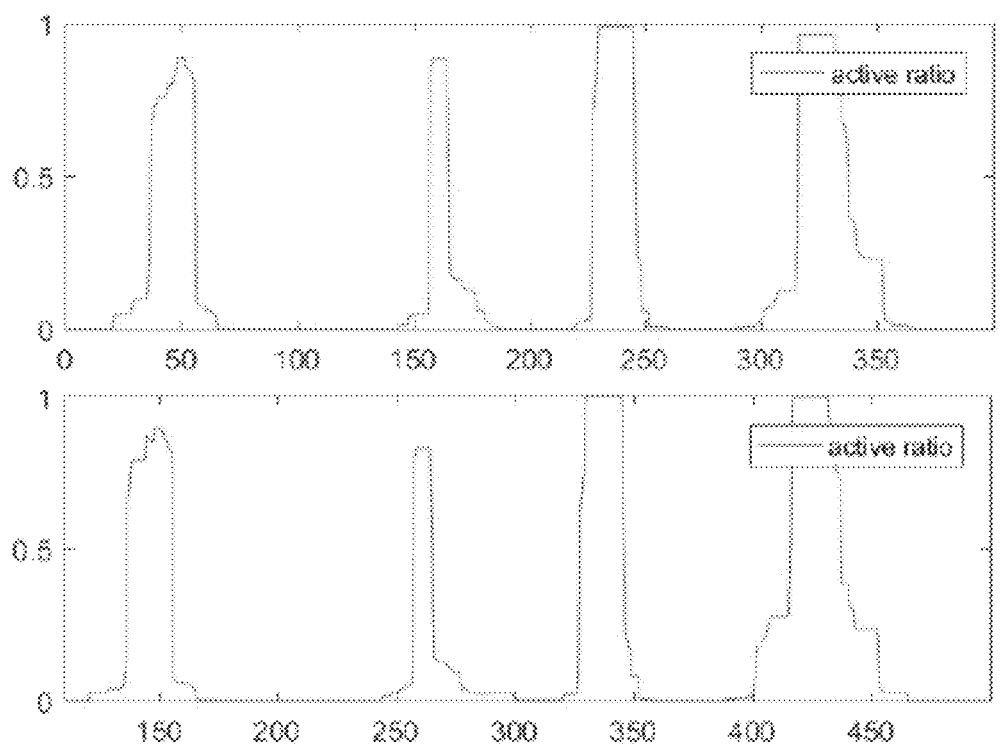
FIG. 34B is a comparison of activation ratios based on atlas-based (upper) versus individually-measured (lower) body-uterus geometries.

This example describes the development and validation of an Atlas-Based EMMI method for monitoring uterine contraction patterns in subjects without need for patient-specific body-uterine geometry data. An experimental Artec 3D surface was projected to RPI geometry and used to generate an atlas body-uterus geometry. Experimentally recorded EMG data was combined with the atlas body-uterus geometry to reconstruct the uterine electrical signals using the SP method as described above. The reconstructed signals between the atlas-based EMMI and EMMI sing patient-specific body-uterine geometry (see FIGS. 32A, 32B, 32C, and 32D) were compared in terms of electrograms, potential maps and activation ratios. Sensor-uterus geometries were found to be similar between atlas and patient-specific geometry (see FIG. 31). Based on the CC and RE, the reconstructed electrograms using atlas geometry were similar to those using patient-specific geometry (see FIG. 34A), as were the potential map patterns (see FIG. 33) and activation ratio distributions (see FIG. 34B). The results described in this example demonstrated that Atlas-based EMMI is sufficiently accurate to noninvasively image and characterize the properties of electrical uterine contractions in clinical contexts.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

What is claimed is:
1. A system for monitoring uterine contractions in a subject, the system comprising:
 a. at least one electrode patch, each electrode patch comprising an adhesive flexible membrane and a plurality of electrodes affixed to the flexible membrane, the plurality of electrodes extending through the flexible membrane in an array pattern, wherein the at least one electrode patch is configured to adhere to a body surface overlying a uterus of the subject;
 b. a computing device operatively coupled to the plurality of electrodes, the computing device comprising at least one processor and a non-volatile computer-readable media, the non-volatile computer-readable media containing instructions executable on the at least one processor to:
  i. receive a body-uterus geometry of the subject, the body-uterus geometry comprising a plurality of 3D positions of a uterus surface and the body surface of the subject, and each 3D position of each electrode on the body surface of the subject;
  ii. transform the body-uterus geometry G into U, $\Sigma$, and X using a single value composition method, wherein U is a matrix of singular vectors spanning the body surface, $\Sigma$ is a diagonal matrix of singular values ($\sigma_1$, $\sigma_i$, ... $\sigma_Z$), X is a matrix of singular vectors spanning the uterine surface, M is the number of body surface sites, N is the number of uterine sites and Z=min(M, N);
  iii. receive a plurality of EMG signals from the plurality of electrodes;
  iv. transform the plurality of EMG signals into at least one uterine potential map based on the body-uterus geometry of the subject; and
  v. detect motion artifacts in the at least one uterine potential map.

2. The system of claim 1, further comprising at least one MRI marker patch, each MRI marker patch comprising an adhesive flexible membrane and a plurality of MRI markers affixed to the flexible membrane in an MRI marker pattern matched to the array pattern of the plurality of electrodes of the electrode patch, wherein the at least one MRI marker patch is configured to adhere to the body surface overlying the uterus of the subject such that each location of each MRI marker is matched to a corresponding location of each electrode when the at least one electrode patch is adhered to the body surface of the subject.

3. The system of claim 2, wherein the non-volatile computer-readable media further contains instructions executable on the at least one processor to:
 a. receive an MRI image of the subject with the at least one MRI marker patch adhered to the body surface of the subject;
 b. receive a 3D optical scan of the subject with the at least one electrode patch adhered to the body surface of the subject; and c. register the MRI image with the 3D optical scan to produce the body-uterus geometry.

4. The system of claim 3, wherein the non-volatile computer-readable media further contains instructions executable on the at least one processor to transform the at least one uterine potential map into at least one uterine electrogram and/or at least one isochrone map.

5. The system of claim 4, wherein the non-volatile computer-readable media further contains instructions executable on the at least one processor to transform the at least one isochrone map into at least one summary parameter selected from activation ratio, activation duration, synchronized ratio, slow conduction ratio, and/or median propagation speed.

6. The system of claim 5, further comprising an optical 3D scanner operatively coupled to the computing device, the optical 3D scanner configured to obtain the 3D optical scan of the subject with the at least one electrode patch adhered to the body surface of the subject.

7. The system of claim 6, further comprising an MRI scanner operatively coupled to the computing device, the MRI scanner configured to obtain the MRI image of the subject with the at least one MRI marker patch adhered to the body surface of the subject.

8. The system of claim 7, wherein the non-volatile computer-readable media further contains instructions executable on the at least one processor to classify a labor status of the subject based on at least one of the at least one uterine potential map, the at least one uterine electrogram, the at least one isochrone map, and the at least one summary parameter.

9. The system of claim 8, wherein the labor status of the subject is selected from early labor, late labor, preterm birth, and labor arrest.

10. The system of claim 1, wherein the non-volatile computer-readable media further contains instructions executable on the at least one processor to filter the motion artifacts out of the at least one uterine potential map.

11. The system of claim 1, wherein the body uterus geometry is generated using MRI images segmented slice by slice.

12. The system of claim 1, wherein the non-volatile computer-readable media further contains instructions executable on the at least one processor to transform the body surface potential map $\Phi_B$ and the body-uterus geometry G into a plurality of spatial dependent (SP) regularization factors $\lambda_{SP}=[\lambda_1, \lambda_1, \ldots \lambda_k, \lambda_N]$ using the function $f(G, \Phi_B)$, wherein $\lambda_k$ is the regularization factor corresponding to the $k^{th}$ uterine surface position of N total positions.

13. The system of claim 12, wherein transforming the plurality of EMG signals to the at least one uterine potential map is accomplished using $$\Phi_U = \sum_{i=1}^{Z} \frac{\sigma_i^2}{\sigma_i^2 + \lambda_k} \frac{d_i}{\sigma_i} X_{k,i};$$

wherein $d_i$ is a decomposition of the body surface potential $\Phi_B$ onto the $i^{th}$ singular vector of U, according to $d_i = U_{.,i}^T \Phi_B$.

14. The system of claim 1, wherein the motion artifacts comprise maternal and/or fetal movements.

* * * * *